(12) United States Patent
Helmke et al.

(10) Patent No.: US 6,750,222 B2
(45) Date of Patent: Jun. 15, 2004

(54) SUBSTITUTED PHENYL DERIVATIVES

(75) Inventors: Hendrik Helmke, Liederbach (DE); Michael Gerhard Hoffmann, Flörsheim (DE); Klaus Haaf, Kelkheim (DE); Lothar Willms, Hofheim (DE); Thomas Auler, Bad Soden (DE); Hermann Bieringer, Eppstein (DE); Hubert Menne, Hofheim (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 10/318,573

(22) Filed: Dec. 13, 2002

(65) Prior Publication Data

US 2003/0228982 A1 Dec. 11, 2003

(30) Foreign Application Priority Data

Dec. 15, 2001 (DE) .......................... 101 61 765

(51) Int. Cl.$^7$ ...................... A01N 43/56; C07D 231/08; C07D 231/18; C07D 231/04
(52) U.S. Cl. ................. 514/282; 548/366.1; 548/370.4; 548/370.7
(58) Field of Search ....................... 504/282; 548/370.4, 548/370.7, 366.1

(56) References Cited

U.S. PATENT DOCUMENTS

| | | | |
|---|---|---|---|
| 3,884,955 A | 5/1975 | Von Der Crone et al. | |
| 5,698,495 A | 12/1997 | Mathews et al. ........... | 504/282 |
| 5,786,392 A | 7/1998 | Silverman et al. ....... | 514/772.4 |

FOREIGN PATENT DOCUMENTS

| | | |
|---|---|---|
| CA | 1157022 | 11/1983 |
| DE | 3602379 | 7/1987 |
| EP | 0 027 965 A2 | 5/1981 |
| EP | 0 307 103 A2 | 3/1989 |
| EP | 0 348 002 A2 | 12/1989 |
| GB | 2 050 168 A1 | 1/1981 |
| GB | 2 238 789 A1 | 6/1991 |
| JP | 7056366 | 3/1995 |
| JP | 10-7657 | 1/1998 |
| JP | 2001098071 | 4/2001 |
| WO | WO 97/18196 | 5/1997 |
| WO | WO-99/18057 | 4/1999 |
| WO | WO 01/05769 A2 | 1/2001 |

OTHER PUBLICATIONS

English language abstract of JP 10007657 (Jan. 13, 1998).
Brockhaus, Die Enzyklopadie, Aug. 20, 1997. Stichwort, "Herbizide", p. 710 (1997).
English language abstract of JP7056366 (Mar. 3, 1995).
English language abstract of JP2001098071 (Apr. 10, 2001).

Primary Examiner—D. Margaret Seaman
(74) Attorney, Agent, or Firm—Connolly Bove Lodge and Hutz LLP

(57) ABSTRACT

The present invention relates to compounds of the formula (I) and/or salts thereof

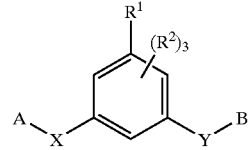

formula (I)

where $R^1$, $R^2$, A, B, X and Y are as defined in claim 1. The compounds according to the invention are suitable for use as herbicides and plant growth regulators.

12 Claims, No Drawings

SUBSTITUTED PHENYL DERIVATIVES

It is known that substituted phenyl derivatives can have herbicidal and plant-growth-regulating properties (cf., for example, DE 3602-379-A, JP 10007657, U.S. Pat. No. 5,698,495, U.S. Pat. No. 5,786,392, WO 9718196). However, on application, these compounds frequently have disadvantages, such as, for example, long persistency, insufficient selectivity in important crops of useful plants or lack of activity against harmful plants.

This invention now provides phenyl derivatives substituted in a particular manner which can be used advantageously as herbicides and plant growth regulators.

Accordingly, the present invention provides compounds of the formula (I) and/or salts thereof

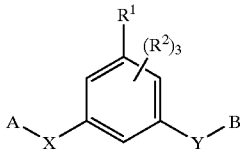

formula (I)

where

A is a phenyl radical or a heteroaromatic radical having 5 or 6 ring atoms, such as pyridyl, pyrazolyl or thienyl, which radicals carry, on one of the two ring atoms next but one to the ring atom to which X is attached, a substituent selected from the group consisting of $CH_3$, $CH_2F$, $CHF_2$, $CF_3$, $OCH_3$, $OCH_2F$, $OCHF_2$, $OCF_3$ and CN, preferably from the group consisting of $CH_2F$, $CHF_2$, $CF_3$, $OCH_2F$, $OCHF_2$, $OCF_3$ and CN, and optionally a second substituent selected from the group consisting of halogen, CN, $(C_1-C_8)$-alkyl, $(C_1-C_8)$-alkoxy and $(C_1-C_8)$-alkylthio, where each of the three last-mentioned radicals is unsubstituted or substituted by one or more radicals selected from the group consisting of halogen, CN, $(C_1-C_8)$-alkoxy and $(C_1-C_8)$-alkylthio, for example $(C_1-C_8)$-haloalkyl, $(C_1-C_8)$-haloalkyloxy, $(C_1-C_8)$-haloalkylthio or $(C_1-C_8)$-alkoxy-$(C_1-C_8)$-alkyloxy, X is O, S or $CH_2$, $R^1$ is hydroxyl, halogen, CN, NC, CHO or $CO(C_1-C_8)$-alkyl, where the alkyl group is unsubstituted or substituted, for example by one or more radicals selected from the group consisting of hydroxyl, halogen, CN, $(C_1-C_8)$-alkoxy, $(C_1-C_8)$-alkylthio, $(C_1-C_8)$-alkylsulfinyl, $(C_1-C_8)$-alkylsulfonyl and $[(C_1-C_8)$-alkoxy]-carbonyl, or $CONH_2$, $CSNH_2$, nitro, $SF_5$, $(C_1-C_8)$-alkyl, $(C_2-C_8)$-alkenyl or $(C_2-C_8)$-alkynyl, where the 3 last-mentioned radicals are unsubstituted or substituted, for example by one or more radicals selected from the group consisting of hydroxyl, halogen, CN, $(C_1-C_8)$-alkoxy, $(C_1-C_8)$-alkylthio, $(C_1-C_8)$-alkylsulfinyl, $(C_1-C_8)$-alkylsulfonyl and $[(C_1-C_8)$-alkoxy]carbonyl, or $(C_1-C_8)$-alkoxy, $[(C_1-C_8)$-alkyl] carbonyl or $(C_1-C_8)$-alkylsulfonyl, where the radicals are unsubstituted or substituted, for example by one or more radicals selected from the group consisting of hydroxyl, halogen, CN, $(C_1-C_8)$-alkoxy and $(C_1-C_8)$-alkylthio, or $S(O)_p$—$R^3$, where p=0, 1 or 2 and $R^3$ is $(C_1-C_8)$-alkyl, $(C_1-C_8)$-haloalkyl or $NR^4R^5$, where $R^4, R^5$ independently of one another are identical or different radicals H, $(C_1-C_8)$-alkyl, $(C_2-C_8)$-alkenyl, $(C_7-C_{10})$-arylalkyl, $(C_7-C_{10})$-alkylaryl or $(C_6-C_{10})$-aryl, where each of the five last-mentioned radicals is unsubstituted or substituted, for example by one or more radicals selected from the group consisting of hydroxyl, halogen, CN, $(C_1-C_8)$-alkoxy and $(C_1-C_8)$-alkylthio, or is $NR^4R^5$, where $R^4, R^5$ independently of one another are identical or different radicals H, $(C_1-C_8)$-alkyl, $(C_2-C_8)$-alkenyl, $(C_7-C_{10})$-arylalkyl, $(C_7-C_{10})$-alkylaryl or $(C_6-C_{10})$-aryl, where each of the five last-mentioned radicals is unsubstituted or substituted, for example by one or more radicals selected from the group consisting of hydroxyl, halogen, CN, $(C_1-C_8)$-alkoxy and $(C_1-C_8)$-alkylthio, or $R^1$ is a group of the formula

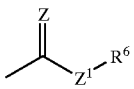

where $R^6$ is $(C_1-C_8)$-alkyl, which is unsubstituted or substituted, for example by one or more radicals selected from the group consisting of hydroxyl, halogen, CN, $(C_1-C_8)$-alkoxy and $(C_1-C_8)$-alkylthio, and Z=O or S, and $Z^1$=O or S, $R^2$ are identical or different radicals H, halogen, CN or $(C_1-C_8)$-alkyl, which are unsubstituted or substituted, for example by one or more radicals selected from the group consisting of hydroxyl, halogen, CN, $(C_1-C_8)$-alkoxy and $(C_1-C_8)$-alkylthio, Y is O—$(CR^8R^9)_q$, $S(O)_q$, NH, $CO(CR^8R^9)_q$ or $CR^8R^9$ and, if B is an unsubstituted or substituted aryl radical, an unsubstituted or substituted heterocyclyl radical, halogen or CN, Y may also be a bond, where $R^8$ and $R^9$ are identical or different radicals H, hydroxyl, halogen, CN, $(C_1-C_8)$-alkoxy or $(C_1-C_8)$-alkyl, where each of the two last-mentioned radicals is unsubstituted or substituted, for example by one or more radicals selected from the group consisting of hydroxyl, halogen, CN, $(C_1-C_8)$-alkoxy and $(C_1-C_8)$-alkylthio, and q=0, 1 or 2, and B is an unsubstituted or substituted aryl radical, for example an unsubstituted or substituted phenyl radical, or an unsubstituted or substituted heterocyclic radical, for example an unsubstituted or substituted heteroaromatic radical, such as unsubstituted or substituted pyridyl, pyrazolyl or thienyl, H, OH, halogen, CN, nitro, $SF_5$, $(C_1-C_8)$-alkyl, $(C_2-C_8)$-alkenyl or $(C_2-C_8)$-alkynyl, where the 3 last-mentioned radicals are unsubstituted or substituted, for example by one or more radicals selected from the group consisting of hydroxyl, halogen, CN, $(C_1-C_8)$-alkoxy, $(C_1-C_8)$-alkylthio, $(C_1-C_8)$-alkylsulfinyl, $(C_1-C_8)$-alkylsulfonyl, $[(C_1-C_8)$-alkoxy]-carbonyl, $(C_1-C_8)$-haloalkoxy, $(C_1-C_8)$-haloalkylthio and $(C_1-C_8)$-alkoxy-$(C_1-C_8)$-alkoxy, or an acyl radical, for example $[(C_1-C_8)$-alkyl]carbonyl, such as straight-chain or branched $[(C_1-C_8)$-alkyl] carbonyl or $[(C_3-C_6)$-cycloalkyl]carbonyl, $(C_6-C_{14})$-arylcarbonyl, $(C_1-C_8)$-alkylsulfonyl or $(C_6-C_{14})$-arylsulfonyl, where each of the radicals mentioned is unsubstituted or substituted, for example by one or more radicals selected from the group consisting of hydroxyl, halogen, $(C_1-C_8)$-alkoxy, $(C_1-C_8)$-alkylthio, ($C_1$–$C_8$)-alkylsulfinyl, ($C_1$–$C_8$)-alkylsulfonyl, [($C_1$–$C_8$)-alkoxy]carbonyl, ($C_1$–$C_8$)-haloalkoxy, ($C_1$–$C_8$)-haloalkylthio and CN, or $NR^{11}R^{12}$, where $R^{11}, R^{12}$ independently of one another are identical or different radicals H, ($C_1$–$C_8$)-alkyl, ($C_2$–$C_8$)-alkenyl, ($C_7$–$C_{10}$)-arylalkyl, ($C_7$–$C_{10}$)-alkylaryl, ($C_6$–$C_{10}$)-aryl or heteroaryl, where each of the six last-mentioned radicals is unsubstituted or substituted, for example by one or more radicals selected from the group consisting of hydroxyl, halogen, CN, ($C_1$–$C_8$)-alkoxy and ($C_1$–$C_8$)-alkylthio, or an acyl radical, for example [($C_1$–$C_8$)-alkyl]carbonyl, such as straight-chain or branched [($C_1$–$C_8$)-alkyl]-carbonyl or [($C_3$–$C_6$)-cycloalkyl]carbonyl, ($C_6$–$C_{14}$)-arylcarbonyl, ($C_6$–$C_{14}$)-aryl-($C_1$–$C_8$)-alkylcarbonyl, ($C_1$–$C_8$)-alkylsulfonyl or ($C_6$–$C_{14}$)-arylsulfonyl, where each of the radicals mentioned is unsubstituted or substituted, for example by one or more radicals selected from the group consisting of hydroxyl, halogen, ($C_1$–$C_8$)-alkoxy, ($C_1$–$C_8$)-alkylthio, ($C_1$–$C_8$)-alkylsulfinyl, ($C_1$–$C_8$)-alkylsulfonyl, [($C_1$–$C_8$)-alkoxy]carbonyl, ($C_1$–$C_8$)-haloalkoxy, ($C_1$–$C_8$)-haloalkylthio and CN, or B is a group of the formula

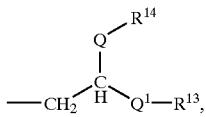

where $R^{13}$ is ($C_1$–$C_8$)-alkyl, which is unsubstituted or substituted, for example by one or more radicals selected from the group consisting of hydroxyl, halogen, CN, ($C_1$–$C_8$)-alkoxy and ($C_1$–$C_8$)-alkylthio, $R^{14}$ is ($C_1$–$C_8$)-alkyl, which is unsubstituted or substituted, for example by one or more radicals selected from the group consisting of hydroxyl, halogen, CN, ($C_1$–$C_8$)-alkoxy and ($C_1$–$C_8$)-alkylthio, or $R^{13}$ and $R^{14}$ together form a ring, Q=O or S, and $Q^1$=O or S.

In the formula (I) and hereinbelow, the carbon-containing radicals, such as alkyl, alkoxy, haloalkyl, alkylamino and alkylthio radicals, and the corresponding unsaturated and/or substituted radicals, can in each case be straight-chain or branched in the carbon skeleton or, for carbon numbers from 3 onwards, also be cyclic. Unless specifically indicated, the lower carbon skeletons, for example with 1 to 6 carbon atoms or, in the case of unsaturated groups, 2 to 6 carbon atoms, are preferred for these radicals. Alkyl radicals, including in the composed meanings, such as alkoxy, haloalkyl, etc., are, for example, methyl, ethyl, n-, i- or cyclopropyl, n-, i-, t-, 2- or cyclobutyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

A hydrocarbon-containing radical is a straight-chain, branched or cyclic, saturated or unsaturated, aliphatic or aromatic radical which has hydrocarbon units, for example alkyl, alkenyl, alkynyl, cycloalkyl, cycloalkenyl or aryl; here, aryl is a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl.

Aryl or aryl radical is a mono-, bi- or polycyclic, unsubstituted or substituted aromatic system, for example phenyl, naphthyl, indenyl, indanyl or pentalenyl, fluorenyl, preferably phenyl, which may be substituted, for example, by one or more, preferably 1, 2 or 3, radicals from the group consisting of halogen, such as F, Cl, Br, I, preferably F, Cl and Br, furthermore alkyl, haloalkyl, alkoxy, haloalkoxy, hydroxyl, amino, nitro, cyano, alkoxycarbonyl, alkylcarbonyl, formyl, carbamoyl, mono- and dialkylaminocarbonyl, mono- and dialkylamino, alkylsulfinyl and alkylsulfonyl, where, in the case of radicals having carbon atoms, preference is given to those having 1 to 4 carbon atoms, in particular 1 or 2. Here, preference is generally given to substituents selected from the group consisting of halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano.

A heterocyclic radical or ring (heterocyclyl) can be saturated, unsaturated or heteroaromatic and unsubstituted or substituted, it can also be fused; it preferably contains one or more heteroatoms in the ring, preferably from the group consisting of N, O and S; it is preferably a saturated or unsaturated heterocyclyl radical having 3 to 7 ring atoms or a heteroaromatic radical having 5 or 6 ring atoms and contains 1, 2 or 3 heteroatoms. The heterocyclic radical can, for example, be a heteroaromatic radical or ring (heteroaryl), such as, for example, a mono-, bi- or polycyclic aromatic ring system in which at least 1 ring contains one or more heteroatoms, such as N, O and S, or is a partially or fully hydrogenated radical, for example pyrrolidyl, piperidyl, pyrazolyi, morpholinyl, indolyl, quinolinyl, pyrimidinyl, triazolyl, oxazolyl, pyridyl, pyrimidinyl, pyridazinyl, pyrazinyl, thiazolyl, pyrrolyl, oxazolinyl, isoxazolinyl, isoxazolyl, imidazolyl and benzoxazolyl. Suitable substituents for a substituted heterocyclic radical are the substituents mentioned below, and additionally also oxo. The oxo group may also be present on hetero ring atoms which can exist in different oxidation states, for example N and S.

Substituted radicals, such as substituted hydrocarbon-containing radicals, for example substituted alkyl, alkenyl, alkynyl, aryl, phenyl, or substituted heterocyclyl or heteroaryl, are, for example, substituted radicals derived from an unsubstituted skeleton, where the substituents are, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the saturated hydrocarbon-containing radicals mentioned, such as alkenyl, alkynyl, alkenyloxy, alkynyloxy, etc. In the case of radicals having carbon atoms, preference is given to those having 1 to 4 carbon atoms, in particular 1 or 2 carbon atoms. Preference is generally given to substituents from the group consisting of halogen, for example fluorine and chlorine, ($C_1$–$C_4$)-alkyl, preferably methyl or ethyl, ($C_1$–$C_4$)-haloalkyl, preferably trifluoromethyl, ($C_1$–$C_4$)-alkoxy, preferably methoxy or ethoxy, ($C_1$–$C_4$)-haloalkoxy, nitro and cyano. Particular preference is given here to the substituents methyl, methoxy, cyano and chlorine.

Unsubstituted or substituted phenyl is preferably phenyl which is unsubstituted or mono- or polysubstituted, preferably up to trisubstituted, by identical or different radicals selected from the group consisting of halogen, ($C_1$–$C_4$)-alkyl, ($C_1$–$C_4$)-alkoxy, ($C_1$–$C_4$)-haloalkyl, ($C_1$–$C_4$)-haloalkoxy, cyano and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-cyanophenyl.

An acyl radical is the radical of an organic acid which is formally formed by eliminating an OH group from the organic acid, for example the radical of a carboxylic acid and radicals of acids derived therefrom, such as thiocarboxylic acid, unsubstituted or N-substituted iminocarboxylic acids or the radicals of carbonic monoesters, unsubstituted or N-substituted carbaminic acids, sulfonic acids, sulfinic acids, phosphonic acids, phosphinic acids.

An acyl radical is preferably formyl or aliphatic acyl selected from the group consisting of CO—$R^x$, CS—$R^x$, CO—$OR^x$, CS—$OR^x$, CS—$SR^x$, $SOR^Y$ and $SO_2R^Y$, where $R^x$ and $R^Y$ are each a $C_1$–$C_{10}$-hydrocarbon radical, which is unsubstituted or substituted, or aminocarbonyl or aminosulfonyl, where the two last-mentioned radicals are unsubstituted, N-monosubstituted or N,N-disubstituted.

Acyl is, for example, formyl, haloalkylcarbonyl, alkylcarbonyl, such as ($C_1$–$C_4$)-alkylcarbonyl, phenylcarbonyl, where the phenyl ring may be substituted, for example as stated above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also provides all stereoisomers which are embraced by the formula (I), and mixtures thereof. Such compounds of the formula (I) contain one or more asymmetrically substituted carbon atoms or else double bonds, which are not specifically mentioned in the general formulae (I). The possible stereoisomers, defined by their specific spatial form, such as enantiomers, diastereomers, Z and E isomers, are all embraced by the formula (I) and can be obtained by customary methods from mixtures of the stereoisomers or else be prepared by stereoselective reactions in combination with the use of stereochemically pure starting materials.

The compounds of the formula (I) are capable of forming salts, for example those, in which a heteroatom such as N, O or S is present in protonated form. These salts are, for example salts of mineral acids, such as hydrochloric acid, hydrobromic acid and sulfuric acid, or else salts of organic acids, such as formic acid, acetic acid, oxalic acid, citric acid or aromatic carboxylic acids, such as benzoic acids.

If Y is a structural element O—$(CR^8R^9)_q$ or CO$(CR^8R^9)_q$, the radical B can be attached to O or CO or to $(CR^8R^9)_q$; preferably, B is attached to $(CR^8R^9)_q$.

Preference is given to compounds of the formula (I) and/or salts thereof where

A is a phenyl radical or an N- or S-containing heteroaromatic radical having 5 or 6 ring atoms, which radicals carry, on one of the two ring atoms next but one to the ring atom to which X is attached, a substituent selected from the group consisting of $CH_3$, $CH_2F$, $CHF_2$, $CF_3$, $OCH_3$, $OCH_2F$, $OCHF_2$, $OCF_3$ and CN, preferably from the group consisting of $CH_2F$, $CHF_2$, $CF_3$, $OCH_2F$, $OCHF_2$, $OCF_3$ and CN, particularly preferably from the group consisting of $CF_3$, $OCF_3$ and CN, and optionally a second substituent selected from the group consisting of halogen, CN, ($C_1$–$C_8$)-alkyl, ($C_1$–$C_8$)-alkoxy and ($C_1$–$C_8$)-alkylthio, where each of the three last-mentioned radicals is unsubstituted or substituted by one or more radicals selected from the group consisting of halogen, CN, ($C_1$–$C_8$)-alkoxy and ($C_1$–$C_8$)-alkylthio, for example ($C_1$–$C_8$)-haloalkyl, ($C_1$–$C_8$)-haloalkyloxy, ($C_1$–$C_8$)-haloalkylthio or ($C_1$–$C_8$)-alkoxy-($C_1$–$C_8$)-alkyloxy, X is O, S or $CH_2$, $R^1$ is hydroxyl, halogen, CN, NC, CHO, CO($C_1$–$C_8$)-alkyl or COO($C_1$–$C_8$)-alkyl, where the alkyl groups are unsubstituted or substituted, for example by one or more radicals selected from the group consisting of hydroxyl, halogen, CN, ($C_1$–$C_8$)-alkoxy, ($C_1$–$C_8$)-alkylthio, ($C_1$–$C_8$)-alkylsulfinyl, ($C_1$–$C_8$)-alkylsulfonyl and [($C_1$–$C_8$)-alkoxy]carbonyl, or $CONH_2$, $CSNH_2$, nitro, $SF_5$, ($C_1$–$C_8$)-alkyl, ($C_2$–$C_8$)-alkenyl or ($C_1$–$C_8$)-alkoxy, where the 3 last-mentioned radicals are unsubstituted or substituted, for example by one or more radicals selected from the group consisting of hydroxyl, halogen, CN, ($C_1$–$C_8$)-alkoxy and ($C_1$–$C_8$)-alkylthio, $R^2$ are identical or different radicals H, halogen, CN or ($C_1$–$C_8$)-alkyl, which is unsubstituted or substituted, for example by one or more radicals selected from the group consisting of hydroxyl, halogen, CN, ($C_1$–$C_8$)-alkoxy and ($C_1$–$C_8$)-alkylthio, Y is O—$(CR^8R^9)_q$, $S(O)_q$, NH, CO$(CR^8R^9)_q$ or $CR^8R^9$ and, if B is an unsubstituted or substituted aryl radical, an unsubstituted or substituted heterocyclyl radical, halogen or CN, Y may also be a bond, where $R^8$ and $R^9$ are identical or different radicals H, hydroxyl, halogen, CN, ($C_1$–$C_8$)-alkoxy or ($C_1$–$C_8$)-alkyl, where each of the two last-mentioned radicals is unsubstituted or substituted, for example substituted by one or more radicals selected from the group consisting of hydroxyl, halogen, CN, ($C_1$–$C_8$)-alkoxy and ($C_1$–$C_8$)-alkylthio, and q=0, 1 or 2, and B is an aryl radical, for example a phenyl radical, or a 5- or 6-membered heterocyclic radical, for example a 5- or 6-membered N- or S-containing heteroaromatic radical, where the radicals mentioned are unsubstituted or substituted by one or more radicals selected from the group consisting of hydroxyl, halogen, CN, ($C_1$–$C_8$)-alkyl, ($C_1$–$C_8$)-alkoxy, halo-($C_1$–$C_8$)-alkyl, halo-($C_1$–$C_8$)-alkyloxy, halo-($C_1$–$C_8$)-alkylthio and ($C_1$–$C_8$)-alkoxy-($C_1$–$C_8$)-alkoxy, or H, OH, halogen, CN, nitro, $SF_5$, ($C_1$–$C_8$)-alkyl, ($C_2$–$C_8$)-alkenyl or ($C_2$–$C_8$)-alkynyl, where the three last-mentioned radicals are unsubstituted or substituted, for example by one or more radicals selected from the group consisting of hydroxyl, halogen, CN, ($C_1$–$C_8$)-alkoxy, ($C_1$–$C_8$)-alkylthio, ($C_1$–$C_8$)-alkylsulfinyl, ($C_1$–$C_8$)-alkylsulfonyl, [($C_1$–$C_8$)-alkoxy]carbonyl, ($C_1$–$C_8$)-haloalkoxy and ($C_1$–$C_8$)-haloalkylthio and ($C_1$–$C_8$)-alkoxy-($C_1$–$C_8$)-alkoxy, or an acyl radical, for example [($C_1$–$C_8$)-alkyl]carbonyl, such as straight-chain or branched [($C_1$–$C_8$)-alkyl]carbonyl or [($C_3$–$C_8$)-cycloalkyl]carbonyl, ($C_6$–$C_{14}$)-arylcarbonyl, ($C_1$–$C_8$)-alkylsulfonyl or ($C_6$–$C_{14}$)-arylsulfonyl, where each of the radicals mentioned is unsubstituted or substituted, for example by one or more radicals selected from the group consisting of hydroxyl, halogen, CN, $(C_1-C_8)$-alkoxy, $(C_1-C_8)$-alkylthio, $(C_1-C_8$-alkylsulfinyl, $(C_1-C_8)$-alkylsulfonyl, $[(C_1-C_8)$-alkoxy]carbonyl, $(C_1-C_8)$-haloalkoxy and $(C_1-C_8)$-haloalkylthio, or $NR^{11}R^{12}$, where $R^{11},R^{12}$ independently of one another are identical or different radicals H, $(C_1-C_8)$-alkyl, $(C_2-C_8)$-alkenyl, $(C_7-C_{10})$-arylalkyl, $(C_7-C_{10})$-alkylaryl, $(C_6-C_{10})$-aryl or heteroaryl, where each of the six last-mentioned radicals is unsubstituted or substituted, for example by one or more radicals selected from the group consisting of hydroxyl, halogen, CN, $(C_1-C_8)$-alkoxy and $(C_1-C_8)$-alkylthio, or an acyl radical, for example $[(C_1-C_8)$-alkyl]carbonyl, such as straight-chain or branched $[(C_1-C_8)$-alkyl]-carbonyl or $[(C_3-C_6)$-cycloalkyl]carbonyl, $(C_6-C_{14})$-arylcarbonyl, $(C_6-C_{14})$-aryl-$(C_1-C_8)$-alkylcarbonyl, $(C_1-C_8)$-alkylsulfonyl or $(C_6-C_{14})$-arylsulfonyl, where each of the radicals mentioned is unsubstituted or substituted, for example substituted by one or more radicals selected from the group consisting of hydroxyl, halogen, $(C_1-C_8)$-alkoxy, $(C_1-C_8)$-alkylthio, $(C_1-C_8)$-alkylsulfinyl, $(C_1-C_8)$-alkylsulfonyl, $[(C_1-C_8)$-alkoxy]carbonyl, $(C_1-C_8)$-haloalkoxy, $(C_1-C_8)$-haloalkylthio and CN, or B is a group of the formula

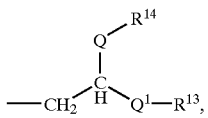

where $R^{13}$ is $(C_1-C_8)$-alkyl, which is unsubstituted or substituted, for example by one or more radicals selected from the group consisting of hydroxyl, halogen, CN, $(C_1-C_8)$-alkoxy and $(C_1-C_8)$-alkylthio, $R^{14}$ is $(C_1-C_8)$-alkyl, which is unsubstituted or substituted, for example by one or more radicals selected from the group consisting of hydroxyl, halogen, CN, $(C_1-C_8)$-alkoxy and $(C_1-C_8)$-alkylthio, or $R^{13}$ and $R^{14}$ together form a ring, Q=O or S, and $Q^1$=O or S.

Particular preference is given to compounds of the formula (I) and/or salts thereof where
A is a group of the formula (A')

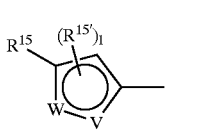

where $R^{15}$ is selected from the group consisting of $CH_3$, $CH_2F$, $CHF_2$, $CF_3$, $OCH_3$, $OCH_2F$, $OCHF_2$, $OCF_3$ and CN, preferably from the group consisting of $CH_2F$, $CHF_2$, $CF_3$, $OCH_2F$, $OCHF_2$, $OCF_3$ and CN, particularly preferably from the group consisting of $CF_3$, $OCF_3$ and CN, $R^{15'}$ is halogen, CN, $(C_1-C_8)$-alkyl, $(C_1-C_8)$-alkoxy or $(C_1-C_8)$-alkylthio, where each of the three last-mentioned radicals is unsubstituted or substituted by one or more radicals selected from the group consisting of halogen, CN, $(C_1-C_8)$-alkoxy and $(C_1-C_8)$-alkylthio, for example $(C_1-C_8)$-haloalkyl, $(C_1-C_8)$-haloalkyloxy, $(C_1-C_8)$-haloalkylthio or $(C_1-C_8)$-alkoxy-$(C_1-C_8)$-alkyloxy, l is zero or 1, V is CH or $N(C_1-C_8)$-alkyl, W is N, S, N—CH or CH—CH, X is O, S or $CH_2$, $R^1$ is hydroxyl, halogen, preferably fluorine, chlorine, bromine or iodine, CN, NC, CHO, $CONH_2$, $CSNH_2$, nitro, $(C_1-C_8)$-alkyl, $(C_2-C_8)$-alkenyl, $CO(C_1-C_8)$-alkyl, COO$(C_1-C_8)$-alkyl or $(C_1-C_8)$-alkoxy, where each of the five last-mentioned radicals is unsubstituted or substituted by one or more radicals selected from the group consisting of hydroxyl, halogen, CN, $(C_1-C_8)$-alkoxy and $(C_1-C_8)$-alkylthio, $R^2$ are identical or different radicals H, halogen, preferably fluorine or chlorine, or CN, Y is O—$(CR 8R)_q$, $S(O)_q$, NH, $CO(CR^8R^9)_q$ or $CR^8R^9$ and, if B is an unsubstituted or substituted aryl radical, an unsubstituted or substituted heterocyclyl radical, halogen or CN, Y may also be a bond, where $R^8$ and $R^9$ are identical or different radicals H, hydroxyl, halogen, CN, $(C_1-C_8)$-alkoxy or $(C_1-C_8)$-alkyl, where each of the two last-mentioned radicals is unsubstituted or substituted, for example by one or more radicals selected from the group consisting of hydroxyl, halogen, CN, $(C_1-C_8)$-alkoxy and $(C_1-C_8)$-alkylthio and q=0, 1 or 2, and B is an aryl radical, for example a phenyl radical, or a 5- or 6-membered heterocyclic radical, for example a 5- or 6-membered N- or S-containing heteroaromatic radical, where the radicals mentioned are unsubstituted or substituted by one or more radicals selected from the group consisting of hydroxyl, halogen, CN, $(C_1-C_8)$-alkyl, $(C_1-C_8)$-alkoxy, halo-$(C_1-C_8)$-alkyl, halo-$(C_1-C_8)$-alkyloxy, halo-$(C_1-C_8)$-alkylthio and $(C_1-C_8)$-alkoxy-$(C_1-C_8)$-alkoxy, H, OH, halogen, CN, nitro, $SF_5$, $(C_1-C_8)$-alkyl, $(C_2-C_8)$-alkenyl or $(C_2-C_8)$-alkynyl, where the three last-mentioned radicals are unsubstituted or substituted, for example by one or more radicals selected from the group consisting of hydroxyl, halogen, CN, $(C_1-C_8)$-alkoxy, $(C_1-C_8)$-alkylthio, $(C_1-C_8)$-alkylsulfinyl, $(C_1-C_8)$-alkylsulfonyl, $[(C_1-C_8)$-alkoxy]carbonyl, $(C_1-C_8)$-haloalkoxy, $(C_1-C_8)$-haloalkylthio and $(C_1-C_8)$-alkoxy-$(C_1-C_8)$-alkoxy, or an acyl radical, for example $[(C_1-C_8)$-alkyl]carbonyl, such as straight-chain or branched $[(C_1-C_8)$-alkyl]carbonyl or $[(C_3-C_6)$-cycloalkyl]carbonyl, $(C_6-C_{14})$-arylcarbonyl, $(C_1-C_8)$-alkylsulfonyl or $(C_6-C_{14})$-arylsulfonyl, where each of the radicals mentioned is unsubstituted or substituted, for example by one or more radicals selected from the group consisting of hydroxyl, halogen, CN, $(C_1-C_8)$-alkoxy, $(C_1-C_8)$-alkylthio, $(C_1-C_8)$-alkylsulfinyl, $(C_1-C_8)$-alkylsulfonyl, $[(C_1-C_8)$-alkoxy]carbonyl, $(C_1-C_8)$-haloalkoxy and $(C_1-C_8)$-haloalkylthio, or $NHR^{12}$, where $R^{12}$ is H, $(C_1-C_8)$-alkyl, $(C_2-C_8)$-alkenyl, $(C_7-C_{10})$-arylalkyl, $(C_7-C_{10})$-alkylaryl, $(C_6-C_{10})$-aryl or heteroaryl, where each of the six last-mentioned radicals is unsubstituted or substituted, for example by one or more radicals selected from the group consisting of hydroxyl, halogen, CN, $(C_1-C_8)$-alkoxy and $(C_1-C_8)$-alkylthio, or an acyl radical, for example $[(C_1-C_8)$-alkyl]carbonyl, such as straight-chain or branched [(C$_1$–C$_8$)-alkyl]carbonyl or [(C$_3$–C$_6$)-cycloalkyl]carbonyl, (C$_6$–C$_{14}$)-arylcarbonyl, (C$_6$–C$_{14}$)-aryl-(C$_1$–C$_8$)-alkylcarbonyl, (C$_1$–C$_8$)-alkylsulfonyl or (C$_6$–C$_{14}$)-arylsulfonyl, where each of the radicals mentioned is unsubstituted or substituted, for example by one or more radicals selected from the group consisting of hydroxyl, halogen, (C$_1$–C$_8$)-alkoxy, (C$_1$–C$_8$)-alkylthio, (C$_1$–C$_8$)-alkylsulfinyl, (C$_1$–C$_8$)-alkylsulfonyl, [(C$_1$–C$_8$)-alkoxy]carbonyl, (C$_1$–C$_8$)-haloalkoxy, (C$_1$–C$_8$)-haloalkylthio and CN, or B is a group of the formula

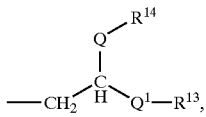

where R$^{13}$ is (C$_1$–C$_8$)-alkyl, which is unsubstituted or substituted, for example by one or more radicals selected from the group consisting of hydroxyl, halogen, CN, (C$_1$–C$_8$)-alkoxy and (C$_1$–C$_8$)-alkylthio, R$^{14}$ is (C$_1$–C$_8$)-alkyl, which is unsubstituted or substituted, for example by one or more radicals selected from the group consisting of hydroxyl, halogen, CN, (C$_1$–C$_8$)-alkoxy and (C$_1$–C$_8$)-alkylthio, or R$^{13}$ and R$^{14}$ together form a ring, Q=O or S, and Q$^1$=O or S.

Particular preference is given to compounds of the formula (I) and/or salts thereof where A is a substituted phenyl, pyridyl, thienyl or pyrazolyl radical of the formulae below

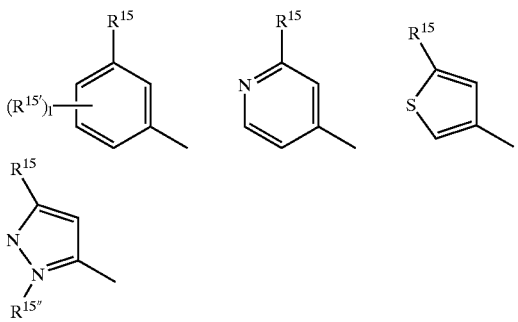

where

R$^{15}$ is selected from the group consisting of CH$_3$, CH$_2$F, CHF$_2$, CF$_3$, OCH$_3$, OCH$_2$F, OCHF$_2$, OCF$_3$ and CN, preferably from the group consisting of CH$_2$F, CHF$_2$, CF$_3$, OCH$_2$F, OCHF$_2$, OCF$_3$ and CN, particularly preferably from the group consisting of CF$_3$, OCF$_3$ and CN, very particularly preferably CF$_3$ or CN, R$^{15'}$ is a (C$_1$–C$_8$)-alkyl group, such as methyl, halogen or CN, R$^{15''}$ is a (C$_1$–C$_8$)-alkyl group, such as methyl, and l is zero or 1, preferably A is a radical of the formulae

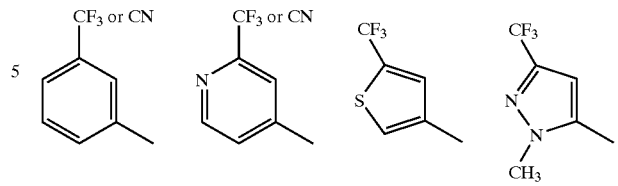

The present invention also provides methods for preparing the compounds of the formula (I) and/or salts thereof. The compounds of the formula (I) according to the invention can be prepared by known methods. Of particular interest are, for example, the following syntheses:

If, for example, a compound of the formula (II) is reacted with nucleophiles of the type A-X—H and with nucleophiles of the type B—Y—H, the course of the reaction of the process (a1) according to the invention can be described by the formula scheme below:

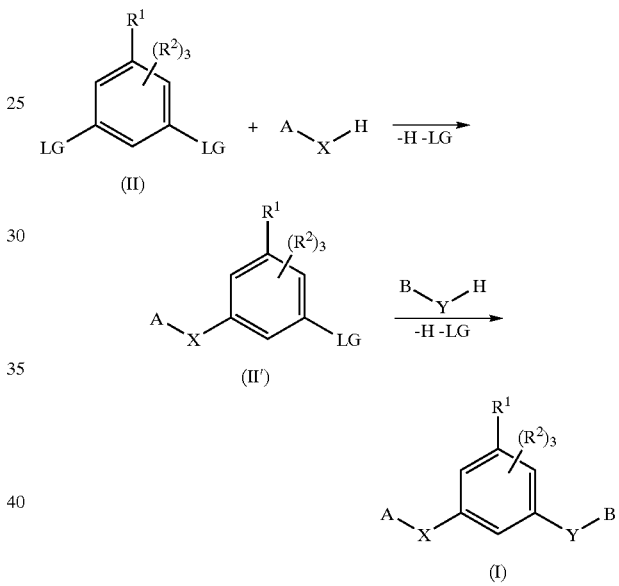

The formula (II) provides a general definition of the phenyl derivatives used as starting materials in the process (a1) according to the invention for preparing compounds of the formula (I). In the formula (II), R$^1$ and R$^2$ are as defined above in formula (I), including the given preferred ranges, and LG are identical or different leaving groups, such as halogen or pseudohalogen, for example CN.

The formulae A-X—H and B—Y—H provide general definitions of the nucleophiles used as starting materials in the process (a1) according to the invention for preparing compounds of the formula (I), where A, X, B and Y have those meanings which have been mentioned above, in connection with the description of the compounds of the formula (I) according to the invention, including the given preferred ranges, and H is hydrogen. The starting materials of the formula (II), the formula A-X—H and the formula B—Y—H are known and/or commercially available (see, for example, Chem. Het. Compounds 33, 1997, 995–996; Synthesis (2000) pp. 1078–1080). The conversion into compounds of the formula (I) can be carried out according to known processes (see, for example, J.Med.Chem. 29 (1986) 887–889; J.Med.Chem. 39 (1996) 347–349). The reaction can be carried out in the absence or presence of a solvent which promotes the reaction or, at least, has no adverse effect on the reaction. Preference is given to polar, aprotic or protic solvents, such as N,N-dimethylformamide, N,N-dimethylacetamide, dimethyl sulfoxide, sulfolane, acetonitrile, methyl ethyl ketone or ethers, such as dioxane or tetrahydrofuran, or alcohols or water or mixtures of the solvents mentioned. The reactions are carried out at temperatures between room temperature and the reflux temperature of the reaction mixture, preferably at elevated temperature, in particular at reflux temperature. The reactions can be carried out in the presence of a base, such as alkali metal hydroxide, alkaline earth metal hydroxide, alkali metal alkoxide, alkali metal halide, alkali metal hydride or an organic base; potassium hydroxide, sodium hydroxide, sodium ethoxide, sodium methoxide, cesium fluoride, triethylamine and sodium hydroxide may be mentioned by way of example. The reaction can be carried out as a one-pot reaction or in separate steps.

If, for example, a compound of the formula (II) is reacted with nucleophiles of the type B—Y—H and with nucleophiles of the type A-X—H, the course of the reaction of the process (a2) according to the invention can be described by the formula scheme below:

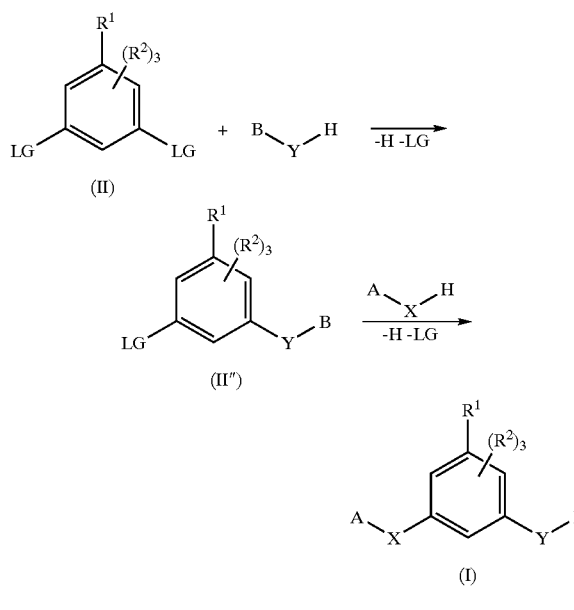

The formula (II) provides a general definition of the phenyl derivatives used as starting materials in the process (a2) according to the invention for preparing compounds of the formula (I). In the formula (II), $R^1$ and $R^2$ are as defined above in formula (I), including the given preferred ranges, and LG are identical or different leaving groups, such as halogen or pseudohalogen, for example CN. The formulae A-X—H and B—Y—H provide general definitions of the nucleophiles used as starting materials in the process (a2) according to the invention for preparing compounds of the formula (I), where A, X, B and Y preferably have those meanings which have been mentioned above, in connection with the description of the compounds of the formula (I) according to the invention, including the given preferred ranges, and H is hydrogen. The starting materials of the formula (II), the formula A-X—H and the formula B—Y—H are known and/or commercially available (see, for example, Chem. Het. Compounds 33, 1997, 995–996; Synthesis (2000) pp. 1078–1080). The conversion into compounds of the formula (I) can be carried out according to known processes (see, for example, J.Med.Chem. 29 (1986) 887–889; J.Med.Chem. 39 (1996) 347–349). The reaction can be carried out in the absence or presence of a solvent which promotes the reaction or, at least, has no adverse effect on the reaction. Preference is given to polar, aprotic or protic solvents, such as N,N-dimethylformamide, N,N-dimethylacetamide, dimethyl sulfoxide, sulfolane, acetonitrile, methyl ethyl ketone or ethers, such as dioxane or tetrahydrofuran, or alcohols or water or mixtures of the solvents mentioned. The reactions are carried out at temperatures between room temperature and the reflux temperature of the reaction mixture, preferably at elevated temperature, in particular at reflux temperature. The reactions can be carried out in the presence of a base, such as alkali metal hydroxide, alkaline earth metal hydroxide, alkali metal alkoxide, alkali metal halide, alkali metal hydride or an organic base; potassium hydroxide, sodium hydroxide, sodium ethoxide, sodium methoxide, cesium fluoride, triethylamine and sodium hydroxide may be mentioned by way of example. The reaction can be carried out as a one-pot reaction or in separate steps.

If, for example, a compound of the formula (III) or (III') is reacted with boronic acid derivatives of the type (IV) or (IV'), the course of the reaction in the process (b) according to the invention can be described by the following formula scheme of a coupling reaction:

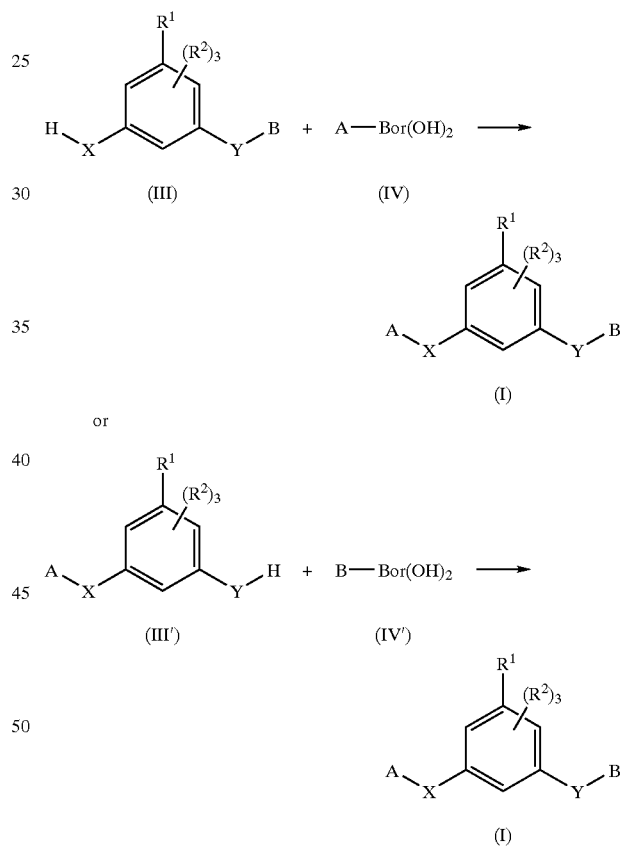

The formulae (III) and (III') provide general definitions of the phenyl derivatives used as starting materials in the process (b) according to the invention for preparing compounds of the formula (I). In the formulae (III) and (III'), $R^1$, $R^2$, X, Y, A and B have the meanings given above in formula (I), including the given preferred ranges. The boronic acid derivatives of the formula (IV) and (IV') used as starting materials in the process (b) according to the invention for preparing compounds of the formula (I) are characterized by the formulae A-Bor(OH)$_2$ and B-Bor(OH)$_2$, respectively, where A and B have the meanings given above in connection with the description of the compounds of the formula (I)

according to the invention, including the given preferred ranges. The coupling reaction is usually carried out in the presence of a transition metal complex, as described, for example, in Tetrahedron Letters 39 (1998) 2933ff. Preferred transition metals are Cu, Pd or Ni. The reaction can be carried out in the absence or presence of a solvent which promotes the reaction or, at least, has no adverse effect on the reaction. The starting materials of the formulae (III) and (III') and of the formulae (IV) and (IV') are known and/or commercially available and/or can be prepared by known processes (see, for example, J.Organomet.Chem. 309 (1986) 241–246; J.Amer.Chem.Soc. 112 (1990) 8024–8034; EP 1108720). The reaction can be carried out in the absence or presence of a solvent which promotes the reaction or, at least, has no adverse effect on the reaction. Preference is given to polar or nonpolar, aprotic or protic solvents, such as N,N-dimethylformamide, N,N-dimethylacetamide, dimethyl sulfoxide, sulfolane, dichloromethane, dichloroethane, acetonitrile or ethers, such as dioxane or tetrahydrofuran, or mixtures of the solvents mentioned. The reactions are carried out at temperatures between room temperature and the reflux temperature of the reaction mixture, preferably at elevated temperature, in particular at reflux temperature. The reactions can be carried out in the presence of an inorganic or organic base; triethylamine, pyridine or thallium hydroxide may be mentioned by way of example. The reactions can be carried out in the presence or absence of molecular sieves.

If, for example, a boronic acid derivatives of the formula (V) or (V') is reacted with nucleophiles of the type A-X—H or B—Y—H, the course of the reaction in the process (c) according to the invention can be described by the following formula scheme of a coupling reaction:

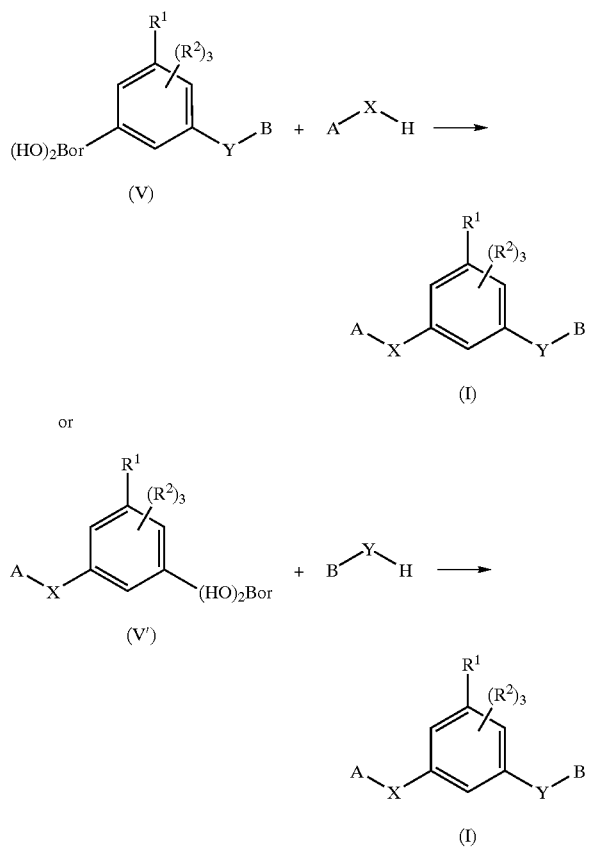

process (c) according to the invention for preparing 12 compounds of the formula (I). In the formulae (V) and (V'), $R^1, R^2$, X, Y, A and B have the meanings given above in formula (I), including the given preferred ranges. The compounds of the formulae A-X—H and B—Y—H used as starting materials in the process (c) according to the invention for preparing compounds of the formula (I) are known and/or commercially available, where A, B, X and Y have the meanings given above in connection with the description of the compounds of the formula (I) according to the invention, including the given preferred ranges, and H is hydrogen. The reaction is usually carried out in the presence of a transition metal complex, as described, for example, in Tetrahedron Letters 39 (1998) 2933ff. Preferred transition metals are Cu, Pd or Ni. The reaction can be carried out in the absence or presence of a solvent which promotes the reaction or, at least, has no adverse effect on the reaction. The starting materials of the formulae (V) and (V') are known and/or commercially available and/or can be prepared by known processes (see, for example, EP 1108720 and J.Organomet.Chem. 309 (1986) 241–246). The reaction can be carried out in the absence or presence of a solvent which promotes the reaction or, at least, has no adverse effect on the reaction. Preference is given to polar or nonpolar, aprotic or protic solvents, such as N,N-dimethylformamide, N,N-dimethylacetamide, dimethyl sulfoxide, sulfolane, dichloromethane, dichloroethane, acetonitrile or ethers, such as dioxane or tetrahydrofuran, or mixtures of the solvents mentioned. The reactions are carried out at temperatures between room temperature and the reflux temperature of the reaction mixture, preferably at elevated temperature, in particular at reflux temperature. The reactions can be carried out in the presence of an inorganic or organic base; triethylamine, pyridine or thallium hydroxide may be mentioned by way of example. The reactions can be carried out in the presence or absence of molecular sieves.

If, for example, a compound of the formula (VI) is reduced and acylated, the course of the reaction giving compounds of the formula (I) where $Y=CH_2$ and B=NH-acyl in the process (d) according to the invention can be described by the formula scheme below:

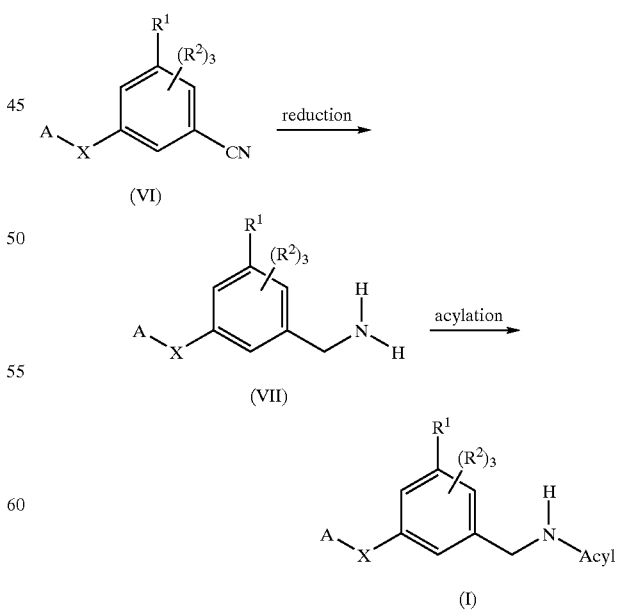

The formulae (V) and (V') provide general definitions of the phenyl derivatives used as starting materials in the The formula (VI) provides a general definition of the benzonitrile derivatives used as starting materials in the process (d) according to the invention for preparing compounds of the formula (I). In the formula (VI), $R^1$, $R^2$, A and X have the meanings given above in the formula (I), including the given preferred ranges. The starting materials of the formula (VI) are known and/or commercially available and/or can be prepared by known processes (see, for example, Russ.J.Org.Chem. 32 (1996) 1505–1509). The reduction of nitriles to amines has been described extensively in the literature (see, for example, Eugen Müller, Methoden der organischen Chemie [Methods of Organic Chemistry] (Houben-Weyl) Volume XI/1, Nitrogen compounds II, p. 343 ff., Georg Thieme Verlag, Stuttgart 1957). Suitable are, inter alia, noble-metal-catalyzed hydrogenations, palladium- and platinum-catalyzed reactions being of particular interest; however, reductions using Raney-nickel are also possible. Furthermore possible are reductions by complex hydride reagents, such as, for example, lithium aluminum hydride, borane-THF complex, superhydride or diborane. The reduction can be carried out at temperatures of 0–250° C. and at pressures of 1–100 bar.

Compounds of the formula (VII) can be converted by reaction with acylating agents, such as acid halides, isocyanates, carbamoyl chlorides, chloroformic esters, sulfonyl chlorides, sulfamoyl chlorides, sulfenyl chlorides, isothiocyanates, into compounds of the formula (I) where $Y=CH_2$ and B=NH-acyl and A, X, $R^1$ and $R^2$ have the meanings given in formula (I). General and special chemical methods of acylation are described, for example, in: Jerry March, Advanced Organic Chemistry (Reaction, Mechanisms and Structure) $4^{th}$ Edition, John Wiley & Sons, New York, 1992.

If, for example, a compound of the formula (VI) is hydrolyzed and reacted with an amine $NH_2$—$R^{12}$ the course of the reaction giving compounds of the formula (1) where Y=CO and B=$NHR^{12}$ in the process (e) according to the invention can be described by the formula scheme below:

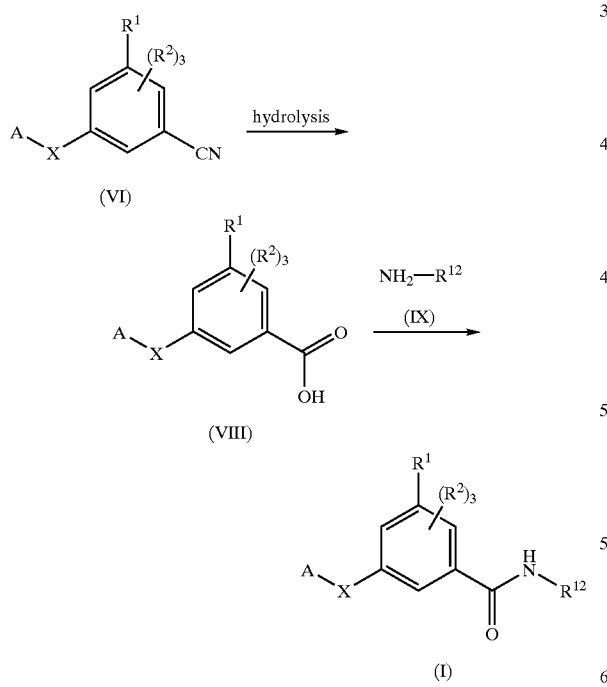

The formula (VI) provides a general definition of the benzonitrile derivatives used as starting materials in the process (e) according to the invention for preparing compounds of the formula (I). In the formula (VI), $R^1$, $R^2$, A and X have the meanings given above in formula (I), including the given preferred ranges. The compounds of the formula (VI) can be prepared by known processes (see, for example, Russ. J. Org. Chem. 32, 1996, pp.1505–1509). The hydrolysis of nitriles to carboxylic acids has been described extensively in the literature (see, for example, J. Am. Chem. Soc. 107 (1985) 7967ff., J. Am. Chem. Soc. 78 (1956) 450ff., J. Org. Chem. 51 (1986) 4169ff., Org. Synth. Collect. Vol. 1–4). The reaction of the compounds of the formulae (VIII) and (IX) is preferably carried out in an inert organic solvent, such as tetrahydrofuran (THF), dichloromethane, 1,2-dichloroethane, chloroform or dimethylformamide, at temperatures between –10° C. and the boiling point of the solvent, preferably of from 0° C. to 60° C., where in the first reaction step the carboxylic acid of the formula (VII) is converted into the corresponding acid halide. The acid halide is prepared in accordance with processes known from the literature, using, for example, oxalyl chloride, thionyl chloride, phosphorus pentachloride, phosphorus oxychloride or phosphorus tribromide in the presence of catalytic or equimolar amounts of dimethylformamide for the halogenation. Subsequently, the product is reacted with the amine of the formula (IX) where $R^{12}$ is as defined in formula (I), preferably in the presence of bases or basic catalysts. Suitable bases or basic catalysts are alkali metal carbonates, alkali metal alkoxides, alkaline earth metal carbonates, alkaline earth metal alkoxides or organic bases, such as triethylamine, 1,8-diazabicyclo[5.4.0]undec-7-ene (DBU) or 4-dimethylaminopyridine (DMAP). The base in question is, for example, employed in a range of from 0.1 to 3 molar equivalents, based on the compound of the formula (III). The compound of the formula (IX) can, based on the compound of the formula (VIII), be employed, for example, in equimolar amounts or in an excess of up to 2 molar equivalents. The corresponding processes are known in principle from the literature (compare: Organikum, VEB Deutscher Verlag der Wissenschaften, Berlin 1988, Jerry March, Advanced Organic Chemistry (Reaction, Mechanisms and Structure) 4th Edition, John Wiley & Sons, New York, 1992).

If, for example, a compound of the formula (VI) is reacted with an organometallic compound (for example Grignard reagents, organozinc compounds or organolithium compounds), the course of the reaction giving compounds of the formula (I) where Y=CO in the process (f) according to the invention can be described by the formula scheme below:

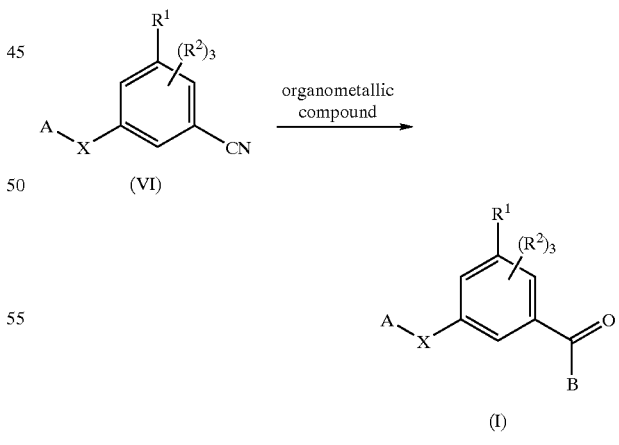

The formula (VI) provides a general definition of the benzonitrile derivatives used as starting materials in the process (f) according to the invention for preparing compounds of the formula (I). In the formula (VI), $R^1$, $R^2$, A and X have the meanings given above in formula (I), including the given preferred ranges. The organometallic compounds used, for example of the formula B—Mg—Br, B—Li or B—Zn—Cl, are commercially available and/or obtainable by known processes (see, for example, M. Schlosser: Organometallics in Synthesis, John Wiley & Sons 1994). The compounds of the formula (VI) can be prepared by known processes (see, for example, Russ. J. Org. Chem. 32, 1996, pp.1505–1509). The conversion of benzonitriles, for example into benzophenone derivatives, has been described extensively in the literature (see, for example, Tetrahedron Lett. 2000, 41 (6), 937–939; J. Org. Chem. 2000, 65 (12), 3861–3863; Synth. Commun. 1998, 28 (21), 4067–4075; J. Med. Chem. 1998, 41 (22), 4400–4407; Synth. Commun. 1996, 26 (4), 721–727; Synthesis (1991) 1, 56–58; Angew. Chem., Int. Ed. Engl. 1965, 4, 1077; J. Am. Chem. Soc. 1970, 92, 336). The reaction of compounds of the formula (VI) with the organometallic compounds is preferably carried out in an inert organic solvent, such as tetrahydrofuran (THF), dioxane, diethyl ether or diisopropyl ether, at temperatures between −78° C. and the boiling point of the solvent, preferably at from 0° C. to 120° C. The reaction can be carried out in the absence or presence of a catalyst, such as, for example, LiI, CuI or CuBr.

Collections of compounds of the formula (I) and salts thereof which can be synthesized by the abovementioned schemes may also be prepared in a parallel manner and this may be effected manually or in a semiautomated or fully automated manner. In this case, it is possible, for example, to automate the procedure of the reaction, the work-up or the purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A number of commercially available apparatuses as they are offered by, for example, Stem Corporation, Woodrolfe Road, Tollesbury, Essex, UK, H+P Labortechnik GmbH, Bruckmannring 28, 85764 Oberschleißheim, Germany or Radleys, Shirehill, Saffron Walden, Essex, CB11 3AZ, UK may be used for the parallel procedure of the reaction and work-up. For the parallel purification of compounds of the formula (I) and their salts, or of intermediates obtained during the preparation, use may be made, inter alia, of chromatography apparatuses, for example those from ISCO, Inc., 4700 Superior Street, Lincoln, Nebr. 68504, USA.

The apparatuses mentioned lead to a modular procedure in which the individual process steps are automated, but manual operations have to be performed between the process steps. This can be avoided by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) and/or salts thereof may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Verlag Academic Press, 1998. The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation methods described here give compounds of the formula (I) and/or their salts in the form of collections of substances known as libraries. The present invention also relates to libraries which contain at least two compounds of the formula (I) and/or their salts.

The compounds of the formula (I) according to the invention and/or their salts, hereinbelow together referred to as compounds according to the invention, have excellent herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is possible for the substances to be applied pre-sowing, pre-emergence or post-emergence, for example to the plants, to plant seeds or to the area in which the plants grow. Specifically, examples may be mentioned of some representatives of the monocotyledonous and dicotyledonous weed flora which can be controlled by the compounds according to the invention, without these being a restriction to certain species.

Examples of weed species on which the active compounds act efficiently are, from amongst the monocotyledons, Avena, Lolium, Alopecurus, Phalaris, Echinochloa, Digitaria, Setaria and also Bromus species and Cyperus species from the annual sector and from amongst the perennial species Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, lpomoea, Matricaria, Abutilon and Sida from amongst the annuals, and Convolvulus, Cirsium, Rumex and Artemisia in the case of the perennial weeds.

The active ingredients according to the invention also effect outstanding control of harmful plants which occur under the specific conditions of rice growing such as, for example, Echinochloa, Sagittaria, Alisma, Eleocharis, Scirpus and Cyperus.

If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledonous weeds, crop plants of economically important crops, for example, dicotyledonous crops such as soybean, cotton, oilseed rape, sugar beet, in particular soybean or gramineous crops such as wheat, barley, oats, rye, rice or corn, are not damaged at all, or only to a negligible extent. For these reasons, the present compounds are highly suitable for selectively controlling undesired plant growth (e.g. weeds) in plantings for agricultural use or in plantings of ornamentals.

In addition, the substances according to the invention have outstanding growth-regulating properties in crop plants. They engage in the plant metabolism in a regulating manner and can thus be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced hereby, or prevented completely.

Owing to their herbicidal and plant growth-regulatory properties, the active compounds according to the invention can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested product are known.

The use of the compounds according to the invention in economically important transgenic crops of useful and ornamental plants, for example of cereals, such as wheat, barley, rye, oats, millet, rice, maniok and corn, or else in crops of sugar beet, cotton, soybean, oilseed rape, potato, tomato, pea and other vegetable species is preferred.

The compounds according to the invention can preferably be used as herbicides in crops of useful plants which are resistant or which have been made resistant by genetic engineering toward the phytotoxic effects of the herbicides.

Conventional ways of preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827 and WO 91/19806), transgenic crop plants which are resistant to certain herbicides of the glufosinate—(cf., for example, EP-A 0 242 236, EP-A 0 242 246) or glyphosate-type (WO 92/00377), or of the sulfonylurea-type (EP-A 0 257 993, U.S. Pat. No. 5,013,659), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423–431).

In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end, it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical. When expressing nucleic acid molecules in plants, the synthesized protein can be localized in any desired compartment of the plant cell. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated to whole plants using known techniques. The transgenic plants can in principle be plants of any desired plant species, i.e. both monocotyledonous and dicotyledonous plants.

In this manner, it is possible to obtain transgenic plants which have modified properties by overexpression, suppression or inhibition of homologous (=natural) genes or gene sequences or by expression of heterologous (=foreign) genes or gene sequences.

The compounds according to the invention can preferably be used in transgenic crops which are resistant to herbicides selected from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants.

The invention therefore also provides for the use of the compounds according to the invention as herbicides for controlling harmful plants in transgenic crop plants.

The compounds according to the invention can be applied in various customary formulations, for example in the form of wettable powders, emulsifiable concentrates, sprayable solutions, dusts or granules. The invention therefore also provides herbicidal and plant-growth-regulating compositions comprising the compounds according to the invention.

The compounds according to the invention can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes.

These individual formulation types are known in principle and are described, for example, in Winnacker-Küchler, "Chemische Technologie" [Chemical Technology], Volume 7, C. Hauser Verlag Munich, 4th edition 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and other additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th edition 1986.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th ed., McGraw-Hill, New York 1973, pp. 8–57.

For further details on the formulation of crop protection products, see for example G. C. Klingman, "Weed Control as a Science", John Wiley and Sons., Inc., New York, 1961, pages 81–96 and J. D. Freyer, S. A. Evans, "Weed Control Handbook", 5th ed., Blackwell Scientific Publications, Oxford, 1968, pages 101–103.

The agrochemical formulations generally contain from 0.1 to 99% by weight, in particular from 0.1 to 95% by weight, of active compound of the formula (I) and/or their salts.

In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules, the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Suitable active compounds which can be combined with the active compounds according to the invention in mixed formulations or in a tank mix are, for example, known active compounds, such as herbicides, insecticides, fungicides or safeners, as described, for example, in Weed Research 26, (1986) 441–445, or "The Pesticide Manual", 12th edition, The British Crop Protection Council and the Royal Soc. of Chemistry, 2000 and in the literature cited therein. For example, the following active compounds may be mentioned as herbicides which are known and which can be combined with the compounds according to the invention (note: the compounds are either referred to by the "common name" in accordance with the International Organization for Standardization (ISO) or by the chemical name, if appropriate together with a customary code number):

acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azafenidin; azimsulfuron (DPX-A8947); aziprotryn; barban; BAS 516H, i.e. 5-fluoro-2-phenyl-4H-3,1-benzoxazin-4-one; BAS 620H; BAS65400H; BAY FOE 5043; benazolin; benfluralin; benfuresate; bensulfuron-methyl; bensulide; bentazone; benzofenap; benzofluor; benzoylprop-ethyl; benzthiazuron; bialaphos; bifenox; bispyribac-Na; bromacil; bromobutide; bromofenoxim; bromoxynil; bromuron; buminafos; busoxinone; butachlor; butamifos; butenachlor; buthidazole; butralin; butroxydim; butylate; cafenstrole (CH-900); caloxydim; carbetamide; cafentrazone-ethyl; CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cloransulam-methyl; cumyluron (JC 940); cyanazine; cycloate; cyclosulfamuron (AC 104); cycloxydim; cycluron; cyhalofop and its ester derivatives (for example the butyl ester, DEH-1 12); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diclosulam, i.e. N-(2,6-dichlorophenyl)-5-ethoxy-7-fluoro-[1,2,4]triazolo[1,5-c]-pyrimidine-2-sulfonamide; diethatyl; difenoxuron; difenzoquat; diflufenican; diflufenzopyr (BAS 654 00H); dimefuron; dimethachlor; dimethametryn; dimethenamid (SAN-582H); dimethazone; clomazone; dimethipin; dimetrasulfuron; dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]-phenyl]ethanesulfonamide; ethoxyfen and its esters (for example the ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters for example fluazifop-butyl and fluazifop-P-butyl; fluchloralin; flumetsulam; flumeturon; flumiclorac and its esters (for example flumiclorac-pentyl, S-23031); flumioxazin (S-482); flumipropyn; flupoxam (KNW-739); fluorodifen; fluoroglycofen-ethyl; flupropacil (UBIC-4243); flupyrsulfuron-methyl-sodium; fluridone; flurochloridone; fluroxypyr; flurtamone; fluthiacet-methyl; fomesafen; foramsulfuron and its salts such as the sodium salt; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox; imazapyr; imazaquin and salts such as the ammonium salt; imazethamethapyr; imazethapyr; imazosulfuron; indanofan (MK-243); iodosulfuron-methyl and its salts, such as the sodium salt; ioxynil; isocarbamid; isopropalin; isoproturon; isouron; isoxaben; isoxaflutole; isoxapyrifop; karbutilate; lactofen; lenacil; linuron; MCPA; MCPB; mecoprop; mefenacet; mefluidid; mesosulfuran-methyl and its salts such as the sodium salt; metamitron; metazachlor; methabenzthiazuron; metham; methazole; methoxyphenone; methyldymron; metobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazone; oxasulfuron; oxaziclomefone (MY-100); oxyfluorfen; paraquat; pebulate; pendimethalin; pentoxazone (KPP-314); perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyroflufen-ethyl; pyrazolinate; pyrazon; pyrazosulfuron-ethyl; pyrazoxyfen; pyribenzoxim (LGC-40836); pyributicarb; pyridate; pyriminobac-methyl; pyrithiobac (KIH-2031); pyroxofop and its esters (for example the propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazurone; sulfometuron-methyl; sulfosate (ICI-A0224); sulfosulfuron; TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thifensulfuron-methyl; thiobencarb; tiocarbazil; tralkoxydim; tri-allate; triasulfuron; triaziflam; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; JTC-101; UBH-509; D-489; LS 82-556; KPP-300; NC-324; NC-330; KH-218; DPX—N8189; SC-0774; DOWCO-535; DK-8910; V-53482; PP-600; MBH-001; KIH-9201; ET-751; KIH-6127 and KIH-2023.

The compounds according to the invention can also be used in combination with one or more compounds which act as safeners. For use, the formulations which are present in commercially available form are, if appropriate, diluted in the customary manner, for example using water in the case of wettable powders, emulsifiable concentrates, dispersions and water-dispersible granules. Preparations in the form of dusts, granules for soil application or broadcasting and sprayable solutions are usually not further diluted with other inert substances prior to use.

The application rate of the compounds according to the invention required varies with the external conditions, such as temperature, humidity, the nature of the herbicide used. It can vary within wide limits, for example between 0.001 and 10.0 kg/ha or more of active substance, but it is preferably between 0.005 and 5 kg/ha.

EXAMPLES

A. Chemical Examples

| Abbreviations: | The percentages and ratios are based on weight, unless specified in more detail.<br>h = hour(s) |
|---|---|

1. 3,5-Bis-(1-methyl-3-trifluoromethylpyrazol-5-yloxy)benzonitrile

Under an atmosphere of nitrogen, 2.00 g (14.4 mmol) of 3,5-difluorobenzonitrile were initially charged in 15 ml of sulfolane, and 4.77 g (34.5 mmol) of potassium carbonate were added a little at a time at room temperature. 5.25 g (31.60 mmol) of 1-methyl-3-(trifluoromethyl)-2-pyrazol-2-one were then added, the mixture was heated at 150° C. for 10 h and cooled to room temperature, water and ethyl acetate were added to the reaction solution and the solution was stirred for a number of minutes. The phases were separated and the organic phase was washed repeatedly with water and then with sodium hydroxide solution and finally with saturated sodium chloride solution and then dried over magnesium sulfate, filtered and concentrated. Column chromatography of the crude product gave 3,5-bis-(1-methyl-3-trifluoromethylpyrazol-5-yloxy)benzonitrile in the form of white crystals.

Yield: 1.19 g (19% of theory); melting point: 139° C.

2. 3-Fluoro-5-(1-methyl-3-trifluoromethylpyrazol-5-yloxy)benzonitrile

Under an atmosphere of nitrogen, 5.00 g (35.9 mmol) of 3,5-difluorobenzonitrile were initially charged in 60 ml of N,N-dimethylformamide, and 6.46 g (46.7 mmol) of potassium carbonate and 6.57 g (39.5 mmol) of 1-methyl-3-(trifluoromethyl)-2-pyrazol-2-one were added at room temperature. The mixture was heated at 150° C. for 2 h and cooled to room temperature, and water was added to the reaction solution. The solution was extracted twice with heptane/ethyl acetate (1:1) and twice with ethyl acetate. The combined phases were washed with water and then dried over magnesium sulfate, filtered and concentrated. Column chromatography of the crude product gave 4.19 g of 3-fluoro-5-(1-methyl-3-trifluoromethylpyrazol-5-yloxy)-benzonitrile in the form of white crystals and, as a by-product, 2.8 g of 3,5-bis-(1-methyl-3-trifluoromethylpyrazol-5-yloxy)benzonitrile in the form of white crystals.

Yield: 4.19 g (39% of theory); melting point: 84° C.

3. 3,5-Bis-(2-trifluoromethylpyridin-4-yloxy)benzonitrile

Under an atmosphere of nitrogen, 0.556 g (4.0 mmol) of 3,5-difluorobenzonitrile was initially charged in 10 ml of N,N-dimethylacetamide, and 1.22 g (8.8 mmol) of potassium carbonate were added a little at a time at room temperature. 1.305 g (8.00 mmol) of 2-(trifluoromethyl)pyridin-4-ol were then added and the mixture was heated at 150° C. for 30 h and cooled to room temperature, water and ethyl acetate/heptane (1:1) were added to the reaction solution and the solution was stirred for a number of minutes. The phases were separated and the organic phase was washed repeatedly with water and finally with saturated sodium chloride solution and then dried over sodium sulfate, filtered and concentrated. HPLC of the crude product gave 3,5-bis-(2-trifluoromethylpyridin-4-yloxy)benzonitrile in the form of white crystals.

Yield: 0.153 g (9% of theory); $^1$H NMR (CDCl$_3$/TMS): δ (ppm)=7.08 (dd, 2H, pyridine C—H), 7.13 (t, 1H, phenyl C—H), 7.30 (d, 2H, pyridine C—H), 7.34 (d, 2H, phenyl C—H), 8.70 (d, 2H, pyridine C—H).

4. 3,5-Bis-(1-methyl-3-trifluoromethylpyrazol-5-yloxy)phenyl-1-carboxamide

Under an atmosphere of nitrogen, 500 mg (1.16 mmol) of 3,5-bis-(1-methyl-3-trifluoromethylpyrazol-5-yloxy)benzonitrile were initially charged in 1.5 ml of dioxane, and 64 mg (0.5 mmol) of potassium carbonate were added at room temperature. At 10–15° C., 0.5 ml of a 30% strength solution of hydrogen peroxide in water was then added, and the mixture was stirred at room temperature for 1.5 h. For work-up, 10 ml of water were added, and the resulting precipitate was filtered off. Drying of the precipitate gave 3,5-bis-(1-methyl-3-trifluoromethylpyrazol-5-yloxy)phenyl-1-carboxamide in the form of white crystals.

Yield: 532 mg (97% of theory): melting point: 203° C.

5. 3-(1-Methyl-3-trifluoromethylpyrazol-5-yloxy)-5-(3-trifluoromethylpyrazol-1-yl)benzonitrile Under an atmosphere of nitrogen, 0.131 g (0.96 mmol) of 3-trifluoromethylpyrazole was initially charged in 5 ml of dimethylacetamide, and 0.033 g (1.1 mmol) of sodium hydride (80%) was added at 0° C. The mixture was allowed to warm to room temperature, and 0.250 g (0.88 mmol) of 3-fluoro-5-(1-methyl-3-trifluoromethylpyrazol-5-yloxy)benzonitrile was added, the mixture was heated at 140° C. for 8 h and cooled to room temperature, water was added to the reaction solution and the solution was stirred for a number of minutes. The mixture was extracted twice with heptane/ethyl acetate (1:1) and twice with ethyl acetate. The combined phases were washed with water and then dried over magnesium sulfate, filtered and concentrated. Column chromatography of the crude product gave 0.240 g of 3-(1-methyl-3-trifluoromethylpyrazol-5-yloxy)-5-(3-trifluoromethylpyrazol-1-yl)benzonitrile in the form of white crystals of melting point of 116–117° C.

6. 5-Carbonitrile-3-(1-methyl-3-trifluoromethylpyrazol-5-yloxy)benzonitrile

Under an atmosphere of nitrogen, 2.00 g (13.7 mmol) of 5-carbonitrile-3-fluorobenzonitrile were initially charged in 25 ml of N,N-dimethylformamide, and 2.27 g (16.4 mmol) of potassium carbonate were added a little at a time at room temperature. 2.50 g (15.1 mmol) of 1-methyl-3-(trifluoromethyl)-2-pyrazol-2-one were then added, and the mixture was heated at 150° C. for 2 h and cooled to room temperature, water and ethyl acetate were added to the reaction solution and the solution was stirred for a number of minutes. The phases were separated and the organic phase was washed repeatedly with water and with sodium chloride solution and then dried over magnesium sulfate, filtered and concentrated. Column chromatography of the crude product gave 5-carbonitrile-3-(1-methyl-3-trifluoromethylpyrazol-5-yloxy)benzonitrile in the form of white crystals.

Yield: 2.49 g (62% of theory); $^1$H NMR (CDCl$_3$/TMS): δ (ppm)=3.80 (s, 3H, methyl-H), 6.54 (s, 1H, pyrazolyl C—H), 8.20 (d, 2H, phenyl C—H), 8.38 (t, 1H, phenyl C—H).

The compounds of the formulae (Ia), (Ib), (Ic) and (Id) listed in Table 1 below can be obtained analogously to the examples mentioned above. The compounds of the formulae (Ia), (Ib), (Ic) and (Id) are compounds of the formula (I) which differ in the radical A-X as indicated below:

Formula (I): benzene ring with substituents R¹ (para to H), A—X and Y—B (meta positions), and H at remaining positions.

| Compound of the formula | (Ia) | (Ib) | (Ic) | (Id) |
|---|---|---|---|---|
| A—X | CF₃-pyrazole (N-CH₃) linked via O— | 3-CF₃-phenyl linked via O— | 5-CF₃-thiophene linked via O— | 2-CF₃-pyridine linked via O— |

(Ia): 3-CF₃-1-methyl-pyrazol-5-yl—O—
(Ib): 3-(trifluoromethyl)phenyl—O—
(Ic): 5-(trifluoromethyl)thien-3-yl—O—
(Id): 2-(trifluoromethyl)pyridin-4-yl—O—

In Table 1, the following abbreviations are used: Me=methyl; Et=ethyl, nPr=n-propyl, iPr=isopropyl, cPr=cyclopropyl, nBu=n-butyl, iBu=isobutyl, cBu=cyclobutyl, tBu 32 tert-butyl, cPentyl=cyclopentyl, cHexyl=cyclohexyl, Ph=phenyl, Bn=benzyl.

Thus in Table 1 when Y=O—CH₂, the radical B is attached to the CH₂ group.

TABLE 1

|  |  | B | Y | R¹ | Melting point [° C.] a | b | c | d |
|---|---|---|---|---|---|---|---|---|
| 1. | a–d | phenyl | O | CN | | | | |
| 2. | a–d | naphth-1-yl | O | CN | | | | |
| 3. | a–d | naphth-2-yl | O | CN | | | | |
| 4. | a–d | pyridin-2-yl | O | CN | | | | |
| 5. | a–d | pyridin-3-yl | O | CN | | | | |
| 6. | a–d | pyridin-4-yl | O | CN | | | | |
| 7. | a–d | 2-F-phenyl | O | CN | | | | |
| 8. | a–d | 3-F-phenyl | O | CN | colorless resin | | | |
| 9. | a–d | 4-F-phenyl | O | CN | | | | |
| 10. | a–d | 2,3-F₂-phenyl | O | CN | | | | |
| 11. | a–d | 2,4-F₂-phenyl | O | CN | | | | |
| 12. | a–d | 2,5-F₂-phenyl | O | CN | | | | |
| 13. | a–d | 2,6-F₂-phenyl | O | CN | | | | |
| 14. | a–d | 3,4-F₂-phenyl | O | CN | yellow resin | | | |
| 15. | a–d | 3,5-F₂-phenyl | O | CN | yellow resin | | | |
| 16. | a–d | 2,4,6-F₃-phenyl | O | CN | | | | |
| 17. | a–d | 2,3,4-F₃-phenyl | O | CN | | | | |
| 18. | a–d | 2-Cl-phenyl | O | CN | | | | |
| 19. | a–d | 3-Cl-phenyl | O | CN | | | | |
| 20. | a–d | 4-Cl-phenyl | O | CN | | | | |
| 21. | a–d | 2,3-Cl₂-phenyl | O | CN | | | | |
| 22. | a–d | 2,4-Cl₂-phenyl | O | CN | | | | |
| 23. | a–d | 2,5-Cl₂-phenyl | O | CN | | | | |
| 24. | a–d | 2,6-Cl₂-phenyl | O | CN | | | | |
| 25. | a–d | 3,4-Cl₂-phenyl | O | CN | yellow resin | | | |
| 26. | a–d | 3,5-Cl₂-phenyl | O | CN | | | | |
| 27. | a–d | 2,4,6-Cl₃-phenyl | O | CN | | | | |
| 28. | a–d | 2,3,4-Cl₃-phenyl | O | CN | | | | |
| 29. | a–d | 3,4,5-Cl₃-phenyl | O | CN | | | | |
| 30. | a–d | 2-F-4-Cl-phenyl | O | CN | yellow resin | | | |
| 31. | a–d | 2-Cl-4-F-phenyl | O | CN | | | | |
| 32. | a–d | 2-F-3-Cl-phenyl | O | CN | | | | |
| 33. | a–d | 2-Cl-3-F-phenyl | O | CN | | | | |
| 34. | a–d | 2-F-5-Cl-phenyl | O | CN | | | | |
| 35. | a–d | 2-Cl-5-F-phenyl | O | CN | | | | |
| 36. | a–d | 2-Cl-6-F-phenyl | O | CN | | | | |
| 37. | a–d | 2-Br-phenyl | O | CN | | | | |

TABLE 1-continued

| | | B | Y | R¹ | Melting point [° C.] a | b | c | d |
|---|---|---|---|---|---|---|---|---|
| 38. | a–d | 3-Br-phenyl | O | CN | | | | |
| 39. | a–d | 4-Br-phenyl | O | CN | | | | |
| 40. | a–d | 2,3-Br₂-phenyl | O | CN | | | | |
| 41. | a–d | 2,4-Br₂-phenyl | O | CN | | | | |
| 42. | a–d | 2,5-Br₂-phenyl | O | CN | | | | |
| 43. | a–d | 2-I-phenyl | O | CN | | | | |
| 44. | a–d | 3-I-phenyl | O | CN | | | | |
| 45. | a–d | 4-I-phenyl | O | CN | | | | |
| 46. | a–d | 2-F-4-MeO-phenyl | O | CN | | | | |
| 47. | a–d | 2-F-5-MeO-phenyl | O | CN | | | | |
| 48. | a–d | 2-MeO-phenyl | O | CN | | | | |
| 49. | a–d | 3-MeO-phenyl | O | CN | | | | |
| 50. | a–d | 4-MeO-phenyl | O | CN | | | | |
| 51. | a–d | 2,4-(MeO)₂-phenyl | O | CN | | | | |
| 52. | a–d | 2,3-(MeO)₂-phenyl | O | CN | | | | |
| 53. | a–d | 2,5-(MeO)₂-phenyl | O | CN | | | | |
| 54. | a–d | 2-Me-phenyl | O | CN | | | | |
| 55. | a–d | 3-Me-phenyl | O | CN | | | | |
| 56. | a–d | 4-Me-phenyl | O | CN | | | | |
| 57. | a–d | 2,4-(Me)₂-phenyl | O | CN | | | | |
| 58. | a–d | 2,3-(Me)₂-phenyl | O | CN | | | | |
| 59. | a–d | 2,5-(Me)₂-phenyl | O | CN | | | | |
| 60. | a–d | 2,6-(Me)₂-phenyl | O | CN | | | | |
| 61. | a–d | 2-CF₃-phenyl | O | CN | | | | |
| 62. | a–d | 3-CF₃-phenyl | O | CN | yellow wax | 77 | | |
| 63. | a–d | 4-CF₃-phenyl | O | CN | | | | |
| 64. | a–d | 2,4-(CF₃)₂-phenyl | O | CN | | | | |
| 65. | a–d | 2,6-Cl₂-4-(CF₃)₂-phenyl | O | CN | | | | |
| 66. | a–d | 2-CF₃O-phenyl | O | CN | | | | |
| 67. | a–d | 3-CF₃O-phenyl | O | CN | | | | |
| 68. | a–d | 4-CF₃O-phenyl | O | CN | | | | |
| 69. | a–d | 5-F-pyridin-2-yl | O | CN | | | | |
| 70. | a–d | 5-Cl-pyridin-2-yl | O | CN | | | | |
| 71. | a–d | 5-F-pyridin-4-yl | O | CN | | | | |
| 72. | a–d | 5-Cl-pyridin-4-yl | O | CN | | | | |
| 73. | a–d | 2-CF₃-pyridin-4-yl | O | CN | | | | see Ex. 3 |
| 74. | a–d | 2-CF₃-thiophen-4-yl | O | CN | | | brown wax | |
| 75. | a–d | 1-CH₃-5-CF₃-pyrazol-3-yl | O | CN | yellow oil | | | |
| 76. | a–d | 1-CH₃-3-CF₃-pyrazol-5-yl | O | CN | see Ex. 1 | | yellow resin | yellow oil |
| 77. | a–d | 1-CH₃-3-CF₃-pyrazol-5-yl | O | CONH₂ | see Ex. 4 | | | |
| 78. | a–d | 2-CF₃-thiadiazol-5-yl | O | CN | | | | |
| 79. | a–d | 2-CN-phenyl | O | CN | | | | |
| 80. | a–d | 3-CN-phenyl | O | CN | 121–122 | | | |
| 81. | a–d | 4-CN-phenyl | O | CN | | | | |
| 82. | a–d | 3,5-(CN)₂-phenyl | O | CN | | | | |
| 83. | a–d | 2-CN-4-F-phenyl | O | CN | | | | |
| 84. | a–d | 4-CN-2-F-phenyl | O | CN | | | | |
| 85. | a–d | 2-CF₃-oxadiazol-5-yl | O | CN | | | | |
| 86. | a–d | phenyl | O | Me | | | | |
| 87. | a–d | naphth-1-yl | O | Me | | | | |
| 88. | a–d | pyridin-2-yl | O | Me | | | | |
| 89. | a–d | pyridin-3-yl | O | Me | | | | |
| 90. | a–d | pyridin-4-yl | O | Me | | | | |
| 91. | a–d | 2-F-phenyl | O | Me | | | | |
| 92. | a–d | 3-F-phenyl | O | Me | | | | |
| 93. | a–d | 4-F-phenyl | O | Me | | | | |
| 94. | a–d | 2,3-F₂-phenyl | O | Me | | | | |
| 95. | a–d | 2,4-F₂-phenyl | O | Me | | | | |
| 96. | a–d | 2,5-F₂-phenyl | O | Me | | | | |
| 97. | a–d | 2,6-F₂-phenyl | O | Me | | | | |
| 98. | a–d | 3,4-F₂-phenyl | O | Me | | | | |
| 99. | a–d | 3,5-F₂-phenyl | O | Me | | | | |
| 100. | a–d | 2,4,6-F₃-phenyl | O | Me | | | | |
| 101. | a–d | 2,3,4-F₃-phenyl | O | Me | | | | |
| 102. | a–d | 3,4,5-F₃-phenyl | O | Me | | | | |
| 103. | a–d | 2-Cl-phenyl | O | Me | | | | |
| 104. | a–d | 3-Cl-phenyl | O | Me | | | | |
| 105. | a–d | 4-Cl-phenyl | O | Me | | | | |
| 106. | a–d | 2,3-Cl₂-phenyl | O | Me | | | | |

TABLE 1-continued

|  |  | B | Y | R¹ | Melting point [° C.] | | | |
|---|---|---|---|---|---|---|---|---|
|  |  |  |  |  | a | b | c | d |
| 107. | a–d | 2,4-Cl$_2$-phenyl | O | Me | | | | |
| 108. | a–d | 2,5-Cl$_2$-phenyl | O | Me | | | | |
| 109. | a–d | 2,6-Cl$_2$-phenyl | O | Me | | | | |
| 110. | a–d | 3,4-Cl$_2$-phenyl | O | Me | | | | |
| 111. | a–d | 3,5-Cl$_2$-phenyl | O | Me | | | | |
| 112. | a–d | 2,4,6-Cl$_3$-phenyl | O | Me | | | | |
| 113. | a–d | 2,3,4-Cl$_3$-phenyl | O | Me | | | | |
| 114. | a–d | 2,3,6-Cl$_3$-phenyl | O | Me | | | | |
| 115. | a–d | 2-F-4-Cl-phenyl | O | Me | | | | |
| 116. | a–d | 2-Cl-4-F-phenyl | O | Me | | | | |
| 117. | a–d | 2-F-3-Cl-phenyl | O | Me | | | | |
| 118. | a–d | 2-Cl-3-F-phenyl | O | Me | | | | |
| 119. | a–d | 2-F-5-Cl-phenyl | O | Me | | | | |
| 120. | a–d | 2-Cl-5-F-phenyl | O | Me | | | | |
| 121. | a–d | 2-Cl-6-F-phenyl | O | Me | | | | |
| 122. | a–d | 2-Br-phenyl | O | Me | | | | |
| 123. | a–d | 3-Br-phenyl | O | Me | | | | |
| 124. | a–d | 4-Br-phenyl | O | Me | | | | |
| 125. | a–d | 2,3-Br$_2$-phenyl | O | Me | | | | |
| 126. | a–d | 2,4-Br$_2$-phenyl | O | Me | | | | |
| 127. | a–d | 2,5-Br$_2$-phenyl | O | Me | | | | |
| 128. | a–d | 2-I-phenyl | O | Me | | | | |
| 129. | a–d | 3-I-phenyl | O | Me | | | | |
| 130. | a–d | 4-I-phenyl | O | Me | | | | |
| 131. | a–d | 2-F-4-MeO-phenyl | O | Me | | | | |
| 132. | a–d | 2-F-5-MeO-phenyl | O | Me | | | | |
| 133. | a–d | 2-MeO-phenyl | O | Me | | | | |
| 134. | a–d | 3-MeO-phenyl | O | Me | | | | |
| 135. | a–d | 4-MeO-phenyl | O | Me | | | | |
| 136. | a–d | 2,4-(MeO)$_2$-phenyl | O | Me | | | | |
| 137. | a–d | 2,3-(MeO)$_2$-phenyl | O | Me | | | | |
| 138. | a–d | 2,5-(MeO)$_2$-phenyl | O | Me | | | | |
| 139. | a–d | 2-Me-phenyl | O | Me | | | | |
| 140. | a–d | 3-Me-phenyl | O | Me | | | | |
| 141. | a–d | 4-Me-phenyl | O | Me | | | | |
| 142. | a–d | 2,4-(Me)$_2$-phenyl | O | Me | | | | |
| 143. | a–d | 2,3-(Me)$_2$-phenyl | O | Me | | | | |
| 144. | a–d | 2,5-(Me)$_2$-phenyl | O | Me | | | | |
| 145. | a–d | 2-CF$_3$-phenyl | O | Me | | | | |
| 146. | a–d | 3-CF$_3$-phenyl | O | Me | | | | |
| 147. | a–d | 4-CF$_3$-phenyl | O | Me | | | | |
| 148. | a–d | 2,4-(CF$_3$)$_2$-phenyl | O | Me | | | | |
| 149. | a–d | 2,6-Cl$_2$-4-(CF$_3$)$_2$-phenyl | O | Me | | | | |
| 150. | a–d | 2-CF$_3$O-phenyl | O | Me | | | | |
| 151. | a–d | 3-CF$_3$O-phenyl | O | Me | | | | |
| 152. | a–d | 4-CF$_3$O-phenyl | O | Me | | | | |
| 153. | a–d | 5-F-pyridin-2-yl | O | Me | | | | |
| 154. | a–d | 5-Cl-pyridin-2-yl | O | Me | | | | |
| 155. | a–d | 5-F-pyridin-4-yl | O | Me | | | | |
| 156. | a–d | 5-Cl-pyridin-4-yl | O | Me | | | | |
| 157. | a–d | 2-CF$_3$-pyridin-4-yl | O | Me | | | | |
| 158. | a–d | 1-CH$_3$-5-CF$_3$-pyrazol-3-yl | O | Me | | | | |
| 159. | a–d | 1-CH$_3$-3-CF$_3$-pyrazol-5-yl | O | Me | | | | |
| 160. | a–d | 2-CF$_3$-thiophen-4-yl | O | Me | | | | |
| 161. | a–d | 2-CF$_3$-thiadiazol-5-yl | O | Me | | | | |
| 162. | a–d | 2-CN-phenyl | O | Me | | | | |
| 163. | a–d | 3-CN-phenyl | O | Me | | | | |
| 164. | a–d | 4-CN-phenyl | O | Me | | | | |
| 165. | a–d | 3,5-(CN)$_2$-phenyl | O | Me | | | | |
| 166. | a–d | 2-CN-4-F-phenyl | O | Me | | | | |
| 167. | a–d | 4-CN-2-F-phenyl | O | Me | | | | |
| 168. | a–d | 2-CF$_3$-oxadiazol-5-yl | O | Me | | | | |
| 169. | a–d | phenyl | O | MeO | | | | |
| 170. | a–d | naphth-1-yl | O | MeO | | | | |
| 171. | a–d | pyridin-2-yl | O | MeO | | | | |
| 172. | a–d | pyridin-3-yl | O | MeO | | | | |
| 173. | a–d | pyridin-4-yl | O | MeO | | | | |
| 174. | a–d | 2-F-phenyl | O | MeO | | | | |
| 175. | a–d | 3-F-phenyl | O | MeO | | | | |
| 176. | a–d | 4-F-phenyl | O | MeO | | | | |
| 177. | a–d | 2,3-F$_2$-phenyl | O | MeO | | | | |
| 178. | a–d | 2,4-F$_2$-phenyl | O | MeO | | | | |

TABLE 1-continued

| | | B | Y | R¹ | Melting point [° C.] | | | |
|---|---|---|---|---|---|---|---|---|
| | | | | | a | b | c | d |
| 179. | a–d | 2,5-F$_2$-phenyl | O | MeO | | | | |
| 180. | a–d | 2,6-F$_2$-phenyl | O | MeO | | | | |
| 181. | a–d | 3,4-F$_2$-phenyl | O | MeO | | | | |
| 182. | a–d | 3,5-F$_2$-phenyl | O | MeO | | | | |
| 183. | a–d | 2,4,6-F$_3$-phenyl | O | MeO | | | | |
| 184. | a–d | 2,3,4-F$_3$-phenyl | O | MeO | | | | |
| 185. | a–d | 3,4,5-F$_3$-phenyl | O | MeO | | | | |
| 186. | a–d | 2-Cl-phenyl | O | MeO | | | | |
| 187. | a–d | 3-Cl-phenyl | O | MeO | | | | |
| 188. | a–d | 4-Cl-phenyl | O | MeO | | | | |
| 189. | a–d | 2,3-Cl$_2$-phenyl | O | MeO | | | | |
| 190. | a–d | 2,4-Cl$_2$-phenyl | O | MeO | | | | |
| 191. | a–d | 2,5-Cl$_2$-phenyl | O | MeO | | | | |
| 192. | a–d | 2,6-Cl$_2$-phenyl | O | MeO | | | | |
| 193. | a–d | 3,4-Cl$_2$-phenyl | O | MeO | | | | |
| 194. | a–d | 3,5-Cl$_2$-phenyl | O | MeO | | | | |
| 195. | a–d | 2,4,6-Cl$_3$-phenyl | O | MeO | | | | |
| 196. | a–d | 2,3,4-Cl$_3$-phenyl | O | MeO | | | | |
| 197. | a–d | 2-F-4-Cl-phenyl | O | MeO | | | | |
| 198. | a–d | 2-Cl-4-F-phenyl | O | MeO | | | | |
| 199. | a–d | 2-F-3-Cl-phenyl | O | MeO | | | | |
| 200. | a–d | 2-Cl-3-F-phenyl | O | MeO | | | | |
| 201. | a–d | 2-F-5-Cl-phenyl | O | MeO | | | | |
| 202. | a–d | 2-Cl-5-F-phenyl | O | MeO | | | | |
| 203. | a–d | 2-Cl-6-F-phenyl | O | MeO | | | | |
| 204. | a–d | 2-Br-phenyl | O | MeO | | | | |
| 205. | a–d | 3-Br-phenyl | O | MeO | | | | |
| 206. | a–d | 4-Br-phenyl | O | MeO | | | | |
| 207. | a–d | 2,4-Br$_2$-phenyl | O | MeO | | | | |
| 208. | a–d | 2,5-Br$_2$-phenyl | O | MeO | | | | |
| 209. | a–d | 2-I-phenyl | O | MeO | | | | |
| 210. | a–d | 3-I-phenyl | O | MeO | | | | |
| 211. | a–d | 4-I-phenyl | O | MeO | | | | |
| 212. | a–d | 2-F-4-MeO-phenyl | O | MeO | | | | |
| 213. | a–d | 2-F-5-MeO-phenyl | O | MeO | | | | |
| 214. | a–d | 2-MeO-phenyl | O | MeO | | | | |
| 215. | a–d | 3-MeO-phenyl | O | MeO | | | | |
| 216. | a–d | 4-MeO-phenyl | O | MeO | | | | |
| 217. | a–d | 2,4-(MeO)$_2$-phenyl | O | MeO | | | | |
| 218. | a–d | 3,4-(MeO)$_2$-phenyl | O | MeO | | | | |
| 219. | a–d | 2-Me-phenyl | O | MeO | | | | |
| 220. | a–d | 3-Me-phenyl | O | MeO | | | | |
| 221. | a–d | 4-Me-phenyl | O | MeO | | | | |
| 222. | a–d | 2,4-(Me)$_2$-phenyl | O | MeO | | | | |
| 223. | a–d | 2-CF$_3$-phenyl | O | MeO | | | | |
| 224. | a–d | 3-CF$_3$-phenyl | O | MeO | | | | |
| 225. | a–d | 4-CF$_3$-phenyl | O | MeO | | | | |
| 226. | a–d | 2,4-(CF$_3$)$_2$-phenyl | O | MeO | | | | |
| 227. | a–d | 2,6-Cl$_2$-4-(CF$_3$)$_2$-phenyl | O | MeO | | | | |
| 228. | a–d | 2-CF$_3$O-phenyl | O | MeO | | | | |
| 229. | a–d | 3-CF$_3$O-phenyl | O | MeO | | | | |
| 230. | a–d | 4-CF$_3$O-phenyl | O | MeO | | | | |
| 231. | a–d | 5-F-pyridin-2-yl | O | MeO | | | | |
| 232. | a–d | 5-Cl-pyridin-2-yl | O | MeO | | | | |
| 233. | a–d | 5-F-pyridin-4-yl | O | MeO | | | | |
| 234. | a–d | 5-Cl-pyridin-4-yl | O | MeO | | | | |
| 235. | a–d | 2-CF$_3$-pyridin-4-yl | O | MeO | | | | |
| 236. | a–d | 2-CF$_3$-thiophen-4-yl | O | MeO | | | | |
| 237. | a–d | 1-CH$_3$-5-CF$_3$-pyrazol-3-yl | O | MeO | | | | |
| 238. | a–d | 1-CH$_3$-3-CF$_3$-pyrazol-5-yl | O | MeO | | | | |
| 239. | a–d | 2-CF$_3$-thiadiazol-5-yl | O | MeO | | | | |
| 240. | a–d | 2-CN-phenyl | O | MeO | | | | |
| 241. | a–d | 3-CN-phenyl | O | MeO | | | | |
| 242. | a–d | 4-CN-phenyl | O | MeO | | | | |
| 243. | a–d | 3,5-(CN)$_2$-phenyl | O | MeO | | | | |
| 244. | a–d | 2-CN-4-F-phenyl | O | MeO | | | | |
| 245. | a–d | 4-CN-2-F-phenyl | O | MeO | | | | |
| 246. | a–d | 2-CF$_3$-oxadiazol-5-yl | O | MeO | | | | |
| 247. | a–d | phenyl | O | CHO | | | | |
| 248. | a–d | naphth-1-yl | O | CHO | | | | |
| 249. | a–d | pyridin-2-yl | O | CHO | | | | |
| 250. | a–d | pyridin-3-yl | O | CHO | | | | |

TABLE 1-continued

|  |  | B | Y | R¹ | Melting point [° C.] | | | |
|---|---|---|---|---|---|---|---|---|
|  |  |  |  |  | a | b | c | d |
| 251. | a–d | pyridin-4-yl | O | CHO | | | | |
| 252. | a–d | 2-F-phenyl | O | CHO | | | | |
| 253. | a–d | 3-F-phenyl | O | CHO | | | | |
| 254. | a–d | 4-F-phenyl | O | CHO | | | | |
| 255. | a–d | 2,3-F$_2$-phenyl | O | CHO | | | | |
| 256. | a–d | 2,4-F$_2$-phenyl | O | CHO | | | | |
| 257. | a–d | 2,5-F$_2$-phenyl | O | CHO | | | | |
| 258. | a–d | 2,6-F$_2$-phenyl | O | CHO | | | | |
| 259. | a–d | 3,4-F$_2$-phenyl | O | CHO | | | | |
| 260. | a–d | 3,5-F$_2$-phenyl | O | CHO | | | | |
| 261. | a–d | 2,4,6-F$_3$-phenyl | O | CHO | | | | |
| 262. | a–d | 2,3,4-F$_3$-phenyl | O | CHO | | | | |
| 263. | a–d | 2-Cl-phenyl | O | CHO | | | | |
| 264. | a–d | 3-Cl-phenyl | O | CHO | | | | |
| 265. | a–d | 4-Cl-phenyl | O | CHO | | | | |
| 266. | a–d | 2,3-Cl$_2$-phenyl | O | CHO | | | | |
| 267. | a–d | 2,4-Cl$_2$-phenyl | O | CHO | | | | |
| 268. | a–d | 2,5-Cl$_2$-phenyl | O | CHO | | | | |
| 269. | a–d | 2,6-Cl$_2$-phenyl | O | CHO | | | | |
| 270. | a–d | 3,4-Cl$_2$-phenyl | O | CHO | | | | |
| 271. | a–d | 3,5-Cl$_2$-phenyl | O | CHO | | | | |
| 272. | a–d | 2,3,4-Cl$_3$-phenyl | O | CHO | | | | |
| 273. | a–d | 2-F-4-Cl-phenyl | O | CHO | | | | |
| 274. | a–d | 2-Cl-4-F-phenyl | O | CHO | | | | |
| 275. | a–d | 2-F-3-Cl-phenyl | O | CHO | | | | |
| 276. | a–d | 2-Cl-3-F-phenyl | O | CHO | | | | |
| 277. | a–d | 2-F-5-Cl-phenyl | O | CHO | | | | |
| 278. | a–d | 2-Cl-5-F-phenyl | O | CHO | | | | |
| 279. | a–d | 2-Cl-6-F-phenyl | O | CHO | | | | |
| 280. | a–d | 2-Br-phenyl | O | CHO | | | | |
| 281. | a–d | 3-Br-phenyl | O | CHO | | | | |
| 282. | a–d | 4-Br-phenyl | O | CHO | | | | |
| 283. | a–d | 2,3-Br$_2$-phenyl | O | CHO | | | | |
| 284. | a–d | 2,5-Br$_2$-phenyl | O | CHO | | | | |
| 285. | a–d | 2-I-phenyl | O | CHO | | | | |
| 286. | a–d | 3-I-phenyl | O | CHO | | | | |
| 287. | a–d | 4-I-phenyl | O | CHO | | | | |
| 288. | a–d | 2-F-4-MeO-phenyl | O | CHO | | | | |
| 289. | a–d | 2-F-5-MeO-phenyl | O | CHO | | | | |
| 290. | a–d | 2-MeO-phenyl | O | CHO | | | | |
| 291. | a–d | 3-MeO-phenyl | O | CHO | | | | |
| 292. | a–d | 4-MeO-phenyl | O | CHO | | | | |
| 293. | a–d | 2,4-(MeO)$_2$-phenyl | O | CHO | | | | |
| 294. | a–d | 2,3-(MeO)$_2$-phenyl | O | CHO | | | | |
| 295. | a–d | 2-Me-phenyl | O | CHO | | | | |
| 296. | a–d | 3-Me-phenyl | O | CHO | | | | |
| 297. | a–d | 4-Me-phenyl | O | CHO | | | | |
| 298. | a–d | 2,4-(Me)$_2$-phenyl | O | CHO | | | | |
| 299. | a–d | 2,3-(Me)$_2$-phenyl | O | CHO | | | | |
| 300. | a–d | 2,5-(Me)$_2$-phenyl | O | CHO | | | | |
| 301. | a–d | 2-CF$_3$-phenyl | O | CHO | | | | |
| 302. | a–d | 3-CF$_3$-phenyl | O | CHO | | | | |
| 303. | a–d | 4-CF$_3$-phenyl | O | CHO | | | | |
| 304. | a–d | 2,4-(CF$_3$)$_2$-phenyl | O | CHO | | | | |
| 305. | a–d | 2,6-Cl$_2$-4-(CF$_3$)$_2$-phenyl | O | CHO | | | | |
| 306. | a–d | 2-CF$_3$O-phenyl | O | CHO | | | | |
| 307. | a–d | 3-CF$_3$O-phenyl | O | CHO | | | | |
| 308. | a–d | 4-CF$_3$O-phenyl | O | CHO | | | | |
| 309. | a–d | 5-F-pyridin-2-yl | O | CHO | | | | |
| 310. | a–d | 5-Cl-pyridin-2-yl | O | CHO | | | | |
| 311. | a–d | 5-F-pyridin-4-yl | O | CHO | | | | |
| 312. | a–d | 5-Cl-pyridin-4-yl | O | CHO | | | | |
| 313. | a–d | 2-CF$_3$-pyridin-4-yl | O | CHO | | | | |
| 314. | a–d | 2-CF$_3$-thiophen-4-yl | O | CHO | | | | |
| 315. | a–d | 1-CH$_3$-5-CF$_3$-pyrazol-3-yl | O | CHO | | | | |
| 316. | a–d | 1-CH$_3$-3-CF$_3$-pyrazol-5-yl | O | CHO | | | | |
| 317. | a–d | 2-CF$_3$-thiadiazol-5-yl | O | CHO | | | | |
| 318. | a–d | 2-CN-phenyl | O | CHO | | | | |
| 319. | a–d | 3-CN-phenyl | O | CHO | | | | |
| 320. | a–d | 4-CN-phenyl | O | CHO | | | | |
| 321. | a–d | 3,5-(CN)$_2$-phenyl | O | CHO | | | | |
| 322. | a–d | 2-CN-4-F-phenyl | O | CHO | | | | |

TABLE 1-continued

| | | B | Y | R¹ | Melting point [° C.] | | | |
|---|---|---|---|---|---|---|---|---|
| | | | | | a | b | c | d |
| 323. | a–d | 4-CN-2-F-phenyl | O | CHO | | | | |
| 324. | a–d | 2-CF$_3$-oxadiazol-5-yl | O | CHO | | | | |
| 325. | a–d | phenyl | O | NO$_2$ | | | | |
| 326. | a–d | naphth-1-yl | O | NO$_2$ | | | | |
| 327. | a–d | pyridin-2-yl | O | NO$_2$ | | | | |
| 328. | a–d | pyridin-3-yl | O | NO$_2$ | | | | |
| 329. | a–d | pyridin-4-yl | O | NO$_2$ | | | | |
| 330. | a–d | 2-F-phenyl | O | NO$_2$ | | | | |
| 331. | a–d | 3-F-phenyl | O | NO$_2$ | | | | |
| 332. | a–d | 4-F-phenyl | O | NO$_2$ | | | | |
| 333. | a–d | 2,3-F$_2$-phenyl | O | NO$_2$ | | | | |
| 334. | a–d | 2,4-F$_2$-phenyl | O | NO$_2$ | | | | |
| 335. | a–d | 2,5-F$_2$-phenyl | O | NO$_2$ | | | | |
| 336. | a–d | 2,6-F$_2$-phenyl | O | NO$_2$ | | | | |
| 337. | a–d | 3,4-F$_2$-phenyl | O | NO$_2$ | | | | |
| 338. | a–d | 3,5-F$_2$-phenyl | O | NO$_2$ | | | | |
| 339. | a–d | 2,4,6-F$_3$-phenyl | O | NO$_2$ | | | | |
| 340. | a–d | 2,3,5-F$_3$-phenyl | O | NO$_2$ | | | | |
| 341. | a–d | 3,4,5-F$_3$-phenyl | O | NO$_2$ | | | | |
| 342. | a–d | 2-Cl-phenyl | O | NO$_2$ | | | | |
| 343. | a–d | 3-Cl-phenyl | O | NO$_2$ | | | | |
| 344. | a–d | 4-Cl-phenyl | O | NO$_2$ | | | | |
| 345. | a–d | 2,3-Cl$_2$-phenyl | O | NO$_2$ | | | | |
| 346. | a–d | 2,4-Cl$_2$-phenyl | O | NO$_2$ | | | | |
| 347. | a–d | 2,5-Cl$_2$-phenyl | O | NO$_2$ | | | | |
| 348. | a–d | 2,6-Cl$_2$-phenyl | O | NO$_2$ | | | | |
| 349. | a–d | 3,4-Cl$_2$-phenyl | O | NO$_2$ | | | | |
| 350. | a–d | 3,5-Cl$_2$-phenyl | O | NO$_2$ | | | | |
| 351. | a–d | 2,4,6-Cl$_3$-phenyl | O | NO$_2$ | | | | |
| 352. | a–d | 2,3,4-Cl$_3$-phenyl | O | NO$_2$ | | | | |
| 353. | a–d | 3,4,5-Cl$_3$-phenyl | O | NO$_2$ | | | | |
| 354. | a–d | 2-F-4-Cl-phenyl | O | NO$_2$ | | | | |
| 355. | a–d | 2-Cl-4-F-phenyl | O | NO$_2$ | | | | |
| 356. | a–d | 2-F-3-Cl-phenyl | O | NO$_2$ | | | | |
| 357. | a–d | 2-Cl-3-F-phenyl | O | NO$_2$ | | | | |
| 358. | a–d | 2-F-5-Cl-phenyl | O | NO$_2$ | | | | |
| 359. | a–d | 2-Cl-5-F-phenyl | O | NO$_2$ | | | | |
| 360. | a–d | 2-Cl-6-F-phenyl | O | NO$_2$ | | | | |
| 361. | a–d | 2-Br-phenyl | O | NO$_2$ | | | | |
| 362. | a–d | 3-Br-phenyl | O | NO$_2$ | | | | |
| 363. | a–d | 4-Br-phenyl | O | NO$_2$ | | | | |
| 364. | a–d | 2,3-Br$_2$-phenyl | O | NO$_2$ | | | | |
| 365. | a–d | 2,4-Br$_2$-phenyl | O | NO$_2$ | | | | |
| 366. | a–d | 2,5-Br$_2$-phenyl | O | NO$_2$ | | | | |
| 367. | a–d | 2-I-phenyl | O | NO$_2$ | | | | |
| 368. | a–d | 3-I-phenyl | O | NO$_2$ | | | | |
| 369. | a–d | 4-I-phenyl | O | NO$_2$ | | | | |
| 370. | a–d | 2-F-4-MeO-phenyl | O | NO$_2$ | | | | |
| 371. | a–d | 2-F-5-MeO-phenyl | O | NO$_2$ | | | | |
| 372. | a–d | 2-MeO-phenyl | O | NO$_2$ | | | | |
| 373. | a–d | 3-MeO-phenyl | O | NO$_2$ | | | | |
| 374. | a–d | 4-MeO-phenyl | O | NO$_2$ | | | | |
| 375. | a–d | 2,4-(MeO)$_2$-phenyl | O | NO$_2$ | | | | |
| 376. | a–d | 2,5-(MeO)$_2$-phenyl | O | NO$_2$ | | | | |
| 377. | a–d | 2-Me-phenyl | O | NO$_2$ | | | | |
| 378. | a–d | 3-Me-phenyl | O | NO$_2$ | | | | |
| 379. | a–d | 4-Me-phenyl | O | NO$_2$ | | | | |
| 380. | a–d | 2,4-(Me)$_2$-phenyl | O | NO$_2$ | | | | |
| 381. | a–d | 2,5-(Me)$_2$-phenyl | O | NO$_2$ | | | | |
| 382. | a–d | 2-CF$_3$-phenyl | O | NO$_2$ | | | | |
| 383. | a–d | 3-CF$_3$-phenyl | O | NO$_2$ | | | | |
| 384. | a–d | 4-CF$_3$-phenyl | O | NO$_2$ | | | | |
| 385. | a–d | 2,4-(CF$_3$)$_2$-phenyl | O | NO$_2$ | | | | |
| 386. | a–d | 2,6-Cl$_2$-4-(CF$_3$)$_2$-phenyl | O | NO$_2$ | | | | |
| 387. | a–d | 2-CF$_3$O-phenyl | O | NO$_2$ | | | | |
| 388. | a–d | 3-CF$_3$O-phenyl | O | NO$_2$ | | | | |
| 389. | a–d | 4-CF$_3$O-phenyl | O | NO$_2$ | | | | |
| 390. | a–d | 5-F-pyridin-2-yl | O | NO$_2$ | | | | |
| 391. | a–d | 5-Cl-pyridin-2-yl | O | NO$_2$ | | | | |
| 392. | a–d | 5-F-pyridin-4-yl | O | NO$_2$ | | | | |
| 393. | a–d | 5-Cl-pyridin-4-yl | O | NO$_2$ | | | | |
| 394. | a–d | 2-CF$_3$-pyridin-4-yl | O | NO$_2$ | | | | |
| 395. | a–d | 2-CF$_3$-thiophen-4-yl | O | NO$_2$ | | | | |
| 396. | a–d | 1-CH$_3$-5-CF$_3$- | O | NO$_2$ | light-red | | | |

TABLE 1-continued

|  |  | B | Y | R¹ | Melting point [° C.] | | | |
|---|---|---|---|---|---|---|---|---|
|  |  |  |  |  | a | b | c | d |
|  |  | pyrazol-3-yl |  |  | oil |  |  |  |
| 397. | a–d | 1-CH₃-3-CF₃-pyrazol-5-yl | O | NO₂ | 135 |  |  |  |
| 398. | a–d | 2-CF₃-thiadiazol-5-yl | O | NO₂ |  |  |  |  |
| 399. | a–d | 2-CN-phenyl | O | NO₂ |  |  |  |  |
| 400. | a–d | 3-CN-phenyl | O | NO₂ |  |  |  |  |
| 401. | a–d | 4-CN-phenyl | O | NO₂ |  |  |  |  |
| 402. | a–d | 3,5-(CN)₂-phenyl | O | NO₂ |  |  |  |  |
| 403. | a–d | 2-CN-4-F-phenyl | O | NO₂ |  |  |  |  |
| 404. | a–d | 4-CN-2-F-phenyl | O | NO₂ |  |  |  |  |
| 405. | a–d | 2-CF₃-oxadiazol-5-yl | O | NO₂ |  |  |  |  |
| 406. | a–d | NH-phenyl | CO | CN |  |  |  |  |
| 407. | a–d | NH-naphth-1-yl | CO | CN |  |  |  |  |
| 408. | a–d | NH-pyridin-2-yl | CO | CN |  |  |  |  |
| 409. | a–d | NH-pyridin-3-yl | CO | CN |  |  |  |  |
| 410. | a–d | NH-pyridin-4-yl | CO | CN |  |  |  |  |
| 411. | a–d | NH-2-F-phenyl | CO | CN |  |  |  |  |
| 412. | a–d | NH-3-F-phenyl | CO | CN |  |  |  |  |
| 413. | a–d | NH-4-F-phenyl | CO | CN |  |  |  |  |
| 414. | a–d | NH-2,3-F₂-phenyl | CO | CN |  |  |  |  |
| 415. | a–d | NH-2,4-F₂-phenyl | CO | CN |  |  |  |  |
| 416. | a–d | NH-2,5-F₂-phenyl | CO | CN |  |  |  |  |
| 417. | a–d | NH-2,6-F₂-phenyl | CO | CN |  |  |  |  |
| 418. | a–d | NH-3,4-F₂-phenyl | CO | CN |  |  |  |  |
| 419. | a–d | NH-3,5-F₂-phenyl | CO | CN |  |  |  |  |
| 420. | a–d | NH-2,4,6-F₃-phenyl | CO | CN |  |  |  |  |
| 421. | a–d | NH-2,3,4-F₃-phenyl | CO | CN |  |  |  |  |
| 422. | a–d | NH-2-Cl-phenyl | CO | CN |  |  |  |  |
| 423. | a–d | NH-3-Cl-phenyl | CO | CN |  |  |  |  |
| 424. | a–d | NH-4-Cl-phenyl | CO | CN |  |  |  |  |
| 425. | a–d | NH-2,3-Cl₂-phenyl | CO | CN |  |  |  |  |
| 426. | a–d | NH-2,4-Cl₂-phenyl | CO | CN |  |  |  |  |
| 427. | a–d | NH-2,5-Cl₂-phenyl | CO | CN |  |  |  |  |
| 428. | a–d | NH-2,6-Cl₂-phenyl | CO | CN |  |  |  |  |
| 429. | a–d | NH-3,4-Cl₂-phenyl | CO | CN |  |  |  |  |
| 430. | a–d | NH-3,5-Cl₂-phenyl | CO | CN |  |  |  |  |
| 431. | a–d | NH-2,4,6-Cl₃-phenyl | CO | CN |  |  |  |  |
| 432. | a–d | NH-2,3,4-Cl₃-phenyl | CO | CN |  |  |  |  |
| 433 | a–d | NH-3,4,5-Cl₃-phenyl | CO | CN |  |  |  |  |
| 434. | a–d | NH-2-F-4-Cl-phenyl | CO | CN |  |  |  |  |
| 435. | a–d | NH-2-Cl-4-F-phenyl | CO | CN |  |  |  |  |
| 436. | a–d | NH-2-F-3-Cl-phenyl | CO | CN |  |  |  |  |
| 437. | a–d | NH-2-Cl-3-F-phenyl | CO | CN |  |  |  |  |
| 438. | a–d | NH-2-F-5-Cl-phenyl | CO | CN |  |  |  |  |
| 439. | a–d | NH-2-Cl-5-F-phenyl | CO | CN |  |  |  |  |
| 440. | a–d | NH-2-Cl-6-F-phenyl | CO | CN |  |  |  |  |
| 441. | a–d | NH-2-Br-phenyl | CO | CN |  |  |  |  |
| 442. | a–d | NH-3-Br-phenyl | CO | CN |  |  |  |  |
| 443. | a–d | NH-4-Br-phenyl | CO | CN |  |  |  |  |
| 444. | a–d | NH-2,3-Br₂-phenyl | CO | CN |  |  |  |  |
| 445. | a–d | NH-2,4-Br₂-phenyl | CO | CN |  |  |  |  |
| 446. | a–d | NH-2,5-Br₂-phenyl | CO | CN |  |  |  |  |
| 447. | a–d | NH-2-I-phenyl | CO | CN |  |  |  |  |
| 448. | a–d | NH-3-I-phenyl | CO | CN |  |  |  |  |
| 449. | a–d | NH-4-I-phenyl | CO | CN |  |  |  |  |
| 450. | a–d | NH-2-F-4-MeO-phenyl | CO | CN |  |  |  |  |
| 451. | a–d | NH-2-F-5-MeO-phenyl | CO | CN |  |  |  |  |
| 452. | a–d | NH-2-MeO-phenyl | CO | CN |  |  |  |  |
| 453. | a–d | NH-3-MeO-phenyl | CO | CN |  |  |  |  |
| 454. | a–d | NH-4-MeO-phenyl | CO | CN |  |  |  |  |
| 455 | a–d | NH-2,4-(MeO)₂-phenyl | CO | CN |  |  |  |  |
| 456. | a–d | NH-2,3-(MeO)₂-phenyl | CO | CN |  |  |  |  |
| 457. | a–d | NH-2,5-(MeO)₂-phenyl | CO | CN |  |  |  |  |
| 458. | a–d | NH-2-Me-phenyl | CO | CN |  |  |  |  |
| 459. | a–d | NH-3-Me-phenyl | CO | CN |  |  |  |  |
| 460. | a–d | NH-4-Me-phenyl | CO | CN |  |  |  |  |
| 461. | a–d | NH-2,4-(Me)₂-phenyl | CO | CN |  |  |  |  |
| 462. | a–d | NH-2,5-(Me)₂-phenyl | CO | CN |  |  |  |  |

TABLE 1-continued

| | | B | Y | R¹ | Melting point [° C.] | | | |
|---|---|---|---|---|---|---|---|---|
| | | | | | a | b | c | d |
| 463. | a–d | NH-2-CF₃-phenyl | CO | CN | | | | |
| 464. | a–d | NH-3-CF₃-phenyl | CO | CN | | | | |
| 465. | a–d | NH-4-CF₃-phenyl | CO | CN | | | | |
| 466. | a–d | NH-2,4-(CF₃)₂-phenyl | CO | CN | | | | |
| 467. | a–d | NH-2,6-Cl₂-4-(CF₃)₂-phenyl | CO | CN | | | | |
| 468. | a–d | NH-2-CF₃O-phenyl | CO | CN | | | | |
| 469. | a–d | NH-3-CF₃O-phenyl | CO | CN | | | | |
| 470. | a–d | NH-4-CF₃O-phenyl | CO | CN | | | | |
| 471. | a–d | NH-5-F-pyridin-2-yl | CO | CN | | | | |
| 472. | a–d | NH-5-Cl-pyridin-2-yl | CO | CN | | | | |
| 473. | a–d | NH-5-F-pyridin-4-yl | CO | CN | | | | |
| 474. | a–d | NH-5-Cl-pyridin-4-yl | CO | CN | | | | |
| 475. | a–d | NH-2-CN-phenyl | CO | CN | | | | |
| 476. | a–d | NH-3-CN-phenyl | CO | CN | | | | |
| 477. | a–d | NH-4-CN-phenyl | CO | CN | | | | |
| 478. | a–d | NH-3,5-(CN)₂-phenyl | CO | CN | | | | |
| 479. | a–d | NH-2-CN-4-F-phenyl | CO | CN | | | | |
| 480. | a–d | NH-4-CN-2-F-phenyl | CO | CN | | | | |
| 481. | a–d | NH-phenyl | CO | Me | | | | |
| 482. | a–d | NH-naphth-1-yl | CO | Me | | | | |
| 483. | a–d | NH-pyridin-2-yl | CO | Me | | | | |
| 484. | a–d | NH-pyridin-3-yl | CO | Me | | | | |
| 485. | a–d | NH-pyridin-4-yl | CO | Me | | | | |
| 486. | a–d | NH-2-F-phenyl | CO | Me | | | | |
| 487. | a–d | NH-3-F-phenyl | CO | Me | | | | |
| 488. | a–d | NH-4-F-phenyl | CO | Me | | | | |
| 489. | a–d | NH-2,3-F₂-phenyl | CO | Me | | | | |
| 490. | a–d | NH-2,4-F₂-phenyl | CO | Me | | | | |
| 491. | a–d | NH-2,5-F₂-phenyl | CO | Me | | | | |
| 492. | a–d | NH-2,6-F₂-phenyl | CO | Me | | | | |
| 493. | a–d | NH-3,4-F₂-phenyl | CO | Me | | | | |
| 494. | a–d | NH-3,5-F₂-phenyl | CO | Me | | | | |
| 495. | a–d | NH-2,4,6-F₃-phenyl | CO | Me | | | | |
| 496. | a–d | NH-2,3,4-F₃-phenyl | CO | Me | | | | |
| 497. | a–d | NH-2-Cl-phenyl | CO | Me | | | | |
| 498. | a–d | NH-3-Cl-phenyl | CO | Me | | | | |
| 499. | a–d | NH-4-Cl-phenyl | CO | Me | | | | |
| 500. | a–d | NH-2,3-Cl₂-phenyl | CO | Me | | | | |
| 501. | a–d | NH-2,4-Cl₂-phenyl | CO | Me | | | | |
| 502. | a–d | NH-2,5-Cl₂-phenyl | CO | Me | | | | |
| 503. | a–d | NH-2,6-Cl₂-phenyl | CO | Me | | | | |
| 504. | a–d | NH-3,4-Cl₂-phenyl | CO | Me | | | | |
| 505. | a–d | NH-3,5-Cl₂-phenyl | CO | Me | | | | |
| 506. | a–d | NH-2,4,6-Cl₃-phenyl | CO | Me | | | | |
| 507. | a–d | NH-2,3,4-Cl₃-phenyl | CO | Me | | | | |
| 508. | a–d | NH-3,4,5-Cl₃-phenyl | CO | Me | | | | |
| 509. | a–d | NH-2-F-4-Cl-phenyl | CO | Me | | | | |
| 510. | a–d | NH-2-Cl-4-F-phenyl | CO | Me | | | | |
| 511. | a–d | NH-2-F-3-Cl-phenyl | CO | Me | | | | |
| 512. | a–d | NH-2-Cl-3-F-phenyl | CO | Me | | | | |
| 513. | a–d | NH-2-F-5-Cl-phenyl | CO | Me | | | | |
| 514. | a–d | NH-2-Cl-5-F-phenyl | CO | Me | | | | |
| 515. | a–d | NH-2-Cl-6-F-phenyl | CO | Me | | | | |
| 516. | a–d | NH-2-Br-phenyl | CO | Me | | | | |
| 517. | a–d | NH-3-Br-phenyl | CO | Me | | | | |
| 518. | a–d | NH-4-Br-phenyl | CO | Me | | | | |
| 519. | a–d | NH-2,3-Br₂-phenyl | CO | Me | | | | |
| 520. | a–d | NH-2,4-Br₂-phenyl | CO | Me | | | | |
| 521. | a–d | NH-2,5-Br₂-phenyl | CO | Me | | | | |
| 522. | a–d | NH-2-I-phenyl | CO | Me | | | | |
| 523. | a–d | NH-3-I-phenyl | CO | Me | | | | |
| 524. | a–d | NH-4-I-phenyl | CO | Me | | | | |
| 525. | a–d | NH-2-F-4-MeO-phenyl | CO | Me | | | | |
| 526. | a–d | NH-2-F-5-MeO-phenyl | CO | Me | | | | |
| 527. | a–d | NH-2-MeO-phenyl | CO | Me | | | | |
| 528. | a–d | NH-3-MeO-phenyl | CO | Me | | | | |
| 529. | a–d | NH-4-MeO-phenyl | CO | Me | | | | |
| 530. | a–d | NH-2,4-(MeO)₂- | CO | Me | | | | |

TABLE 1-continued

|  |  | B | Y | R¹ | Melting point [° C.] | | | |
|---|---|---|---|---|---|---|---|---|
|  |  |  |  |  | a | b | c | d |
| 531. | a–d | NH-2,3-(MeO)$_2$-phenyl | CO | Me | | | | |
| 532. | a–d | NH-2,5-(MeO)$_2$-phenyl | CO | Me | | | | |
| 533. | a–d | NH-2-Me-phenyl | CO | Me | | | | |
| 534. | a–d | NH-3-Me-phenyl | CO | Me | | | | |
| 535. | a–d | NH-4-Me-phenyl | CO | Me | | | | |
| 536. | a–d | NH-2,4-(Me)$_2$-phenyl | CO | Me | | | | |
| 537. | a–d | NH-2,5-(Me)$_2$-phenyl | CO | Me | | | | |
| 538. | a–d | NH-2-CF$_3$-phenyl | CO | Me | | | | |
| 539. | a–d | NH-3-CF$_3$-phenyl | CO | Me | | | | |
| 540. | a–d | NH-4-CF$_3$-phenyl | CO | Me | | | | |
| 541. | a–d | NH-2,4-(CF$_3$)$_2$-phenyl | CO | Me | | | | |
| 542. | a–d | NH-2,6-Cl$_2$-4-(CF$_3$)$_2$-phenyl | CO | Me | | | | |
| 543. | a–d | NH-2-CF$_3$O-phenyl | CO | Me | | | | |
| 544. | a–d | NH-3-CF$_3$O-phenyl | CO | Me | | | | |
| 545. | a–d | NH-4-CF$_3$O-phenyl | CO | Me | | | | |
| 546. | a–d | NH-5-F-pyridin-2-yl | CO | Me | | | | |
| 547. | a–d | NH-5-Cl-pyridin-2-yl | CO | Me | | | | |
| 548. | a–d | NH-5-F-pyridin-4-yl | CO | Me | | | | |
| 549. | a–d | NH-5-Cl-pyridin-4-yl | CO | Me | | | | |
| 550. | a–d | NH-2-CN-phenyl | CO | Me | | | | |
| 551. | a–d | NH-3-CN-phenyl | CO | Me | | | | |
| 552. | a–d | NH-4-CN-phenyl | CO | Me | | | | |
| 553. | a–d | NH-3,5-(CN)$_2$-phenyl | CO | Me | | | | |
| 554. | a–d | NH-2-CN-4-F-phenyl | CO | Me | | | | |
| 555. | a–d | NH-4-CN-2-F-phenyl | CO | Me | | | | |
| 556. | a–d | NH-phenyl | CO | MeO | | | | |
| 557. | a–d | NH-naphth-1-yl | CO | MeO | | | | |
| 558. | a–d | NH-pyridin-2-yl | CO | MeO | | | | |
| 559. | a–d | NH-pyridin-3-yl | CO | MeO | | | | |
| 560. | a–d | NH-pyridin-4-yl | CO | MeO | | | | |
| 561. | a–d | NH-2-F-phenyl | CO | MeO | | | | |
| 562. | a–d | NH-3-F-phenyl | CO | MeO | | | | |
| 563. | a–d | NH-4-F-phenyl | CO | MeO | | | | |
| 564. | a–d | NH-2,3-F$_2$-phenyl | CO | MeO | | | | |
| 565. | a–d | NH-2,4-F$_2$-phenyl | CO | MeO | | | | |
| 566. | a–d | NH-2,5-F$_2$-phenyl | CO | MeO | | | | |
| 567. | a–d | NH-2,6-F$_2$-phenyl | CO | MeO | | | | |
| 568. | a–d | NH-3,4-F$_2$-phenyl | CO | MeO | | | | |
| 569. | a–d | NH-3,5-F$_2$-phenyl | CO | MeO | | | | |
| 570. | a–d | NH-2,4,6-F$_3$-phenyl | CO | MeO | | | | |
| 571. | a–d | NH-2,3,4-F$_3$-phenyl | CO | MeO | | | | |
| 572. | a–d | NH-2-Cl-phenyl | CO | MeO | | | | |
| 573. | a–d | NH-3-Cl-phenyl | CO | MeO | | | | |
| 574. | a–d | NH-4-Cl-phenyl | CO | MeO | | | | |
| 575. | a–d | NH-2,3-Cl$_2$-phenyl | CO | MeO | | | | |
| 576. | a–d | NH-2,4-Cl$_2$-phenyl | CO | MeO | | | | |
| 577. | a–d | NH-2,5-Cl$_2$-phenyl | CO | MeO | | | | |
| 578. | a–d | NH-2,6-Cl$_2$-phenyl | CO | MeO | | | | |
| 579. | a–d | NH-3,4-Cl$_2$-phenyl | CO | MeO | | | | |
| 580. | a–d | NH-3,5-Cl$_2$-phenyl | CO | MeO | | | | |
| 581. | a–d | NH-2,4,6-Cl$_3$-phenyl | CO | MeO | | | | |
| 582. | a–d | NH-2,3,4-Cl$_3$-phenyl | CO | MeO | | | | |
| 583. | a–d | NH-3,4,5-Cl$_3$-phenyl | CO | MeO | | | | |
| 584. | a–d | NH-2-F-4-Cl-phenyl | CO | MeO | | | | |
| 585. | a–d | NH-2-Cl-4-F-phenyl | CO | MeO | | | | |
| 586. | a–d | NH-2-F-3-Cl-phenyl | CO | MeO | | | | |
| 587. | a–d | NH-2-Cl-3-F-phenyl | CO | MeO | | | | |
| 588. | a–d | NH-2-F-5-Cl-phenyl | CO | MeO | | | | |
| 589. | a–d | NH-2-Cl-5-F-phenyl | CO | MeO | | | | |
| 590. | a–d | NH-2-Cl-6-F-phenyl | CO | MeO | | | | |
| 591. | a–d | NH-2-Br-phenyl | CO | MeO | | | | |
| 592. | a–d | NH-3-Br-phenyl | CO | MeO | | | | |
| 593. | a–d | NH-4-Br-phenyl | CO | MeO | | | | |
| 594. | a–d | NH-2,3-Br$_2$-phenyl | CO | MeO | | | | |
| 595. | a–d | NH-2,4-Br$_2$-phenyl | CO | MeO | | | | |
| 596. | a–d | NH-2,5-Br$_2$-phenyl | CO | MeO | | | | |
| 597. | a–d | NH-2-I-phenyl | CO | MeO | | | | |
| 598. | a–d | NH-3-I-phenyl | CO | MeO | | | | |
| 599. | a–d | NH-4-I-phenyl | CO | MeO | | | | |
| 600. | a–d | NH-2-F-4-MeO- | CO | MeO | | | | |

TABLE 1-continued

| | | B | Y | R¹ | Melting point [° C.] | | | |
|---|---|---|---|---|---|---|---|---|
| | | | | | a | b | c | d |
| 601. | a–d | NH-2-F-5-MeO-phenyl | CO | MeO | | | | |
| 602. | a–d | NH-2-MeO-phenyl | CO | MeO | | | | |
| 603. | a–d | NH-3-MeO-phenyl | CO | MeO | | | | |
| 604. | a–d | NH-4-MeO-phenyl | CO | MeO | | | | |
| 605. | a–d | NH-2,4-(MeO)$_2$-phenyl | CO | MeO | | | | |
| 606. | a–d | NH-2,3-(MeO)$_2$-phenyl | CO | MeO | | | | |
| 607. | a–d | NH-2,5-(MeO)$_2$-phenyl | CO | MeO | | | | |
| 608. | a–d | NH-2-Me-phenyl | CO | MeO | | | | |
| 609. | a–d | NH-3-Me-phenyl | CO | MeO | | | | |
| 610. | a–d | NH-4-Me-phenyl | CO | MeO | | | | |
| 611. | a–d | NH-2,4-(Me)$_2$-phenyl | CO | MeO | | | | |
| 612. | a–d | NH-2,5-(Me)$_2$-phenyl | CO | MeO | | | | |
| 613. | a–d | NH-2-CF$_3$-phenyl | CO | MeO | | | | |
| 614. | a–d | NH-3-CF$_3$-phenyl | CO | MeO | | | | |
| 615. | a–d | NH-4-CF$_3$-phenyl | CO | MeO | | | | |
| 616. | a–d | NH-2,4-(CF$_3$)$_2$-phenyl | CO | MeO | | | | |
| 617. | a–d | NH-2,6-Cl$_2$-4-(CF$_3$)$_2$-phenyl | CO | MeO | | | | |
| 618. | a–d | NH-2-CF$_3$O-phenyl | CO | MeO | | | | |
| 619. | a–d | NH-3-CF$_3$O-phenyl | CO | MeO | | | | |
| 620. | a–d | NH-4-CF$_3$O-phenyl | CO | MeO | | | | |
| 621. | a–d | NH-5-F-pyridin-2-yl | CO | MeO | | | | |
| 622. | a–d | NH-5-Cl-pyridin-2-yl | CO | MeO | | | | |
| 623. | a–d | NH-5-F-pyridin-4-yl | CO | MeO | | | | |
| 624. | a–d | NH-5-Cl-pyridin-4-yl | CO | MeO | | | | |
| 625. | a–d | NH-2-CN-phenyl | CO | MeO | | | | |
| 626. | a–d | NH-3-CN-phenyl | CO | MeO | | | | |
| 627. | a–d | NH-4-CN-phenyl | CO | MeO | | | | |
| 628. | a–d | NH-3,5-(CN)$_2$-phenyl | CO | MeO | | | | |
| 629. | a–d | NH-2-CN-4-F-phenyl | CO | MeO | | | | |
| 630. | a–d | NH-4-CN-2-F-phenyl | CO | MeO | | | | |
| 631. | a–d | NH-phenyl | CO | CHO | | | | |
| 632. | a–d | NH-naphth-1-yl | CO | CHO | | | | |
| 633. | a–d | NH-pyridin-2-yl | CO | CHO | | | | |
| 634. | a–d | NH-pyridin-3-yl | CO | CHO | | | | |
| 635. | a–d | NH-pyridin-4-yl | CO | CHO | | | | |
| 636. | a–d | NH-2-F-phenyl | CO | CHO | | | | |
| 637. | a–d | NH-3-F-phenyl | CO | CHO | | | | |
| 638. | a–d | NH-4-F-phenyl | CO | CHO | | | | |
| 639. | a–d | NH-2,3-F$_2$-phenyl | CO | CHO | | | | |
| 640. | a–d | NH-2,4-F$_2$-phenyl | CO | CHO | | | | |
| 641. | a–d | NH-2,5-F$_2$-phenyl | CO | CHO | | | | |
| 642. | a–d | NH-2,6-F$_2$-phenyl | CO | CHO | | | | |
| 643. | a–d | NH-3,4-F$_2$-phenyl | CO | CHO | | | | |
| 644. | a–d | NH-3,5-F$_2$-phenyl | CO | CHO | | | | |
| 645. | a–d | NH-2,4,6-F$_3$-phenyl | CO | CHO | | | | |
| 646. | a–d | NH-2,3,4-F$_3$-phenyl | CO | CHO | | | | |
| 647. | a–d | NH-2-Cl-phenyl | CO | CHO | | | | |
| 648. | a–d | NH-3-Cl-phenyl | CO | CHO | | | | |
| 649. | a–d | NH-4-Cl-phenyl | CO | CHO | | | | |
| 650. | a–d | NH-2,3-Cl$_2$-phenyl | CO | CHO | | | | |
| 651. | a–d | NH-2,4-Cl$_2$-phenyl | CO | CHO | | | | |
| 652. | a–d | NH-2,5-Cl$_2$-phenyl | CO | CHO | | | | |
| 653. | a–d | NH-2,6-Cl$_2$-phenyl | CO | CHO | | | | |
| 654. | a–d | NH-3,4-Cl$_2$-phenyl | CO | CHO | | | | |
| 655. | a–d | NH-3,5-Cl$_2$-phenyl | CO | CHO | | | | |
| 656. | a–d | NH-2,4,6-Cl$_3$-phenyl | CO | CHO | | | | |
| 657. | a–d | NH-2,3,4-Cl$_3$-phenyl | CO | CHO | | | | |
| 658. | a–d | NH-3,4,5-Cl$_3$-phenyl | CO | CHO | | | | |
| 659. | a–d | NH-2-F-4-Cl-phenyl | CO | CHO | | | | |
| 660. | a–d | NH-2-Cl-4-F-phenyl | CO | CHO | | | | |
| 661. | a–d | NH-2-F-3-Cl-phenyl | CO | CHO | | | | |
| 662. | a–d | NH-2-Cl-3-F-phenyl | CO | CHO | | | | |
| 663. | a–d | NH-2-F-5-Cl-phenyl | CO | CHO | | | | |
| 664. | a–d | NH-2-Cl-5-F-phenyl | CO | CHO | | | | |
| 665. | a–d | NH-2-Cl-6-F-phenyl | CO | CHO | | | | |
| 666. | a–d | NH-2-Br-phenyl | CO | CHO | | | | |
| 667. | a–d | NH-3-Br-phenyl | CO | CHO | | | | |
| 668. | a–d | NH-4-Br-phenyl | CO | CHO | | | | |

TABLE 1-continued

|  |  | B | Y | R¹ | Melting point [° C.] | | | |
|---|---|---|---|---|---|---|---|---|
|  |  |  |  |  | a | b | c | d |
| 669. | a–d | NH-2,3-Br$_2$-phenyl | CO | CHO | | | | |
| 670. | a–d | NH-2,4-Br$_2$-phenyl | CO | CHO | | | | |
| 671. | a–d | NH-2,5-Br$_2$-phenyl | CO | CHO | | | | |
| 672. | a–d | NH-2-I-phenyl | CO | CHO | | | | |
| 673. | a–d | NH-3-I-phenyl | CO | CHO | | | | |
| 674. | a–d | NH-4-I-phenyl | CO | CHO | | | | |
| 675. | a–d | NH-2-F-4-MeO-phenyl | CO | CHO | | | | |
| 676. | a–d | NH-2-F-5-MeO-phenyl | CO | CHO | | | | |
| 677. | a–d | NH-2-MeO-phenyl | CO | CHO | | | | |
| 678. | a–d | NH-3-MeO-phenyl | CO | CHO | | | | |
| 679. | a–d | NH-4-MeO-phenyl | CO | CHO | | | | |
| 680. | a–d | NH-2,4-(MeO)$_2$-phenyl | CO | CHO | | | | |
| 681. | a–d | NH-2,3-(MeO)$_2$-phenyl | CO | CHO | | | | |
| 682. | a–d | NH-2,5-(MeO)$_2$-phenyl | CO | CHO | | | | |
| 683. | a–d | NH-2-Me-phenyl | CO | CHO | | | | |
| 684. | a–d | NH-3-Me-phenyl | CO | CHO | | | | |
| 685. | a–d | NH-4-Me-phenyl | CO | CHO | | | | |
| 686. | a–d | NH-2,4-(Me)$_2$-phenyl | CO | CHO | | | | |
| 687. | a–d | NH-2,5-(Me)$_2$-phenyl | CO | CHO | | | | |
| 688. | a–d | NH-2-CF$_3$-phenyl | CO | CHO | | | | |
| 689. | a–d | NH-3-CF$_3$-phenyl | CO | CHO | | | | |
| 690. | a–d | NH-4-CF$_3$-phenyl | CO | CHO | | | | |
| 691. | a–d | NH-2,4-(CF$_3$)$_2$-phenyl | CO | CHO | | | | |
| 692. | a–d | NH-2,6-Cl$_2$-4-(CF$_3$)$_2$-phenyl | CO | CHO | | | | |
| 693. | a–d | NH-2-CF$_3$O-phenyl | CO | CHO | | | | |
| 694. | a–d | NH-3-CF$_3$O-phenyl | CO | CHO | | | | |
| 695. | a–d | NH-4-CF$_3$O-phenyl | CO | CHO | | | | |
| 696. | a–d | NH-5-F-pyridin-2-yl | CO | CHO | | | | |
| 697. | a–d | NH-5-Cl-pyridin-2-yl | CO | CHO | | | | |
| 698. | a–d | NH-5-F-pyridin-4-yl | CO | CHO | | | | |
| 699. | a–d | NH-5-Cl-pyridin-4-yl | CO | CHO | | | | |
| 700. | a–d | NH-2-CN-phenyl | CO | CHO | | | | |
| 701. | a–d | NH-3-CN-phenyl | CO | CHO | | | | |
| 702. | a–d | NH-4-CN-phenyl | CO | CHO | | | | |
| 703. | a–d | NH-3,5-(CN)$_2$-phenyl | CO | CHO | | | | |
| 704. | a–d | NH-2-CN-4-F-phenyl | CO | CHO | | | | |
| 705. | a–d | NH-4-CN-2-F-phenyl | CO | CHO | | | | |
| 706. | a–d | NH-phenyl | CO | NO$_2$ | | | | |
| 707. | a–d | NH-naphth-1-yl | CO | NO$_2$ | | | | |
| 708. | a–d | NH-pyridin-2-yl | CO | NO$_2$ | | | | |
| 709. | a–d | NH-pyridin-3-yl | CO | NO$_2$ | | | | |
| 710. | a–d | NH-pyridin-4-yl | CO | NO$_2$ | | | | |
| 711. | a–d | NH-2-F-phenyl | CO | NO$_2$ | | | | |
| 712. | a–d | NH-3-F-phenyl | CO | NO$_2$ | | | | |
| 713. | a–d | NH-4-F-phenyl | CO | NO$_2$ | | | | |
| 714. | a–d | NH-2,3-F$_2$-phenyl | CO | NO$_2$ | | | | |
| 715. | a–d | NH-2,4-F$_2$-phenyl | CO | NO$_2$ | | | | |
| 716. | a–d | NH-2,5-F$_2$-phenyl | CO | NO$_2$ | | | | |
| 717. | a–d | NH-2,6-F$_2$-phenyl | CO | NO$_2$ | | | | |
| 718. | a–d | NH-3,4-F$_2$-phenyl | CO | NO$_2$ | | | | |
| 719. | a–d | NH-3,5-F$_2$-phenyl | CO | NO$_2$ | | | | |
| 720. | a–d | NH-2,4,6-F$_3$-phenyl | CO | NO$_2$ | | | | |
| 721. | a–d | NH-2,3,4-F$_3$-phenyl | CO | NO$_2$ | | | | |
| 722. | a–d | NH-2-Cl-phenyl | CO | NO$_2$ | | | | |
| 723. | a–d | NH-3-Cl-phenyl | CO | NO$_2$ | | | | |
| 724. | a–d | NH-4-Cl-phenyl | CO | NO$_2$ | | | | |
| 725. | a–d | NH-2,3-Cl$_2$-phenyl | CO | NO$_2$ | | | | |
| 726. | a–d | NH-2,4-Cl$_2$-phenyl | CO | NO$_2$ | | | | |
| 727. | a–d | NH-2,5-Cl$_2$-phenyl | CO | NO$_2$ | | | | |
| 728. | a–d | NH-2,6-Cl$_2$-phenyl | CO | NO$_2$ | | | | |
| 729. | a–d | NH-3,4-Cl$_2$-phenyl | CO | NO$_2$ | | | | |
| 730. | a–d | NH-3,5-Cl$_2$-phenyl | CO | NO$_2$ | | | | |
| 731. | a–d | NH-2,4,6-Cl$_3$-phenyl | CO | NO$_2$ | | | | |
| 732. | a–d | NH-2,3,4-Cl$_3$-phenyl | CO | NO$_2$ | | | | |
| 733 | a–d | NH-3,4,5-Cl$_3$-phenyl | CO | NO$_2$ | | | | |

TABLE 1-continued

|  |  | B | Y | R¹ | a | b | c | d |
|---|---|---|---|---|---|---|---|---|
| | | | | | \multicolumn{4}{c}{Melting point [° C.]} |
| 734. | a–d | NH-2-F-4-Cl-phenyl | CO | $NO_2$ | | | | |
| 735. | a–d | NH-2-Cl-4-F-phenyl | CO | $NO_2$ | | | | |
| 736. | a–d | NH-2-F-3-Cl-phenyl | CO | $NO_2$ | | | | |
| 737. | a–d | NH-2-Cl-3-F-phenyl | CO | $NO_2$ | | | | |
| 738. | a–d | NH-2-F-5-Cl-phenyl | CO | $NO_2$ | | | | |
| 739. | a–d | NH-2-Cl-5-F-phenyl | CO | $NO_2$ | | | | |
| 740. | a–d | NH-2-Cl-6-F-phenyl | CO | $NO_2$ | | | | |
| 741. | a–d | NH-2-Br-phenyl | CO | $NO_2$ | | | | |
| 742. | a–d | NH-3-Br-phenyl | CO | $NO_2$ | | | | |
| 743. | a–d | NH-4-Br-phenyl | CO | $NO_2$ | | | | |
| 744. | a–d | NH-2,3-$Br_2$-phenyl | CO | $NO_2$ | | | | |
| 745. | a–d | NH-2,4-$Br_2$-phenyl | CO | $NO_2$ | | | | |
| 746. | a–d | NH-2,5-$Br_2$-phenyl | CO | $NO_2$ | | | | |
| 747. | a–d | NH-2-I-phenyl | CO | $NO_2$ | | | | |
| 748. | a–d | NH-3-I-phenyl | CO | $NO_2$ | | | | |
| 749. | a–d | NH-4-I-phenyl | CO | $NO_2$ | | | | |
| 750. | a–d | NH-2-F-4-MeO-phenyl | CO | $NO_2$ | | | | |
| 751. | a–d | NH-2-F-5-MeO-phenyl | CO | $NO_2$ | | | | |
| 752. | a–d | NH-2-MeO-phenyl | CO | $NO_2$ | | | | |
| 753. | a–d | NH-3-MeO-phenyl | CO | $NO_2$ | | | | |
| 754. | a–d | NH-4-MeO-phenyl | CO | $NO_2$ | | | | |
| 755 | a–d | NH-2,4-$(MeO)_2$-phenyl | CO | $NO_2$ | | | | |
| 756. | a–d | NH-2,3-$(MeO)_2$-phenyl | CO | $NO_2$ | | | | |
| 757 | a–d | NH-2,5-$(MeO)_2$-phenyl | CO | $NO_2$ | | | | |
| 758. | a–d | NH-2-Me-phenyl | CO | $NO_2$ | | | | |
| 759. | a–d | NH-3-Me-phenyl | CO | $NO_2$ | | | | |
| 760. | a–d | NH-4-Me-phenyl | CO | $NO_2$ | | | | |
| 761. | a–d | NH-2,4-$(Me)_2$-phenyl | CO | $NO_2$ | | | | |
| 762. | a–d | NH-2,5-$(Me)_2$-phenyl | CO | $NO_2$ | | | | |
| 763. | a–d | NH-2-$CF_3$-phenyl | CO | $NO_2$ | | | | |
| 764. | a–d | NH-3-$CF_3$-phenyl | CO | $NO_2$ | | | | |
| 765. | a–d | NH-4-$CF_3$-phenyl | CO | $NO_2$ | | | | |
| 766. | a–d | NH-2,4-$(CF_3)_2$-phenyl | CO | $NO_2$ | | | | |
| 767. | a–d | NH-2,6-$Cl_2$-4-$(CF_3)_2$-phenyl | CO | $NO_2$ | | | | |
| 768. | a–d | NH-2-$CF_3$O-phenyl | CO | $NO_2$ | | | | |
| 769. | a–d | NH-3-$CF_3$O-phenyl | CO | $NO_2$ | | | | |
| 770. | a–d | NH-4-$CF_3$O-phenyl | CO | $NO_2$ | | | | |
| 771. | a–d | NH-5-F-pyridin-2-yl | CO | $NO_2$ | | | | |
| 772. | a–d | NH-5-Cl-pyridin-2-yl | CO | $NO_2$ | | | | |
| 773. | a–d | NH-5-F-pyridin-4-yl | CO | $NO_2$ | | | | |
| 774. | a–d | NH-5-Cl-pyridin-4-yl | CO | $NO_2$ | | | | |
| 775. | a–d | NH-2-CN-phenyl | CO | $NO_2$ | | | | |
| 776. | a–d | NH-3-CN-phenyl | CO | $NO_2$ | | | | |
| 777. | a–d | NH-4-CN-phenyl | CO | $NO_2$ | | | | |
| 778. | a–d | NH-3,5-$(CN)_2$-phenyl | CO | $NO_2$ | | | | |
| 779. | a–d | NH-2-CN-4-F-phenyl | CO | $NO_2$ | | | | |
| 780. | a–d | NH-4-CN-2-F-phenyl | CO | $NO_2$ | | | | |
| 781. | a–d | $NH_2$ | $CH_2$ | CN | | | | |
| 782. | a–d | $NH_2$ | $CH_2$ | Me | | | | |
| 783. | a–d | $NH_2$ | $CH_2$ | MeO | yellow resin | | | |
| 784. | a–d | $NH_2$ | $CH_2$ | CHO | | | | |
| 785. | a–d | $NH_2$ | $CH_2$ | $NO_2$ | | | | |
| 786. | a–d | NH—COMe | $CH_2$ | CN | | | | |
| 787. | a–d | NH—COEt | $CH_2$ | CN | | | | |
| 788. | a–d | NH—COnPr | $CH_2$ | CN | | | | |
| 789. | a–d | NH—COiPr | $CH_2$ | CN | | | | |
| 790. | a–d | NH—COcPr | $CH_2$ | CN | | | | |
| 791. | a–d | NH—COnBu | $CH_2$ | CN | | | | |
| 792. | a–d | NH—COiBu | $CH_2$ | CN | | | | |
| 793. | a–d | NH—COcBu | $CH_2$ | CN | | | | |
| 794. | a–d | NH—COcPentyl | $CH_2$ | CN | | | | |
| 795. | a–d | NH—COcHexyl | $CH_2$ | CN | | | | |
| 796. | a–d | NH—$COCF_3$ | $CH_2$ | CN | | | | |
| 797. | a–d | NH—$COCHF_2$ | $CH_2$ | CN | | | | |
| 798. | a–d | NH—$COCH_2F$ | $CH_2$ | CN | | | | |
| 799. | a–d | NH—$COCCl_3$ | $CH_2$ | CN | | | | |
| 800. | a–d | NH—$COCHCl_2$ | $CH_2$ | CN | | | | |

TABLE 1-continued

| | | B | Y | R¹ | Melting point [° C.] | | | |
|---|---|---|---|---|---|---|---|---|
| | | | | | a | b | c | d |
| 801. | a–d | NH—COCH₂Cl | CH₂ | CN | | | | |
| 802. | a–d | NH—COCH₂OMe | CH₂ | CN | | | | |
| 803. | a–d | NH—COCH(OMe)₂ | CH₂ | CN | | | | |
| 804. | a–d | NH—COCH₂OEt | CH₂ | CN | | | | |
| 805. | a–d | NH—COCH(OEt)₂ | CH2 | CN | | | | |
| 806. | a–d | NH—COPh | CH₂ | CN | | | | |
| 807. | a–d | NH—CO(2-F-Ph) | CH₂ | CN | | | | |
| 808. | a–d | NH—CO(3-F-Ph) | CH₂ | CN | | | | |
| 809. | a–d | NH—CO(4-F-Ph) | CH₂ | CN | | | | |
| 810. | a–d | NH—CO(2,4-F₂-Ph) | CH₂ | CN | | | | |
| 811. | a–d | NH—CO(2,4,6-F₃-Ph) | CH₂ | CN | | | | |
| 812. | a–d | NH—CO(2-Cl-Ph) | CH₂ | CN | | | | |
| 813. | a–d | NH—CO(3-Cl-Ph) | CH₂ | CN | | | | |
| 814. | a–d | NH—CO(4-Cl-Ph) | CH₂ | CN | | | | |
| 815. | a–d | NH—CO(2,4-Cl₂-Ph) | CH₂ | CN | | | | |
| 816. | a–d | NH—CO(2,4,6-Cl₃-Ph) | CH₂ | CN | | | | |
| 817. | a–d | NH—COBn | CH₂ | CN | | | | |
| 818. | a–d | NH—CO(2-F-4-Cl-Ph) | CH₂ | CN | | | | |
| 819. | a–d | NH—CO(2-Cl-4-F-Ph) | CH₂ | CN | | | | |
| 820. | a–d | NH—CO(2-Me-Ph) | CH₂ | CN | | | | |
| 821. | a–d | NH—CO(3-Me-Ph) | CH₂ | CN | | | | |
| 822. | a–d | NH—CO(4-Me-Ph) | CH₂ | CN | | | | |
| 823. | a–d | NH—CO(2-CF₃-Ph) | CH₂ | CN | | | | |
| 824. | a–d | NH—CO(3-CF₃-Ph) | CH₂ | CN | | | | |
| 825. | a–d | NH—CO(4-CF₃-Ph) | CH₂ | CN | | | | |
| 826. | a–d | NH—COMe | CH₂ | Me | | | | |
| 827. | a–d | NH—COEt | CH₂ | Me | | | | |
| 828. | a–d | NH—COnPr | CH₂ | Me | | | | |
| 829. | a–d | NH—COiPr | CH₂ | Me | | | | |
| 830. | a–d | NH—COcPr | CH₂ | Me | | | | |
| 831. | a–d | NH—COnBu | CH₂ | Me | | | | |
| 832. | a–d | NH—COiBu | CH₂ | Me | | | | |
| 833. | a–d | NH—COcBu | CH₂ | Me | | | | |
| 834. | a–d | NH—COcPentyl | CH₂ | Me | | | | |
| 835. | a–d | NH—COcHexyl | CH₂ | Me | | | | |
| 836. | a–d | NH—COCF₃ | CH₂ | Me | | | | |
| 837. | a–d | NH—COCHF₂ | CH₂ | Me | | | | |
| 838. | a–d | NH—COCH₂F | CH₂ | Me | | | | |
| 839. | a–d | NH—COCCl₃ | CH₂ | Me | | | | |
| 840. | a–d | NH—COOHCl₂ | CH₂ | Me | | | | |
| 841. | a–d | NH—COCH₂Cl | CH₂ | Me | | | | |
| 842. | a–d | NH—COOH₂OMe | CH₂ | Me | | | | |
| 843. | a–d | NH—COOH(OMe)₂ | CH₂ | Me | | | | |
| 844. | a–d | NH—COOH₂OEt | CH₂ | Me | | | | |
| 845. | a–d | NH—COOH(OEt)₂ | CH₂ | Me | | | | |
| 846. | a–d | NH—COPh | CH₂ | Me | | | | |
| 847. | a–d | NH—CO(2-F-Ph) | CH₂ | Me | | | | |
| 848. | a–d | NH—CO(3-F-Ph) | CH₂ | Me | | | | |
| 849. | a–d | NH—CO(4-F-Ph) | CH₂ | Me | | | | |
| 850. | a–d | NH—CO(2,4-F₂-Ph) | CH₂ | Me | | | | |
| 851. | a–d | NH—CO(2,4,6-F₃-Ph) | CH₂ | Me | | | | |
| 852. | a–d | NH—CO(2-Cl-Ph) | CH₂ | Me | | | | |
| 853. | a–d | NH—CO(3-Cl-Ph) | CH₂ | Me | | | | |
| 854. | a–d | NH—CO(4-Cl-Ph) | CH₂ | Me | | | | |
| 855. | a–d | NH—CO(2,4-Cl₂-Ph) | CH₂ | Me | | | | |
| 856. | a–d | NH—CO(2,4,6-Cl₃-Ph) | CH₂ | Me | | | | |
| 857. | a–d | NH—COBn | CH₂ | Me | | | | |
| 858. | a–d | NH—CO(2-F-4-Cl-Ph) | CH₂ | Me | | | | |
| 859. | a–d | NH—CO(2-Cl-4-F-Ph) | CH₂ | Me | | | | |
| 860. | a–d | NH—CO(2-Me-Ph) | CH₂ | Me | | | | |
| 861. | a–d | NH—CO(3-Me-Ph) | CH₂ | Me | | | | |
| 862. | a–d | NH—CO(4-Me-Ph) | CH₂ | Me | | | | |
| 863. | a–d | NH—CO(2-CF₃-Ph) | CH₂ | Me | | | | |
| 864. | a–d | NH—CO(3-CF₃-Ph) | CH₂ | Me | | | | |
| 865. | a–d | NH—CO(4-CF₃-Ph) | CH₂ | Me | | | | |
| 866. | a–d | NH—COMe | CH₂ | MeO | | | | |
| 867. | a–d | NH—COEt | CH₂ | MeO | | | | |
| 868. | a–d | NH—COnPr | CH₂ | MeO | | | | |
| 869. | a–d | NH—COiPr | CH₂ | MeO | 86 | | | |
| 870. | a–d | NH—COcPr | CH₂ | MeO | 86 | | | |
| 871. | a–d | NH—COnBu | CH₂ | MeO | | | | |
| 872. | a–d | NH—COiBu | CH₂ | MeO | | | | |
| 873. | a–d | NH—COcBu | CH₂ | MeO | | | | |
| 874. | a–d | NH—COcPentyl | CH₂ | MeO | | | | |
| 875. | a–d | NH—COcHexyl | CH₂ | MeO | | | | |

TABLE 1-continued

|  | | B | Y | R¹ | Melting point [° C.] | | | |
|---|---|---|---|---|---|---|---|---|
|  | | | | | a | b | c | d |
| 876. | a–d | NH—COCF₃ | CH₂ | MeO | brown semi-crystalline solid | | | |
| 877. | a–d | NH—COOHF₂ | CH₂ | MeO | | | | |
| 878. | a–d | NH—COOH₂F | CH₂ | MeO | | | | |
| 879. | a–d | NH—COCCl₃ | CH₂ | MeO | | | | |
| 880. | a–d | NH—COCHCl₂ | CH₂ | MeO | | | | |
| 881. | a–d | NH—COCH₂Cl | CH₂ | MeO | | | | |
| 882. | a–d | NH—COOH₂OMe | CH₂ | MeO | | | | |
| 883. | a–d | NH—COOH(OMe)₂ | CH₂ | MeO | | | | |
| 884. | a–d | NH—COOH₂OEt | CH₂ | MeO | | | | |
| 885. | a–d | NH—COOH(OEt)₂ | CH₂ | MeO | | | | |
| 886. | a–d | NH—COPh | CH₂ | MeO | | | | |
| 887. | a–d | NH—CO(2-F-Ph) | CH₂ | MeO | | | | |
| 888. | a–d | NH—CO(3-F-Ph) | CH₂ | MeO | | | | |
| 889. | a–d | NH—CO(4-F-Ph) | CH₂ | MeO | | | | |
| 890. | a–d | NH—CO(2,4-F₂-Ph) | CH₂ | MeO | | | | |
| 891. | a–d | NH—CO(2,4,6-F₃-Ph) | CH₂ | MeO | | | | |
| 892. | a–d | NH—CO(2-Cl-Ph) | CH₂ | MeO | | | | |
| 893. | a–d | NH—CO(3-Cl-Ph) | CH₂ | MeO | | | | |
| 894. | a–d | NH—CO(4-Cl-Ph) | CH₂ | MeO | | | | |
| 895. | a–d | NH—CO(2,4-Cl₂-Ph) | CH₂ | MeO | | | | |
| 896. | a–d | NH—CO(2,4,6-Cl₃-Ph) | CH₂ | MeO | | | | |
| 897. | a–d | NH—COBn | CH₂ | MeO | | | | |
| 898. | a–d | NH—CO(2-F-4-Cl-Ph) | CH₂ | MeO | | | | |
| 899. | a–d | NH—CO(2-Cl-4-F-Ph) | CH₂ | MeO | | | | |
| 900. | a–d | NH—CO(2-Me-Ph) | CH₂ | MeO | | | | |
| 901. | a–d | NH—CO(3-Me-Ph) | CH₂ | MeO | | | | |
| 902. | a–d | NH—CO(4-Me-Ph) | CH₂ | MeO | | | | |
| 903. | a–d | NH—CO(2-CF₃-Ph) | CH₂ | MeO | | | | |
| 904. | a–d | NH—CO(3-CF₃-Ph) | CH₂ | MeO | | | | |
| 905. | a–d | NH—CO(4-CF₃-Ph-CO) | CH₂ | MeO | | | | |
| 906. | a–d | NH—COMe | CH₂ | CHO | | | | |
| 907. | a–d | NH—COEt | CH₂ | CHO | | | | |
| 908. | a–d | NH—COnPr | CH₂ | CHO | | | | |
| 909. | a–d | NH—COiPr | CH₂ | CHO | | | | |
| 910. | a–d | NH—COcPr | CH₂ | CHO | | | | |
| 911. | a–d | NH—COnBu | CH₂ | CHO | | | | |
| 912. | a–d | NH—CO,Bu | CH₂ | CHO | | | | |
| 913. | a–d | NH—COcBu | CH₂ | CHO | | | | |
| 914. | a–d | NH—COcPentyl | CH₂ | CHO | | | | |
| 915. | a–d | NH—COcHexyl | CH₂ | CHO | | | | |
| 916. | a–d | NH—COCF₃ | CH₂ | CHO | | | | |
| 917. | a–d | NH—COCHF₂ | CH₂ | CHO | | | | |
| 918. | a–d | NH—COOH₂F | CH₂ | CHO | | | | |
| 919. | a–d | NH—COCCl₃ | CH₂ | CHO | | | | |
| 920. | a–d | NH—COCHCl₂ | CH₂ | CHO | | | | |
| 921. | a–d | NH—COCH₂Cl | CH₂ | CHO | | | | |
| 922. | a–d | NH—COOH₂OMe | CH₂ | CHO | | | | |
| 923. | a–d | NH—COOH(OMe)₂ | CH₂ | CHO | | | | |
| 924. | a–d | NH—COOH₂OEt | CH₂ | CHO | | | | |
| 925. | a–d | NH—COOH(OEt)₂ | CH₂ | CHO | | | | |
| 926. | a–d | NH—COPh | CH₂ | CHO | | | | |
| 927. | a–d | NH—CO(2-F-Ph) | CH₂ | CHO | | | | |
| 928. | a–d | NH—CO(3-F-Ph) | CH₂ | CHO | | | | |
| 929. | a–d | NH—CO(4-F-Ph) | CH₂ | CHO | | | | |
| 930. | a–d | NH—CO(2,4-F₂-Ph) | CH₂ | CHO | | | | |
| 931. | a–d | NH—CO(2,4,6-F₃-Ph) | CH₂ | CHO | | | | |
| 932. | a–d | NH—CO(2-Cl-Ph) | CH₂ | CHO | | | | |
| 933. | a–d | NH—CO(3-Cl-Ph) | CH₂ | CHO | | | | |
| 934. | a–d | NH—CO(4-Cl-Ph) | CH₂ | CHO | | | | |
| 935. | a–d | NH—CO(2,4-Cl₂-Ph) | CH₂ | CHO | | | | |
| 936. | a–d | NH—CO(2,4,6-Cl₃-Ph) | CH₂ | CHO | | | | |
| 937. | a–d | NH—COBn | CH₂ | CHO | | | | |
| 938. | a–d | NH—CO(2-F-4-Cl-Ph) | CH₂ | CHO | | | | |
| 939. | a–d | NH—CO(2-Cl-4-F-Ph) | CH₂ | CHO | | | | |
| 940. | a–d | NH—CO(2-Me-Ph) | CH₂ | CHO | | | | |
| 941. | a–d | NH—CO(3-Me-Ph) | CH₂ | CHO | | | | |
| 942. | a–d | NH—CO(4-Me-Ph) | CH₂ | CHO | | | | |
| 943. | a–d | NH—CO(2-CF₃-Ph) | CH₂ | CHO | | | | |
| 944. | a–d | NH—CO(3-CF₃-Ph) | CH₂ | CHO | | | | |
| 945. | a–d | NH—CO(4-CF₃-Ph) | CH₂ | CHO | | | | |
| 946. | a–d | NH—COMe | CH₂ | NO₂ | | | | |

TABLE 1-continued

| | | B | Y | R¹ | Melting point [° C.] | | | |
|---|---|---|---|---|---|---|---|---|
| | | | | | a | b | c | d |
| 947. | a–d | NH—COEt | CH$_2$ | NO$_2$ | | | | |
| 948. | a–d | NH—COnPr | CH$_2$ | NO$_2$ | | | | |
| 949. | a–d | NH—COiPr | CH$_2$ | NO$_2$ | | | | |
| 950. | a–d | NH—COcPr | CH$_2$ | NO$_2$ | | | | |
| 951. | a–d | NH—COnBu | CH$_2$ | NO$_2$ | | | | |
| 952. | a–d | NH—COiBu | CH$_2$ | NO$_2$ | | | | |
| 953. | a–d | NH—COcBu | CH$_2$ | NO$_2$ | | | | |
| 954. | a–d | NH—COcPentyl | CH$_2$ | NO$_2$ | | | | |
| 955. | a–d | NH—COcHexyl | CH$_2$ | NO$_2$ | | | | |
| 956. | a–d | NH—COCF$_3$ | CH$_2$ | NO$_2$ | | | | |
| 957. | a–d | NH—COOHF$_2$ | CH$_2$ | NO$_2$ | | | | |
| 958. | a–d | NH—COOH$_2$F | CH$_2$ | NO$_2$ | | | | |
| 959. | a–d | NH—COCCl$_3$ | CH$_2$ | NO$_2$ | | | | |
| 960. | a–d | NH—COCHCl$_2$ | CH$_2$ | NO$_2$ | | | | |
| 961. | a–d | NH—COOH$_2$Cl | CH$_2$ | NO$_2$ | | | | |
| 962. | a–d | NH—COOH$_2$OMe | CH$_2$ | NO$_2$ | | | | |
| 963. | a–d | NH—COOH(OMe)$_2$ | CH$_2$ | NO$_2$ | | | | |
| 964. | a–d | NH—COOH$_2$OEt | CH$_2$ | NO$_2$ | | | | |
| 965. | a–d | NH—COOH(OEt)$_2$ | CH$_2$ | NO$_2$ | | | | |
| 966. | a–d | NH—COPh | CH$_2$ | NO$_2$ | | | | |
| 967. | a–d | NH—CO(2-F-Ph) | CH$_2$ | NO$_2$ | | | | |
| 968. | a–d | NH—CO(3-F-Ph) | CH$_2$ | NO$_2$ | | | | |
| 969. | a–d | NH—CO(4-F-Ph) | CH$_2$ | NO$_2$ | | | | |
| 970. | a–d | NH—CO(2,4-F$_2$-Ph) | CH$_2$ | NO$_2$ | | | | |
| 971. | a–d | NH—CO(2,4,6-F$_3$-Ph) | CH$_2$ | NO$_2$ | | | | |
| 972. | a–d | NH—CO(2-Cl-Ph) | CH$_2$ | NO$_2$ | | | | |
| 973. | a–d | NH—CO(3-Cl-Ph) | CH$_2$ | NO$_2$ | | | | |
| 974. | a–d | NH—CO(4-Cl-Ph) | CH$_2$ | NO$_2$ | | | | |
| 975. | a–d | NH—CO(2,4-Cl$_2$-Ph) | CH$_2$ | NO$_2$ | | | | |
| 976. | a–d | NH—CO(2,4,6-Cl$_3$-Ph) | CH$_2$ | NO$_2$ | | | | |
| 977. | a–d | NH—COBn | CH$_2$ | NO$_2$ | | | | |
| 978. | a–d | NH—CO(2-F-4-Cl-Ph) | CH$_2$ | NO$_2$ | | | | |
| 979. | a–d | NH—CO(2-Cl-4-F-Ph) | CH$_2$ | NO$_2$ | | | | |
| 980. | a–d | NH—CO(2-Me-Ph) | CH$_2$ | NO$_2$ | | | | |
| 981. | a–d | NH—CO(3-Me-Ph) | CH$_2$ | NO$_2$ | | | | |
| 982. | a–d | NH—CO(4-Me-Ph) | CH$_2$ | NO$_2$ | | | | |
| 983. | a–d | NH—CO(2-CF$_3$-Ph) | CH$_2$ | NO$_2$ | | | | |
| 984. | a–d | NH—CO(3-CF$_3$-Ph) | CH$_2$ | NO$_2$ | | | | |
| 985. | a–d | NH—CO(4-CF$_3$-Ph) | CH$_2$ | NO$_2$ | | | | |
| 986. | a–d | NH—Me | CO | CN | | | | |
| 987. | a–d | NH—Me | CO | Me | | | | |
| 988. | a–d | NH—Me | CO | MeO | | | | |
| 989. | a–d | NH—Me | CO | CHO | | | | |
| 990. | a–d | NH—Me | CO | NO$_2$ | | | | |
| 991. | a–d | NH—Et | CO | CN | | | | |
| 992. | a–d | NH—Et | CO | Me | | | | |
| 993. | a–d | NH—Et | CO | MeO | | | | |
| 994. | a–d | NH—Et | CO | CHO | | | | |
| 995. | a–d | NH—Et | CO | NO$_2$ | | | | |
| 996. | a–d | NH—CH$_2$CHF$_2$ | CO | CN | | | | |
| 997. | a–d | NH—CH$_2$CHF$_2$ | CO | Me | | | | |
| 998. | a–d | NH—CH$_2$CHF$_2$ | CO | MeO | | | | |
| 999. | a–d | NH—CH$_2$CHF$_2$ | CO | CHO | | | | |
| 1000. | a–d | NH—CH$_2$CHF$_2$ | CO | NO$_2$ | | | | |
| 1001. | a–d | NH—CH$_2$CH$_2$CF$_3$ | CO | CN | | | | |
| 1002. | a–d | NH—CH$_2$CH$_2$CF$_3$ | CO | Me | | | | |
| 1003. | a–d | NH—CH$_2$CH$_2$CF$_3$ | CO | MeO | | | | |
| 1004. | a–d | NH—CH$_2$CH$_2$CF$_3$ | CO | CHO | | | | |
| 1005. | a–d | NH—CH$_2$CH$_2$CF$_3$ | CO | NO$_2$ | | | | |
| 1006. | a–d | NH—CH$_2$CF$_3$CO | CN | | | | | |
| 1007. | a–d | NH—OH$_2$CF$_3$CO | Me | | | | | |
| 1008. | a–d | NH—OH$_2$CF$_3$ | CO | MeO | | | | |
| 1009. | a–d | NH—OH$_2$CF$_3$ | CO | CHO | | | | |
| 1010. | a–d | NH—OH$_2$CF$_3$ | CO | NO$_2$ | | | | |
| 1011. | a–d | NH—Bn | CO | CN | | | | |
| 1012. | a–d | NH—Bn | CO | Me | | | | |
| 1013. | a–d | NH—Bn | CO | MeO | | | | |
| 1014. | a–d | NH—Bn | CO | CHO | | | | |
| 1015. | a–d | NH—Bn | CO | NO$_2$ | | | | |
| 1016. | a–d | NH-cHexyl | CO | CN | | | | |
| 1017. | a–d | NH-cHexyl | CO | Me | | | | |
| 1018. | a–d | NH-cHexyl | CO | MeO | | | | |
| 1019. | a–d | NH-cHexyl | CO | CHO | | | | |
| 1020. | a–d | NH-cHexyl | CO | NO$_2$ | | | | |
| 1021. | a–d | NH-cPentyl | CO | CN | | | | |

TABLE 1-continued

| | B | Y | R$^1$ | Melting point [° C.] | | | |
|---|---|---|---|---|---|---|---|
| | | | | a | b | c | d |
| 1022. a–d | NH-cPentyl | CO | Me | | | | |
| 1023. a–d | NH-cPentyl | CO | MeO | | | | |
| 1024. a–d | NH-cPentyl | CO | CHO | | | | |
| 1025. a–d | NH-cPentyl | CO | NO$_2$ | | | | |
| 1026. a–d | NH-cBu | CO | CN | | | | |
| 1027. a–d | NH-cBu | CO | Me | | | | |
| 1028. a–d | NH-cBu | CO | MeO | | | | |
| 1029. a–d | NH-cBu | CO | CHO | | | | |
| 1030. a–d | NH-cBu | CO | NO$_2$ | | | | |
| 1031. a–d | NH-nBu | CO | CN | | | | |
| 1032. a–d | NH-nBu | CO | Me | | | | |
| 1033. a–d | NH-nBu | CO | MeO | | | | |
| 1034. a–d | NH-nBu | CO | CHO | | | | |
| 1035. a–d | NH-nBu | CO | NO$_2$ | | | | |
| 1036. a–d | NH-nPr | CO | CN | | | | |
| 1037. a–d | NH-nPr | CO | Me | | | | |
| 1038. a–d | NH-nPr | CO | MeO | | | | |
| 1039. a–d | NH-nPr | CO | CHO | | | | |
| 1040. a–d | NH-nPr | CO | NO$_2$ | | | | |
| 1041. a–d | NH-cPr | CO | CN | | | | |
| 1042. a–d | NH-cPr | CO | Me | | | | |
| 1043. a–d | NH-cPr | CO | MeO | | | | |
| 1044. a–d | NH-cPr | CO | CHO | | | | |
| 1045. a–d | NH-cPr | CO | NO$_2$ | | | | |
| 1046. a–d | NH-iPr | CO | CN | | | | |
| 1047. a–d | NH-iPr | CO | Me | | | | |
| 1048. a–d | NH-iPr | CO | MeO | | | | |
| 1049. a–d | NH-iPr | CO | CHO | | | | |
| 1050. a–d | NH-iPr | CO | NO$_2$ | | | | |
| 1051. a–d | NH—OH$_2$CH=CH$_2$ | CO | CN | | | | |
| 1052. a–d | NH—CH$_2$CH=CH$_2$ | CO | Me | | | | |
| 1053. a–d | NH—CH$_2$CH=CH$_2$ | CO | MeO | | | | |
| 1054. a–d | NH—CH$_2$CH=CH$_2$ | CO | CHO | | | | |
| 1055. a–d | NH—CH$_2$CH=CH$_2$ | CO | NO$_2$ | | | | |
| 1056. a–d | CH$_2$CH=CH$_2$ | O | CN | yellow oil | | | |
| 1057. a–d | CH$_2$CH=CHMe | O | CN | | | | |
| 1058. a–d | CH$_2$CH=CMe$_2$ | O | CN | orange oil | | | |
| 1059. a–d | (E)-CH$_2$CH=CH—CF$_3$ | O | CN | 115 | | | |
| 1060. a–d | CH$_2$CCl=CH$_2$ | O | CN | 83 | | | |
| 1061. a–d | CH$_2$CBr=CHBr | O | CN | | | | |
| 1062. a–d | (Z)-CH$_2$CH=CClMe | O | CN | semi-crystalline colorless | | | |
| 1063. a–d | CH$_2$CH=CH—OH$_2$OEt | O | CN | | | | |
| 1064. a–d | CH$_2$CH=CH—CF$_2$Br | O | CN | | | | |
| 1065. a–d | CH$_2$CH=CHBr | O | CN | | | | |
| 1066. a–d | CH$_2$CH=CHPh | O | CN | yellow resin | | | |
| 1067. a–d | CH$_2$CH=CHEt | O | CN | | | | |
| 1068. a–d | CH$_2$CMeCH$_2$ | O | CN | brown resin | | | |
| 1069. a–d | CH$_2$CCl=CH—CF$_3$ | O | CN | | | | |
| 1070. a–d | (Z)-CH$_2$CH=CCl—CF$_3$ | O | CN | colorless resin | | | |
| 1071. a–d | CH$_2$CH=CCl$_2$ | O | CN | light-brown resin | | semi crystalline brown | |
| 1072. a–d | CH$_2$CH=CH$_2$ | O | Me | | | | |
| 1073. a–d | (E)-CH$_2$CH=CHMe | O | Me | colorless oil | | | |
| 1074. a–d | CH$_2$CH=CMe$_2$ | O | Me | | | | |
| 1075. a–d | CH$_2$CH=CH—CF$_3$ | O | Me | | | | |
| 1076. a–d | CH$_2$CCl=CH$_2$ | O | Me | | | | |
| 1077. a–d | CH$_2$CBr=CHBr | O | Me | | | | |
| 1078. a–d | CH$_2$CHCClMe | O | Me | | | | |
| 1079. a–d | CH$_2$CH=CH-CH$_2$OEt | O | Me | | | | |
| 1080. a–d | CH$_2$CH=CH-CF$_2$Br | O | Me | | | | |
| 1081. a–d | CH$_2$CHCHBr | O | Me | | | | |
| 1082. a–d | CH$_2$CHCHPh | O | Me | | | | |
| 1083. a–d | CH$_2$CH=CHEt | O | Me | | | | |
| 1084. a–d | CH$_2$CMe=CH$_2$ | O | Me | | | | |
| 1085. a–d | CH$_2$Cl=CH—CF$_3$ | O | Me | | | | |
| 1086. a–d | CH$_2$CH=CCl—CF$_3$ | O | Me | | | | |
| 1087. a–d | CH$_2$CH=CCl$_2$ | O | Me | | | | |
| 1088. a–d | CH$_2$CH=CH$_2$ | O | MeO | | | | |

TABLE 1-continued

| | | B | Y | R¹ | Melting point [° C.] a | b | c | d |
|---|---|---|---|---|---|---|---|---|
| 1089. | a–d | $CH_2CH=CHMe$ | O | MeO | | | | |
| 1090. | a–d | $CH_2CH=CMe_2$ | O | MeO | | | | |
| 1091. | a–d | $CH_2CH=CH-CF_3$ | O | MeO | | | | |
| 1092. | a–d | $CH_2CCl=CH_2$ | O | MeO | | | | |
| 1093. | a–d | $CH_2CBr=CHBr$ | O | MeO | | | | |
| 1094. | a–d | $CH_2CHCClMe$ | O | MeO | | | | |
| 1095. | a–d | $CH_2CH=CH-CH_2OEt$ | O | MeO | | | | |
| 1096. | a–d | $CH_2CH=CH-CF_2Br$ | O | MeO | | | | |
| 1097. | a–d | $CH_2CH=CHBr$ | O | MeO | | | | |
| 1098. | a–d | $CH_2CH=CHPh$ | O | MeO | | | | |
| 1099. | a–d | $CH_2CH=CHEt$ | O | MeO | | | | |
| 1100. | a–d | $CH_2CMe=CH_2$ | O | MeO | | | | |
| 1101. | a–d | $CH_2ClCH-CF_3$ | O | MeO | | | | |
| 1102. | a–d | $CH_2CH=CCl-CF_3$ | O | MeO | | | | |
| 1103. | a–d | $CH_2CH=CCl_2$ | O | MeO | | | | |
| 1104. | a–d | $CH_2CHCH_2$ | O | CHO | | | | |
| 1105. | a–d | $CH_2CH=CHMe$ | O | CHO | | | | |
| 1106. | a–d | $CH_2CH=CMe_2$ | O | CHO | | | | |
| 1107. | a–d | $CH_2CHCH-CF_3$ | O | CHO | | | | |
| 1108. | a–d | $CH_2CCl=CH_2$ | O | CHO | | | | |
| 1109. | a–d | $CH_2CBr=CHBr$ | O | CHO | | | | |
| 1110. | a–d | $CH_2CH=CClMe$ | O | CHO | | | | |
| 1111. | a–d | $CH_2CH=CH-CH_2OEt$ | O | CHO | | | | |
| 1112. | a–d | $CH_2CH=CH-CF_2Br$ | O | CHO | | | | |
| 1113. | a–d | $CH_2CH=CHBr$ | O | CHO | | | | |
| 1114. | a–d | $CH_2CH=CHPh$ | O | CHO | | | | |
| 1115. | a–d | $CH_2CH=CHEt$ | O | CHO | | | | |
| 1116. | a–d | $CH_2CMe=CH_2$ | O | CHO | | | | |
| 1117. | a–d | $CH_2Cl=CH-CF_3$ | O | CHO | | | | |
| 1118. | a–d | $CH_2CH=CCl-CF_3$ | O | CHO | | | | |
| 1119. | a–d | $CH_2CH=CCl_2$ | O | CHO | | | | |
| 1120. | a–d | $CH_2CH=CH_2$ | O | $NO_2$ | | | | |
| 1121. | a–d | $CH_2CH=CHMe$ | O | $NO_2$ | | | | |
| 1122. | a–d | $OH_2OH=CMe_2$ | O | $NO_2$ | | | | |
| 1123. | a–d | $CH_2CH=CH-CF_3$ | O | $NO_2$ | | | | |
| 1124. | a–d | $CH_2CCl=CH_2$ | O | $NO_2$ | | | | |
| 1125. | a–d | $CH_2CBr=CHBr$ | O | $NO_2$ | | | | |
| 1126. | a–d | $CH_2CH=CClMe$ | O | $NO_2$ | | | | |
| 1127. | a–d | $CH_2CH=CH-CH_2OEt$ | O | $NO_2$ | | | | |
| 1128. | a–d | $CH_2OH=CH-CF_2Br$ | O | $NO_2$ | | | | |
| 1129. | a–d | $CH_2CH=CHBr$ | O | $NO_2$ | | | | |
| 1130. | a–d | $CH_2CH=CHPh$ | O | $NO_2$ | | | | |
| 1131. | a–d | $CH_2CH=CHEt$ | O | $NO_2$ | | | | |
| 1132. | a–d | $CH_2CMe=CH_2$ | O | $NO_2$ | | | | |
| 1133. | a–d | $CH_2Cl=CH-CF_3$ | O | $NO_2$ | | | | |
| 1134. | a–d | $CH_2CH=CCl-CF_3$ | O | $NO_2$ | | | | |
| 1135. | a–d | $CH_2CH=CCl_2$ | O | $NO_2$ | | | | |
| 1136. | a–d | F | bond | CN | see Ex. 2 | | yellow oil | |
| 1137. | a–d | Cl | bond | CN | | | | |
| 1138. | a–d | Br | bond | CN | | | | |
| 1139. | a–d | I | bond | CN | | | | |
| 1140. | a–d | CN | bond | CN | see Ex. 6 | | brown wax | 131 |
| 1141. | a–d | F | bond | Me | | | | |
| 1142. | a–d | Cl | bond | Me | | | | |
| 1143. | a–d | Br | bond | Me | | | | |
| 1144. | a–d | I | bond | Me | | | | |
| 1145. | a–d | CN | bond | Me | 92 | | | |
| 1146. | a–d | F | bond | MeO | | | | |
| 1147. | a–d | Cl | bond | MeO | | | | |
| 1148. | a–d | Br | bond | MeO | | | | |
| 1149. | a–d | I | bond | MeO | | | | |
| 1150. | a–d | CN | bond | MeO | | | | |
| 1151. | a–d | F | bond | CHO | | | | |
| 1152. | a–d | Cl | bond | CHO | | | | |
| 1153. | a–d | Br | bond | CHO | | | | |
| 1154. | a–d | I | bond | CHO | | | | |
| 1155. | a–d | CN | bond | CHO | | | | |
| 1156. | a–d | F | bond | $NO_2$ | 78 | | | |
| 1157. | a–d | Cl | bond | $NO_2$ | | | | |
| 1158. | a–d | Br | bond | $NO_2$ | | | | |
| 1159. | a–d | I | bond | $NO_2$ | | | | |
| 1160. | a–d | CN | bond | $NO_2$ | | | | |
| 1161. | a–d | 3-$CF_3$-pyrazol-1-yl | bond | CN | see Ex. 5 | | 110 | |
| 1162. | a–d | 3-$CF_3$-pyrazol-1-yl | bond | Me | | | | |

TABLE 1-continued

|  |  | B | Y | R¹ | Melting point [° C.] a | b | c | d |
|---|---|---|---|---|---|---|---|---|
| 1163. | a–d | 3-CF$_3$-pyrazol-1-yl | bond | MeO | | | | |
| 1164. | a–d | 3-CF$_3$-pyrazol-1-yl | bond | CHO | | | | |
| 1165. | a–d | 3-CF$_3$-pyrazol-1-yl | bond | NO$_2$ | 128 | | | |
| 1166. | a–d | CH$_2$CH$_2$OMe | O | CN | 72 | | | |
| 1167. | a–d | CH$_2$CH$_2$OEt | O | CN | colorless oil | | | |
| 1168. | a–d | CH$_2$CH$_2$OnPr | O | CN | | | | |
| 1169. | a–d | CH$_2$CH$_2$OiPr | O | CN | colorless wax | 46 | | |
| 1170. | a–d | CH$_2$CH$_2$OCH$_2$OH$_2$OMe | O | CN | | | | |
| 1171. | a–d | CH$_2$CH$_2$OCH$_2$CH$_2$OEt | O | CN | colorless oil | | | |
| 1172. | a–d | CH$_2$CH$_2$SCF$_3$ | O | CN | colorless oil | | | |
| 1173. | a–d | CH$_2$CH$_2$CH$_2$SCF$_3$ | O | CN | | | | |
| 1174. | a–d | CH$_2$CH(OEt)$_2$ | O | CN | yellow oil | | light yellow resin | |
| 1175. | a–d | CH$_2$OH(OMe)$_2$ | O | CN | 84 | | | |
| 1176. | a–d | CH$_2$CH$_2$OCF$_3$ | O | CN | | | | |
| 1177. | a–d | CH$_2$CH$_2$CH$_2$OMe | O | CN | | | | |
| 1178. | a–d | CH$_2$CH$_2$CH$_2$OEt | O | CN | | | | |
| 1179. | a–d | CH$_2$CH$_2$CH$_2$OCF$_3$ | O | CN | | | | |
| 1180. | a–d | tetrahydrofur-2-yl | O—CH$_2$ | CN | colorless oil | | | |
| 1181. | a–d | tetrahydropyran-2-yl | O—CH$_2$ | CN | colorless oil | | | |
| 1182 | a–d | 2,2-dimethyl-1,3-dioxolan-4-yl | O—CH$_2$ | CN | colorless oil | 88 | | |
| 1183. | a–d | CH$_2$CH$_2$OMe | O | Me | | | | |
| 1184. | a–d | CH$_2$CH$_2$OEt | O | Me | | | | |
| 1185. | a–d | CH$_2$CH$_2$OnPr | O | Me | | | | |
| 1186. | a–d | CH$_2$CH$_2$OiPr | O | Me | | | | |
| 1187. | a–d | CH$_2$OH$_2$OCH$_2$OH$_2$OMe | O | Me | | | | |
| 1188. | a–d | CH$_2$OH$_2$OCH$_2$OH$_2$OEt | O | Me | | | | |
| 1189. | a–d | CH$_2$CH$_2$SCF$_3$ | O | Me | | | | |
| 1190. | a–d | CH$_2$CH$_2$CH$_2$SCF$_3$ | O | Me | | | | |
| 1191. | a–d | CH$_2$CH(OEt)$_2$ | O | Me | | | | |
| 1192. | a–d | CH$_2$CH(OMe)$_2$ | O | Me | | | | |
| 1193. | a–d | CH$_2$CH$_2$OCF$_3$ | O | Me | | | | |
| 1194. | a–d | CH$_2$CH$_2$CH$_2$OMe | O | Me | | | | |
| 1195. | a–d | CH$_2$CH$_2$CH$_2$OEt | O | Me | | | | |
| 1196. | a–d | CH$_2$CH$_2$CH$_2$OCF$_3$ | O | Me | | | | |
| 1197. | a–d | tetrahydrofur-2-yl | O—CH$_2$ | Me | | | | |
| 1198. | a–d | tetrahydropyran-2-yl | O—CH$_2$ | Me | | | | |
| 1199. | a–d | 2,2-dimethyl-1,3-dioxolan-4-yl | O—CH$_2$ | Me | | | | |
| 1200. | a–d | CH$_2$CH$_2$OMe | O | MeO | | | | |
| 1201. | a–d | CH$_2$CH$_2$OEt | O | MeO | | | | |
| 1202. | a–d | CH$_2$CH$_2$OnPr | O | MeO | | | | |
| 1203. | a–d | CH$_2$CH$_2$OiPr | O | MeO | | | | |
| 1204. | a–d | CH$_2$CH$_2$OCH$_2$CH$_2$OMe | O | MeO | | | | |
| 1205. | a–d | CH$_2$CH$_2$OCH$_2$CH$_2$OEt | O | MeO | | | | |
| 1206. | a–d | CH$_2$OH$_2$SCF$_3$ | O | MeO | | | | |
| 1207. | a–d | CH$_2$CH$_2$CH$_2$SCF$_3$ | O | MeO | | | | |
| 1208. | a–d | CH$_2$CH(OEt)$_2$ | O | MeO | | | | |
| 1209. | a–d | CH$_2$CH(OMe)$_2$ | O | MeO | | | | |
| 1210. | a–d | CH$_2$CH$_2$OCF$_3$ | O | MeO | | | | |
| 1211. | a–d | CH$_2$CH$_2$CH$_2$OMe | O | MeO | | | | |
| 1212. | a–d | CH$_2$CH$_2$CH$_2$OEt | O | MeO | | | | |
| 1213. | a–d | CH$_2$CH$_2$CH$_2$OCF$_3$ | O | MeO | | | | |
| 1214. | a–d | tetrahydrofur-2-yl | O—CH$_2$ | MeO | | | | |
| 1215. | a–d | tetrahydropyran-2-yl | O—CH$_2$ | MeO | | | | |
| 1216. | a–d | 2,2-dimethyl-1,3-dioxolan-4-yl | O—CH$_2$ | MeO | | | | |
| 1217. | a–d | CH$_2$CH$_2$OMe | O | CHO | | | | |
| 1218. | a–d | CH$_2$CH$_2$OEt | O | CHO | | | | |
| 1219. | a–d | CH$_2$CH$_2$OnPr | O | CHO | | | | |
| 1220. | a–d | CH$_2$CH$_2$OiPr | O | CHO | | | | |
| 1221. | a–d | CH$_2$CH$_2$OCH$_2$CH$_2$OMe | O | CHO | | | | |

TABLE 1-continued

| | | B | Y | R¹ | Melting point [° C.] | | | |
|---|---|---|---|---|---|---|---|---|
| | | | | | a | b | c | d |
| 1222. | a–d | CH$_2$CH$_2$OCH$_2$CH$_2$OEt | O | CHO | | | | |
| 1223. | a–d | CH$_2$CH$_2$SCF$_3$ | O | CHO | | | | |
| 1224. | a–d | CH$_2$CH$_2$CH$_2$SCF$_3$ | O | CHO | | | | |
| 1225. | a–d | CH$_2$CH(OEt)$_2$ | O | CHO | | | | |
| 1226. | a–d | CH$_2$CH(OMe)$_2$ | O | CHO | | | | |
| 1227. | a–d | CH$_2$CH$_2$OCF$_3$ | O | CHO | | | | |
| 1228. | a–d | CH$_2$CH$_2$CH$_2$OMe | O | CHO | | | | |
| 1229. | a–d | CH$_2$CH$_2$CH$_2$OEt | O | CHO | | | | |
| 1230. | a–d | CH$_2$CH$_2$CH$_2$OCF$_3$ | O | CHO | | | | |
| 1231. | a–d | tetrahydrofur-2-yl | O—CH$_2$ | CHO | | | | |
| 1232. | a–d | tetrahydropyran-2-yl | O—CH$_2$ | CHO | | | | |
| 1233. | a–d | 2,2-dimethyl-1,3-dioxolan-4-yl | O—CH$_2$ | CHO | | | | |
| 1234. | a–d | CH$_2$CH$_2$OMe | O | NO$_2$ | | | | |
| 1235. | a–d | CH$_2$CH$_2$OEt | O | NO$_2$ | | | | |
| 1236. | a–d | CH$_2$CH$_2$OnPr | O | NO$_2$ | | | | |
| 1237. | a–d | CH$_2$CH$_2$OiPr | O | NO$_2$ | light yellow oil | | | |
| 1238. | a–d | CH$_2$CH$_2$OCH$_2$CH$_2$OMe | O | NO$_2$ | | | | |
| 1239. | a–d | CH$_2$CH$_2$OCH$_2$CH$_2$OEt | O | NO$_2$ | | | | |
| 1240. | a–d | CH$_2$CH$_2$SCF$_3$ | O | NO$_2$ | | | | |
| 1241. | a–d | CH$_2$OH$_2$CH$_2$SCF$_3$ | O | NO$_2$ | | | | |
| 1242. | a–d | CH$_2$CH(OEt)$_2$ | O | NO$_2$ | light yellow oil | | | |
| 1243. | a–d | CH$_2$CH(OMe)$_2$ | O | NO$_2$ | light yellow oil | | | |
| 1244. | a–d | CH$_2$CH$_2$OCF$_3$ | O | NO$_2$ | | | | |
| 1245. | a–d | CH$_2$CH$_2$CH$_2$OMe | O | NO$_2$ | | | | |
| 1246. | a–d | CH$_2$CH$_2$CH$_2$OEt | O | NO$_2$ | | | | |
| 1247. | a–d | CH$_2$CH$_2$CH$_2$OCF$_3$ | O | NO$_2$ | | | | |
| 1248. | a–d | tetrahydrofur-2-yl | O—CH$_2$ | NO$_2$ | 99 | | | |
| 1249. | a–d | tetrahydropyran-2-yl | O—CH$_2$ | NO$_2$ | | | | |
| 1250. | a–d | 2,2-dimethyl-1,3-dioxolan-4-yl | O—CH$_2$ | NO$_2$ | light yellow resin | | | |
| 1251. | a–d | NH$_2$ | CO | CONH$_2$ | 271–272 | | | 291 |
| 1252. | a–d | Me | O | CN | 60 | | orange oil | |
| 1253. | a–d | Me | O | Me | | | | |
| 1254. | a–d | Me | O | MeO | | | | |
| 1255. | a–d | Me | O | CHO | | | | |
| 1256. | a–d | Me | O | NO$_2$ | | | | |
| 1257. | a–d | Et | O | CN | white resin | | | |
| 1258. | a–d | Et | O | Me | | | | |
| 1259. | a–d | Et | O | MeO | | | | |
| 1260. | a–d | Et | O | CHO | | | | |
| 1261. | a–d | Et | O | NO$_2$ | | | | |
| 1262. | a–d | iPr | O | CN | | | | |
| 1263. | a–d | iPr | O | Me | | | | |
| 1264. | a–d | iPr | O | MeO | | | | |
| 1265. | a–d | iPr | O | CHO | | | | |
| 1266. | a–d | iPr | O | NO$_2$ | | | | |
| 1267. | a–d | nPr | O | CN | | | | |
| 1268. | a–d | nPr | O | Me | | | | |
| 1269. | a–d | nPr | O | MeO | | | | |
| 1270. | a–d | nPr | O | CHO | | | | |
| 1271. | a–d | nPr | O | NO$_2$ | | | | |
| 1272. | a–d | nBu | O | CN | | | | |
| 1273. | a–d | nBu | O | Me | | | | |
| 1274. | a–d | nBu | O | MeO | | | | |
| 1275. | a–d | nBu | O | CHO | | | | |
| 1276. | a–d | nBu | O | NO$_2$ | | | | |
| 1277. | a–d | OH$_2$CF$_3$ | O | CN | | | | |
| 1278. | a–d | OH$_2$CF$_3$ | O | Me | | | | |
| 1279. | a–d | CH$_2$CF$_3$ | O | MeO | | | | |
| 1280. | a–d | CH$_2$CF$_3$ | O | CHO | | | | |
| 1281. | a–d | CH$_2$CF$_3$ | O | NO$_2$ | | | | |
| 1282. | a–d | CH$_2$CF$_2$CF$_3$ | O | CN | 78 | | | |
| 1283. | a–d | CH$_2$CF$_2$CF$_3$ | O | Me | | | | |
| 1284. | a–d | CH$_2$CF$_2$CF$_3$ | O | MeO | | | | |
| 1285. | a–d | CH$_2$CF$_2$CF$_3$ | O | CHO | | | | |
| 1286. | a–d | CH$_2$CF$_2$CF$_3$ | O | NO$_2$ | | | | |
| 1287. | a–d | CH$_2$CH$_2$CF$_3$ | O | CN | colorless resin | | | |

TABLE 1-continued

|  |  | B | Y | R$^1$ | Melting point [° C.] | | | |
|---|---|---|---|---|---|---|---|---|
|  |  |  |  |  | a | b | c | d |
| 1288. | a–d | CH$_2$CH$_2$CF$_3$ | O | Me | | | | |
| 1289. | a–d | CH$_2$CH$_2$CF$_3$ | O | MeO | | | | |
| 1290. | a–d | CH$_2$CH$_2$CF$_3$ | O | CHO | | | | |
| 1291. | a–d | CH$_2$OH$_2$CF$_3$ | O | NO$_2$ | | | | |
| 1292. | a–d | CH$_2$CH$_2$Cl | O | CN | | | | |
| 1293. | a–d | CH$_2$CH$_2$Cl | O | Me | | | | |
| 1294. | a–d | CH$_2$CH$_2$Cl | O | MeO | | | | |
| 1295. | a–d | CH$_2$CH$_2$Cl | O | CHO | | | | |
| 1296. | a–d | CH$_2$CH$_2$Cl | O | NO$_2$ | | | | |
| 1297. | a–d | CH$_2$CH$_2$SMe | O | CN | | | | |
| 1298. | a–d | CH$_2$CH$_2$SMe | O | Me | | | | |
| 1299. | a–d | CH$_2$CH$_2$SMe | O | MeO | | | | |
| 1300. | a–d | CH$_2$CH$_2$SMe | O | CHO | | | | |
| 1301. | a–d | CH$_2$CH$_2$SMe | O | NO$_2$ | | | | |
| 1302. | a–d | CH$_2$CH$_2$CH$_2$Cl | O | CN | | | | |
| 1303. | a–d | CH$_2$CH$_2$CH$_2$Cl | O | Me | | | | |
| 1304. | a–d | CH$_2$CH$_2$CH$_2$Cl | O | MeO | | | | |
| 1305. | a–d | CH$_2$CH$_2$CH$_2$Cl | O | CHO | | | | |
| 1306. | a–d | CH$_2$CH$_2$CH$_2$Cl | O | NO$_2$ | | | | |
| 1307. | a–d | CH$_2$CH=CH$_2$ | CO | CN | | | | |
| 1308. | a–d | CH$_2$CH=CH$_2$ | CO | Me | | | | |
| 1309. | a–d | CH$_2$CH=CH$_2$ | CO | MeO | | | | |
| 1310. | a–d | CH$_2$CH=CH$_2$ | CO | CHO | | | | |
| 1311. | a–d | CH$_2$CH=CH$_2$ | CO | NO$_2$ | | | | |
| 1312. | a–d | Me | CO | CN | | | | |
| 1313. | a–d | Me | CO | Me | | | | |
| 1314. | a–d | Me | CO | MeO | | | | |
| 1315. | a–d | Me | CO | CHO | | | | |
| 1316. | a–d | Me | CO | NO$_2$ | | | | |
| 1317. | a–d | Et | CO | CN | | | | |
| 1318. | a–d | Et | CO | Me | | | | |
| 1319. | a–d | Et | CO | MeO | | | | |
| 1320. | a–d | Et | CO | CHO | | | | |
| 1321. | a–d | Et | CO | NO$_2$ | | | | |
| 1322. | a–d | CH$_2$CH$_2$CHMe$_2$ | CO | CN | | | | |
| 1323. | a–d | CH$_2$CH$_2$CHMe$_2$ | CO | Me | | | | |
| 1324. | a–d | CH$_2$CH$_2$CHMe$_2$ | CO | MeO | | | | |
| 1325. | a–d | CH$_2$CH$_2$CHMe$_2$ | CO | CHO | | | | |
| 1326. | a–d | CH$_2$CH$_2$OHMe$_2$ | CO | NO$_2$ | | | | |
| 1327. | a–d | Ph | CO—CH$_2$ | CN | | | | |
| 1328. | a–d | Ph | CO—CH$_2$ | Me | | | | |
| 1329. | a–d | Ph | CO—CH$_2$ | MeO | | | | |
| 1330. | a–d | Ph | CO—CH$_2$ | CHO | | | | |
| 1331. | a–d | Ph | CO—CH$_2$ | NO$_2$ | | | | |
| 1332. | a–d | c-Pentyl | CO | CN | colorless resin | | | |
| 1333. | a–d | c-Pentyl | CO | Me | | | | |
| 1334. | a–d | c-Pentyl | CO | MeO | | | | |
| 1335. | a–d | c-Pentyl | CO | CHO | | | | |
| 1336. | a–d | c-Pentyl | CO | NO$_2$ | | | | |
| 1337. | a–d | iPr | CO | CN | colorless resin | | | |
| 1338. | a–d | iPr | CO | Me | | | | |
| 1339. | a–d | iPr | CO | MeO | | | | |
| 1340. | a–d | iPr | CO | CHO | | | | |
| 1341. | a–d | iPr | CO | NO$_2$ | | | | |
| 1342. | a–d | cPr | CO | CN | | | | |
| 1343. | a–d | cPr | CO | Me | | | | |
| 1344. | a–d | cPr | CO | MeO | | | | |
| 1345. | a–d | cPr | CO | CHO | | | | |
| 1346. | a–d | cPr | CO | NO$_2$ | | | | |
| 1347. | a–d | cBu | CO | CN | | | | |
| 1348. | a–d | cBu | CO | Me | | | | |
| 1349. | a–d | cBu | CO | MeO | | | | |
| 1350. | a–d | cBu | CO | CHO | | | | |
| 1351. | a–d | cBu | CO | NO$_2$ | | | | |
| 1352. | a–d | nPr | CO | CN | | | | |
| 1353. | a–d | nPr | CO | Me | | | | |
| 1354. | a–d | nPr | CO | MeO | | | | |
| 1355. | a–d | nPr | CO | CHO | | | | |
| 1356. | a–d | nPr | CO | NO$_2$ | | | | |
| 1357. | a–d | nBu | CO | CN | | | | |
| 1358. | a–d | nBu | CO | Me | | | | |
| 1359. | a–d | nBu | CO | MeO | | | | |
| 1360. | a–d | nBu | CO | CHO | | | | |

TABLE 1-continued

|  |  |  |  |  | Melting point [° C.] | | | |
|---|---|---|---|---|---|---|---|---|
|  | B | Y | $R^1$ | a | b | c | d |  |
| 1361. a–d | nBu | CO | $NO_2$ |  |  |  |  |
| 1362. a–d | Ph | CO | CN |  |  |  |  |
| 1363. a–d | Ph | CO | Me |  |  |  |  |
| 1364. a–d | Ph | CO | MeO |  |  |  |  |
| 1365. a–d | Ph | CO | CHO |  |  |  |  |
| 1366. a–d | Ph | CO | $NO_2$ |  |  |  |  |
| 1367. a–d | 1-$CH_3$-3-$CF_3$-pyrazol-5-yl | O | COOMe | colorless wax |  |  |  |
| 1368. a–d | Ph | O—$CH_2$ | CN | light yellow resin |  |  |  |
| 1369. a–d | Ph | O—$CH_2$ | Me |  |  |  |  |
| 1370. a–d | Ph | O—$CH_2$ | MeO |  |  |  |  |
| 1371. a–d | Ph | O—$CH_2$ | CHO |  |  |  |  |
| 1372. a–d | Ph | O—$CH_2$ | $NO_2$ |  |  |  |  |
| 1373. a–d | 4-F-Ph | O—$CH_2$ | CN | colorless oil |  |  |  |
| 1374. a–d | 4-F-Ph | O—$CH_2$ | Me |  |  |  |  |
| 1375. a–d | 4-F-Ph | O—$CH_2$ | MeO |  |  |  |  |
| 1376. a–d | 4-F-Ph | O—$CH_2$ | CHO |  |  |  |  |
| 1377. a–d | 4-F-Ph | O—$CH_2$ | $NO_2$ |  |  |  |  |
| 1378. a–d | 2,4-$F_2$-Ph | O—$CH_2$ | CN | yellow oil |  |  |  |
| 1379. a–d | 2,4-$F_2$-Ph | O—$CH_2$ | Me |  |  |  |  |
| 1380. a–d | 2,4-$F_2$-Ph | O—$CH_2$ | MeO |  |  |  |  |
| 1381. a–d | 2,4-$F_2$-Ph | O—$CH_2$ | CHO |  |  |  |  |
| 1382. a–d | 2,4-$F_2$-Ph | O—$CH_2$ | $NO_2$ |  |  |  |  |
| 1383. a–d | 3,4-$F_2$-Ph | O—$CH_2$ | CN | colorless oil |  |  |  |
| 1384. a–d | 3,4-$F_2$-Ph | O—$CH_2$ | Me |  |  |  |  |
| 1385. a–d | 3,4-$F_2$-Ph | O—$CH_2$ | MeO |  |  |  |  |
| 1386. a–d | 3,4-$F_2$-Ph | O—$CH_2$ | CHO |  |  |  |  |
| 1387. a–d | 3,4-$F_2$-Ph | O—$CH_2$ | $NO_2$ |  |  |  |  |
| 1388. a–d | 2-Me-Ph | O—$CH_2$ | CN | 113 |  |  |  |
| 1389. a–d | 2-Me-Ph | O—$CH_2$ | Me |  |  |  |  |
| 1390. a–d | 2-Me-Ph | O—$CH_2$ | MeO |  |  |  |  |
| 1391. a–d | 2-Me-Ph | O—$CH_2$ | CHO |  |  |  |  |
| 1392. a–d | 2-Me-Ph | O—$CH_2$ | $NO_2$ |  |  |  |  |
| 1393. a–d | 3-$CF_3$-Ph | O—$CH_2$ | CN | colorless oil |  |  |  |
| 1394. a–d | 3-$CF_3$-Ph | O—$CH_2$ | Me |  |  |  |  |
| 1395. a–d | 3-$CF_3$-Ph | O—$CH_2$ | MeO |  |  |  |  |
| 1396. a–d | 3-$CF_3$-Ph | O—$CH_2$ | CHO |  |  |  |  |
| 1397. a–d | 3-$CF_3$-Ph | O—$CH_2$ | $NO_2$ |  |  |  |  |
| 1398. a–d | 3-$CF_3$-phenyl | O | $CONH_2$ | 155 | white resin |  |  |
| 1399. a–d | 3-Cl-4-F-phenyl | O | CN | yellow resin |  |  |  |
| 1400. a–d | 3-$CF_3$-4-F-phenyl | O | CN | yellow resin |  |  |  |
| 1401. a–d | 3-$CF_3$-4-Cl-phenyl | O | CN | yellow wax-like solid |  |  |  |
| 1402. a–d | 3,4-$Me_2$-phenyl | O | CN | yellow resin |  |  |  |
| 1403. a–d | 3,4,5-$Me_3$-phenyl | O | CN | yellow resin |  |  |  |
| 1404. a–d | 1-$CH_3$-3-$CHF_2$-pyrazol-5-yl | O | CN | light yellow resin |  |  |  |
| 1405. a–d | 1-$CH_3$-3-$CF_3$-pyrazol-5-yl | O | COOMe | colorless oil |  |  |  |
| 1406. a–d | 1-$CH_3$-3-$CF_3$-pyrazol-5-yl | O | Cl | light yellow oil |  |  |  |
| 1407. a–d | 1-$CH_2$-3-$CF_3$-pyrazol-5-yl | O | $NH_2$ | 117 |  |  |  |
| 1408. a–d | 4,5-$Cl_2$-imidazol-1-yl | bond | CN | colorless oil |  |  |  |
| 1409. a–d | 1-$CH_3$-3-$CF_3$-pyrazol-5-yl | O | COOH | yellow resin |  |  |  |
| 1410. a–d | 1-$CH_3$-3-$CF_3$-pyrazol-5-yl | O | COMe | 116 |  |  |  |
| 1411. a–d | 1-$CH_3$-3-$CF_3$-pyrazol-5-yl | O | F | 73 |  |  |  |
| 1412. a–d | 1-$CH_3$-3-$CF_3$-pyrazol-5-yl | O | C(=$CH_2$)Me | semi-crystalline white |  |  |  |
| 1413. a–d | 1-$CH_3$-3-$CF_3$-pyrazol-5-yl | O | $CSNH_2$ | 159 |  |  |  |

TABLE 1-continued

| | | B | Y | R¹ | a | b | c | d |
|---|---|---|---|---|---|---|---|---|
| | | | | | \multicolumn{4}{c}{Melting point [° C.]} |
| 1414. | a–d | 1-CH$_3$-3-t-Bu-pyrazol-5-yl | O | CN | colorless oil | | | |
| 1415. | a–d | NH-4-F-Ph | CO | F | white crystals | | | |
| 1416. | a–d | NH-2,4-F$_2$-phenyl | CO | F | white crystals | | | |
| 1417. | a–d | NH$_2$ | CH$_2$ | F | yellow resin | | | |
| 1418. | a–d | NH$_2$ | CH$_2$ | CF$_3$ | light yellow resin | | | |
| 1419. | a–d | 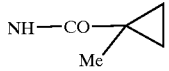 NH—CO—⟨△⟩—Me | CH$_2$ | F | colorless oil | | | |
| 1420. | a–d | NH—CO-tBu | CH$_2$ | F | yellow oil | | | |
| 1421. | a–d | NH—CO-Et | CH$_2$ | F | 75 | | | |
| 1422. | a–d | NH—COOMe | CH$_2$ | F | yellow oil | | | |
| 1423. | a–d | NH—CO—CF$_3$ | CH$_2$ | F | yellow oil | | | |
| 1424. | a–d | NH—CO-iPr | CH$_2$ | F | 102 | | | |
| 1425. | a–d | NH—CO-cPr | CH$_2$ | F | 104 | | | |
| 1426. | a–d | NH—COOMe | CH$_2$ | CF$_3$ | 78 | | | |
| 1427. | a–d | NH—CO—CF$_3$ | CH$_2$ | CF$_3$ | yellow resin | | | |
| 1428. | a–d | 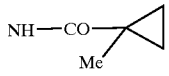 NH—CO—⟨△⟩—Me | CH$_2$ | CF$_3$ | 137 | | | |
| 1429. | a–d | NH—COiPr | CH$_2$ | CF$_3$ | 123 | | | |
| 1430. | a–d | NH—COcPr | CH$_2$ | CF$_3$ | 118 | | | |
| 1431. | a–d | NH—COOMe | CH$_2$ | OMe | colorless resin | | | |
| 1432. | a–d | 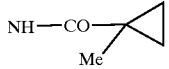 NH—CO—⟨△⟩—Me | CH$_2$ | OMe | 89 | | | |
| 1433. | a–d | NH—CH$_2$CH$_2$SO$_2$Me | CO | F | 132 | | | |
| 1434. | a–d | NH$_2$ | CO | CN | 240 | | 135 | |
| 1435. | a–d | NH$_2$ | CO | F | 186 | | | |
| 1436. | a–d | (E)-CH$_2$CH=CH—CH$_2$Cl | O | CN | colorless oil | | | |
| 1437. | a–d | (Z)-CH$_2$CH=CH—CH$_2$Cl | O | CN | semi-crystalline colorless | | | |
| 1438. | a–d | (E)-CH$_2$CH=CHCl | O | CN | | | brown resin | |
| 1439. | a–d | CH$_2$—C(OCH$_2$OMe)CH$_2$ | O | CN | colorless oil | | | |
| 1440. | a–d | H | O | CN | 155 | | | |
| 1441. | a–d | SO$_2$CF$_3$ | O | CN | light yellow oil | | | |
| 1442. | a–d | (E)-CH$_2$CH=CHCl | O | CN | yellow resin | | | |
| 1443. | a–d | (Z)-CH$_2$CH=CHCl | O | CN | yellow resin | | | |
| 1444. | a–d | (E)-CH$_2$CH=CClMe | O | CN | colorless resin | | | |
| 1445. | a–d | (Z)-CH$_2$CCl=CHCl | O | CN | beige resin | | | |
| 1446. | a–d | (E)-CH$_2$CCl=CHCl | O | CN | brown resin | | | |
| 1447. | a–d | CF$_3$ | bond | CN | 86 | | | |
| 1448. | a–d | F | bond | Cl | light yellow oil | | | |
| 1449. | a–d | F | bond | Br | yellow oil | | | |
| 1450. | a–d | F | bond | F | colorless oil | | | |

TABLE 1-continued

|  |  | B | Y | R$^1$ | Melting point [° C.] | | | |
|---|---|---|---|---|---|---|---|---|
|  |  |  |  |  | a | b | c | d |
| 1451. | a–d | CH$_2$CH$_2$C(Me)$_2$OMe | O | CN | colorless resin | | | |
| 1452. | a–d | CH$_2$Ph | O | CN | 88 | | | |
| 1453. | a–d | Cl—NO$_2$-imidazol-1-yl | bond | CN | 220 | | | |
| 1454. | a–d | 4-CF$_3$-imidazol-1-yl | bond | CN | colorless Oil | | | |
| 1455. | a–d | 4-CF$_3$-pyrazol-1-yl | bond | CN | 130 | | 112 | |
| 1456. | a–d | 4-CF$_3$-pyrazol-1-yl | bond | CONH$_2$ | colorless oil | | | |
| 1457. | a–d | pyrrolyl | bond | CN | orange oil | | | |
| 1458. | a–d | Imidazolyl | bond | CN | colorless oil | | | |
| 1459. | a–d | 4-Me-Imidazol-1-yl | bond | CN | colorless oil | | | |
| 1460. | a–d | 4-Br-pyrazol-1-yl | bond | CN | semi-crystalline, white | | | |
| 1461. | a–d | pyrazol-1-yl | bond | CN | colorless oil | | | |
| 1462. | a–d | 1,2,4-triazol-1-yl | bond | CN | 161 | | | |
| 1463. | a–d | 4-Br-3,5-dimethyl-pyrazol-1-yl | bond | CN | 90 | | | |
| 1464. | a–d | 3-MeOOC-imidazol-1-yl | bond | CN | 214 | | | |
| 1465. | a–d | CH$_2$CH$_2$OPh | O | CN | colorless resin | | | |
| 1466. | a–d | CH$_2$CH$_2$CH(Me)(OMe) | O | CN | light yellow oil | | | |
| 1467. | a–d | CH$_2$CH$_2$CH(OEt)$_2$ | O | CN | colorless resin | | | |
| 1468. | a–d | CH$_2$CH$_2$NMe$_2$ | O | CN | light brown oil | | | |
| 1469. | a–d | CH$_2$CH$_2$SMe | O | CN | colorless resin | | | |
| 1470. | a–d | 1,3-dioxolan-4-yl | O—CH$_2$ | CN | brown resin | | | |
| 1471. | a–d | CH$_2$CH(OEt)$_2$ | O | COMe | brown oil | | | |
| 1472. | a–d | Me | S | CN | 100 | | | |
| 1473. | a–d | Me | SO | CN | 116 | | | |
| 1474. | a–d | Me | SO$_2$ | CN | 140 | | | |
| 1475. | a–d | CH$_2$CHO | O | CN | yellow oil | | | |
| 1476. | a–d | 1,3-dioxolan-2-yl | O—CH$_2$ | CN | colorless resin | | | |
| 1477. | a–d | 4-ethyl-1,3-dioxolan-2-yl | O—CH$_2$ | CN | 88 | | | |
| 1478. | a–d | 1,3-dioxan-2-yl | O—CH$_2$ | CN | 137 | | | |
| 1479. | a–d | trans-5-methoxy-1,3-dioxan-2-yl | O—CH$_2$ | CN | 165 | | | |
| 1480. | a–d | cis-5-methoxy-1,3-dioxan-2-yl | O—CH$_2$ | CN | 109 | | | |
| 1481. | a–d | 4-fluoromethyl-1,3-dioxolan-2-yl | O—CH$_2$ | CN | white resin | | | |
| 1482. | a–d | 1,3-dioxopen-2-yl | O—CH$_2$ | CN | colorless resin | | | |
| 1483. | a–d | cis-4,6-dimethyl-1,3-dioxan-2-yl | O—CH$_2$ | CN | 124 | | | |
| 1484. | a–d | trans-4,6-dimethyl-1,3-dioxan-2-yl | O—CH$_2$ | CN | 118 | | | |
| 1485. | a–d | 5,5-dimethyl-1,3 dioxan-2-yl | O—CH$_2$ | CN | 122 | | | |
| 1486. | a–d | CH$_2$CH$_2$CH$_2$CF$_3$ | O | CN | colorless resin | | | |
| 1487. | a–d | CH$_2$CH(OMe)$_2$ | O | F | light yellow oil | | | |
| 1488. | a–d | tetrahydrofur-2-yl | O—CH$_2$ | F | yellow resin | | | |
| 1489. | a–d | 2,2-dimethyl-1,3-dioxolan-4-yl | O—CH$_2$ | F | colorless oil | | | |
| 1490. | a–d | CH$_2$CH$_2$CH$_2$CF$_3$ | O | NO$_2$ | light yellow oil | | | |
| 1491. | a–d | CH$_2$CH$_2$CH$_2$CF$_3$ | O | F | light yellow oil | | | |

TABLE 1-continued

|  | B | Y | R$^1$ | Melting point [° C.] a | b | c | d |
|---|---|---|---|---|---|---|---|
| 1492. a–d | CH$_2$CH$_2$-cPr | O | CN | semi-crystalline colorless | | | |
| 1493. a–d | Me | CO | F | 60 | | | |
| 1494. a–d | CH$_2$CH(OEt)$_2$ | O | CSNH$_2$ | 92 | | | |
| 1495. a–d | Me | O | CSNH$_2$ | 121 | | | |
| 1496. a–d | 3-CF$_3$-pyrazole | bond | CSNH$_2$ | 101 | | | |
| 1497. a–d | (E)-CH$_2$CH=CClMe | O | CSNH$_2$ | 123 | | | |
| 1498. a–d | (E)-CH$_2$CH=CCl(CF$_3$) | O | CSNH$_2$ | 109 | | | |
| 1499. a–d | (E)-CH$_2$CH=CHCF$_3$ | O | CSNH$_2$ | 109 | | | |
| 1500. a–d | 3-Me-4-F-phenyl | bond | CN | 123 | | | |
| 1501. a–d | 4-CF$_3$O-phenyl | bond | CN | 74 | | | |
| 1502. a–d | 4-MeO-phenyl | bond | CN | 131 | | | |
| 1503. a–d | 3,4-(MeO)$_2$phenyl | bond | CN | 132 | | | |
| 1504. a–d | CH=CH-(4-F-phenyl) | bond | CN | 124 | | | |
| 1505. a–d | 4-CH$_3$-phenyl | bond | CN | 82 | | | |
| 1506. a–d | 4-CN-phenyl | bond | CN | 131 | | | |
| 1507. a–d | 4-F-phenyl | bond | CN | 96 | | | |
| 1508. a–d | 4-Cl-phenyl | bond | CN | 104 | | | |
| 1509. a–d | 3,4-F$_2$-phenyl | bond | CN | 109 | | | |
| 1510. a–d | 3-Cl,4-F-phenyl | bond | CN | 120 | | | |
| 1511. a–d | 3,4-Cl$_2$-phenyl | bond | CN | semi-crystalline brownish | | | |
| 1512. a–d | 4-CF$_3$-phenyl | bond | CN | colorless oil | | | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of ethoxylated nonylphenol as the emulsifier.

e) Water-dispersible granules are obtained by mixing 75 parts by weight of a compound of the formula (I), 10 parts by weight of calcium lignosulfonate, 5 parts by weight of sodium lauryl sulfate, 3 parts by weight of polyvinyl alcohol and 7 parts by weight of kaolin grinding the mixture on a pinned-disk mill and granulating the powder in a fluidized bed by spraying on water as the granulation liquid.

f) Water-dispersible granules are also obtained by homogenizing and precomminuting, on a colloid mill, 25 parts by weight of a compound of the formula (I), 5 parts by weight of sodium 2,2'-dinaphthylmethane-6,6'-disulfonate 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance nozzle.

C. Biological Examples

1. Pre-Emergence Effect on Weeds

Seeds or rhizome pieces of monocotyledonous and dicotyledonous weed plants were placed in sandy loam soil in cardboard pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the test results, compounds according to the invention have good herbicidal pre-emergence activity against a broad spectrum of weed grasses and broad-leafed weeds. For example, the compounds of Example Nos. 62a, 62b, 73d, 74c, 75a, 76a, 77a, 397a, 1136a, 1136c, 1140a, 1140c, 1140d, 1156a, 1161a, 1169a, 1171a, 1177a, 1180a, 1182a and other compounds of Table 1 have very good herbicidal activity against harmful plants such as *Sinapis alba, Chrysanthemum segetum, Avena sativa, Stellaria media, Echinochloa crus-galli, Lolium multiflorum,* Setaria spp., *Abutilon theophrasti, Amaranthus retroflexus* and *Panicum miliaceum* pre-emergence at an application rate of 2 kg and less of active substance per hectare.

2. Post-Emergence Effect on Weeds

Seeds or rhizome pieces of monocotyledonous and dicotyledonous weeds were placed in sandy loam soil in plastic pots, covered with soil and grown in a greenhouse under good growth conditions. Three weeks after sowing, the test plants were treated at the three-leaf stage. The compounds according to the invention which were formulated as wettable powders or emulsion concentrates were sprayed, at various dosages, onto the green parts of the plants at an application rate of 600 to 800 l of water/ha (converted). After the test plants had remained in the greenhouse for about 3 to 4 weeks under ideal growth conditions, the effect of the preparations was scored visually by comparison with untreated controls. The agents according to the invention also have good herbicidal activity post-emergence against a broad spectrum of economically important weed grasses and broad-leafed weeds. For example, the compounds of Example Nos. 62a, 62b, 73d, 74c, 75a, 76a, 77a, 397a, 1136a, 1136c, 1140a, 1140c, 1140d, 1156a, 1161a, 1169a, 1171a, 1177a, 1180a, 1182a and other compounds of Table 1 have very good herbicidal activity against harmful plants such as *Sinapis alba, Echinochloa crus-galli, Lolium multiflorum, Chrysanthemum segetum, Avena sativa, Stellaria media*, Setaria spp., *Abutilon theophrasti, Amaranthus retroflexus* and *Panicum miliaceum* post-emergence at an application rate of 2 kg and less of active substance per hectare.

3. Tolerance by Crop Plants

In further greenhouse experiments, seeds of a substantial number of crop plants and weeds were placed in sandy loam soil and covered with soil. Some of the pots were treated immediately as described under Section 1, and the remaining pots were placed in the greenhouse until the plants had developed two to three true leaves and then sprayed with various dosages of the compounds according to the invention, as described under Section 2. Visual scoring four to five weeks after the application and after the plants had been in the greenhouse revealed that compounds according to the invention left dicotyledonous crops such as soybean, cotton, oilseed rape, sugar beet or potatoes unharmed even when high dosages of active ingredient were used by the pre- and post-emergence method. Moreover, some substances also spared Gramineae crops such as barley, wheat, rye, sorghum species, corn or rice. Some of the compounds according to the invention have high selectivity, and they are therefore suitable for controlling undesirable vegetation in agricultural crops.

What is claimed is (US):

1. A herbicide or plant growth regulator comprising a compound of the formula (I) and/or a salt thereof

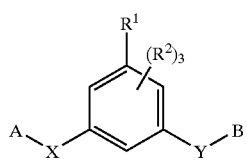

formula (I)

where

A is

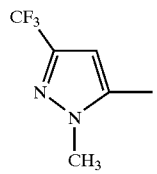

X is O, $R^1$ is hydroxyl, halogen, CN, NC, CHO, CO($C_1$–$C_8$)-alkyl, where the alkyl group is unsubstituted or substituted, $CONH_2$, $CSNH_2$, nitro, $SF_5$, ($C_1$–$C_8$)-alkyl, ($C_2$–$C_8$)-alkenyl, ($C_2$–$C_8$)-alkynyl($C_1$–$C_8$)-alkoxy, [($C_1$–$C_8$)-alkyl]carbonyl or ($C_1$–$C_8$)-alkylsulfonyl, where each of the six last-mentioned radicals is unsubstituted or substituted, or $S(O)_p$—$R^3$, where p=0, 1 or 2 and $R_3$ is ($C_1$–$C_8$)-alkyl($C_1$–$C_8$)-haloalkyl or $NR^4R^5$, where $R^4$, $R^5$ independently of one another are identical or different radicals H, ($C_1$–$C_8$)-alkyl, ($C_2$–$C_8$)-alkenyl, ($C_7$–$C_{10}$)-arylalkyl, ($C_7$–$C_{10}$)-alkylaryl or ($C_6$–$C_{10}$)-aryl, where each of the five last-mentioned radicals is unsubstituted or substituted, or is $NR^4R^5$, where $R^4$,$R^5$ independently of one another are identical or different radicals H($C_1$–$C_8$)-alkyl, ($C_2$–$C_8$)-alkenyl, ($C_7$–$C_{10}$)-arylalkyl, ($C_7$–$C_{10}$)-alkylaryl or ($C_6$–$C_{10}$)-aryl, where each of the five last-mentioned radicals is unsubstituted or substituted, or $R^1$ is a group of the formula

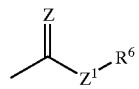

where $R^6$ is ($C_1$–$C_8$)-alkyl which is unsubstituted or substituted,

Z=O or S and $Z^1$=O or S, $R^2$ are identical or different radicals H, halogen, CN or ($C_1$–$C_8$)-alkyl, which are unsubstituted or substituted, Y is O—($CR^8R^9$)$_q$, $S(O)_q$, NH, $CO(CR^8R^9)_q$ or $CR^8R^9$ and, if B is a substituted or unsubstituted aryl radical, a substituted or unsubstituted heterocyclyl radical, halogen or CN, Y may also be a bond, where $R^8$ and $R^9$ are identical or different radicals H, hydroxyl, halogen, CN, ($C_1$–$C_8$)-alkoxy or ($C_1$–$C_8$)-alkyl, where each of the two last-mentioned radicals is unsubstituted or substituted, and q=0, 1 or 2, and B is an unsubstituted or substituted aryl radical, an unsubstituted or substituted heterocyclic radical, H, OH, halogen, CN, nitro, $SF_5$, ($C_1$–$C_8$)-alkyl, ($C_2$–$C_8$)-alkenyl or ($C_2$–$C_8$)-alkynyl, where the 3 last-mentioned radicals are unsubstituted or substituted, or an acyl radical or $NR^{11}R^{12}$, where $R^{11}$,$R^{12}$ independently of one another are identical or different radicals H, ($C_1$–$C_8$)-alkyl, ($C_2$–$C_8$)-alkenyl, ($C_7$–$C_{10}$)-arylalkyl, ($C_7$–$C_{10}$)-alkylaryl, ($C_6$–$C_{10}$)-aryl or heteroaryl, where each of the six last-mentioned radicals is unsubstituted or substituted, or an acyl radical, or B is a group of the formula

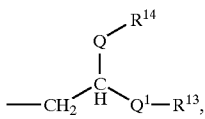

where $R^{13}$ is $(C_1-C_8)$-alkyl which is unsubstituted or substituted,
$R^{14}$ is $(C_1-C_8)$-alkyl which is unsubstituted or substituted,
or $R^{13}$ and $R^{14}$ together form a ring,
Q=O or S and
$Q^1$=O or S.

2. A herbicide or plant growth regulator, as claimed in claim 1,
where in the compound of formula (I)
$R^1$ is hydroxyl, halogen, CN, NC, CHO, $CO(C_1-C_8)$-alkyl, $COO(C_1-C_3$-alkyl), where the alkyl groups are unsubstituted or substituted, $CONH_2$, $CSNH_2$, nitro, $SF_5(C_1-C_8)$-alkyl, $(C_2-C_8)$alkenyl or $(C_1-C_8)$-alkoxy, where the 3 last-mentioned radicals are unsubstituted or substituted,
$R^2$ are identical or different radicals H, halogen, CN or $(C_1-C_8)$-alkyl, which are unsubstituted or substituted,
Y is O—$(CR^8R^9)_q$, $S(O)_q$, NH, $CO(CR^8R^9)_q$ or $CR^8R^9$ and, if B is an unsubstituted or substituted aryl radical, an unsubstituted or substituted heterocyclyl radical, halogen or CN, Y may also be a bond,
where $R^8$ and $R^9$ are identical or different radicals H, hydroxyl, halogen, CN, $(C_1-C_8)$-alkoxy or $(C_1-C_8)$-alkyl, where each of the two last-mentioned radicals is unsubstituted or substituted, and
q=0, 1 or 2, and
B is an aryl radical or a 5- or 6-membered heterocyclic radical, where the two radicals mentioned are unsubstituted or substituted by one or more radicals selected from the group consisting of hydroxyl, halogen, CN, $(C_1-C_8)$-alkyl$(C_1-C_8)$-alkoxy, halo-$(C_1-C_8)$-alkyl, halo-$(C_1-C_8)$-alkyloxy, halo-$(C_1-C_8)$-alkylthio and $(C_1-C_8)$-alkoxy-$(C_1-C_8)$-alkoxy, or H, OH, halogen, CN, nitro, $SF_5$, $(C_1-C_8)$-alkyl, $(C_2-C_8)$-alkenyl or $(C_2-C_8)$-alkynyl, where each of the three last-mentioned radicals is unsubstituted or substituted, or an acyl radical or
$N^{11}R^{12}$, where
$R^{11}$,$R^{12}$ independently of one another are identical or different radicals H, $(C_1-C_8)$-alkyl, $(C_2-C_8)$-alkenyl, $(C_7-C_{10})$-arylalkyl, $(C_7-C_{10})$-alkylaryl, $(C_6-C_{10})$-aryl or heteroaryl, where each of the six last-mentioned radicals is unsubstituted or substituted, or an acyl radical, or
B is a group of the formula

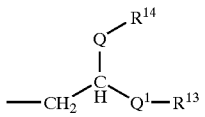

where $R^{13}$ is $(C_1-C_8)$-alkyl which is unsubstituted or substituted,
$R^{14}$ is $(C_1-C_8)$-alkyl which is unsubstituted or substituted,
or $R^{13}$ and $R^{14}$ together form a ring,
Q=O or S and
$Q^1$=O or S.

3. A herbicide or plant growth regulator, as claimed in claim 1, where in the compound of formula (I)
$R^1$ is hydroxyl, halogen, CN, NC, CHO, $CONH_2$, $CSNH_2$, nitro$(C_1-C_8)$-alkyl, $(C_2-C_8)$-alkenyl, $CO(C_1-C_3)$-alkyl, $COO(C_1-C_8)$-alkyl or $(C_1-C_8)$-alkoxy, where each of the five last-mentioned radicals is unsubstituted or substituted by one or more radicals selected from the group consisting of hydroxyl, halogen, CN, $(C_1-C_8)$-alkoxy and $(C_1-C_8)$-alkylthio,
$R^2$ are identical or different radicals H, halogen or CN,
Y is O—$(CR^8R^9)_q$, $S(O)_q$, NH, $CO(CR^8R^9)_q$ or $CR^8R^9$ and, if B is an unsubstituted or substituted aryl radical, an unsubstituted or substituted heterocyclyl radical, halogen or CN, Y may also be a bond,
where $R^8$ and $R^9$ are identical or different radicals H, hydroxyl, halogen, CN, $(C_1-C_8)$-alkoxy or $(C_1-C_8)$-alkyl, where each of the two last-mentioned radicals is unsubstituted or substituted, and
q=0, 1 or 2, and
B is an aryl radical or a 5- or 6-membered heterocyclic radical, where the two last-mentioned radicals are unsubstituted or substituted by one or more radicals selected from the group consisting of hydroxyl, halogen, $CN(C_1-C_8)$alkyl, $(C_1-C_8)$-alkoxy, halo-$(C_1-C_8)$-alkyl, halo-$(C_1-C_8)$-alkyloxy, halo-$(C_1-C_8)$-alkylthio and $(C_1-C_8)$-alkoxy-$(C_1-C_8)$-alkoxy, H, OH, halogen, CN, nitro, $SF_5(C_1-C_8)$-alkyl, $(C_2-C_8)$-alkenyl or $(C_2-C_8)$-alkynyl, where the three last-mentioned radicals are unsubstituted or substituted, or an acyl radical or
$NHR^{12}$, where
$R^{12}$ is H, $(C_1-C_8)$alkyl, $(C_2-C_8)$-alkenyl, $(C_7-C_{10})$-arylalkyl, $(C_7-C_{10})$-alkylaryl, $(C_6-C_{10})$-aryl or heteroaryl, where each of the six last-mentioned radicals is unsubstituted or substituted, or an acyl radical, or
B is a group of the formula

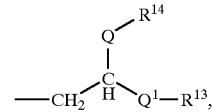

where $R^{13}$ is $(C_1-C_8)$-alkyl, which is unsubstituted or substituted,
$R^{14}$ is $(C_1-C_8)$-alkyl, which is unsubstituted or substituted,
or $R^{13}$ and $R^{14}$ together form a ring,
Q=O or S, and
$Q^1$=O or S.

4. A herbicidal or plant-growth-regulating composition, comprising a) at least one herbicide or plant growth regulator, as claimed in claim 1, and b) auxiliaries customary in crop protection.

5. A method for controlling harmful plants which comprises applying an effective amount of at least one herbicide or plant growth regulator, as claimed in claim 1, to the harmful plants, to seeds of the harmful plants or to the area in which the harmful plants grow.

6. A method of using the herbicide or plant growth regulator as claimed in claim 1, wherein the herbicide or plant growth regulator is applied to harmful plants, to seeds of harmful plants or to an area in which the harmful plants grow.

7. A method of using the herbicide or plant growth regulator of claim 1, wherein the herbicide or plant growth regulator is applied to either harmful plants to control said harmful plants, or to crop plants to regulate the growth of said crop plants.

8. The method as claimed in claim 7, where the crop plants are transgenic crop plants.

9. A process for preparing a compound of the formula (I) and/or a salt thereof,

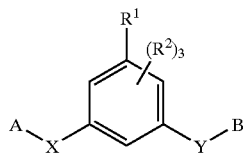

formula (I)

where

A is

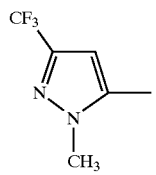

X is O $R^1$ is hydroxyl, halogen, CN, NC, CHO, $CO(C_1-C_8)$-alkyl, where the alkyl group is unsubstituted or substituted, $CONH_2$, $CSNH_2$, nitro, $SF_5$, $(C_1-C_8)$-alkyl, $(C_2-C_8)$-alkenyl, $C_2-C_8$-alkynyl, $(C_1-C_8)$-alkoxy, $[(C_1-C_8)$-alkyl]carbonyl or $(C_1-C_8)$-alkylsulfonyl, where each of the six last-mentioned radicals is unsubstituted or substituted, or $S(O)_p-R^3$, where p=0,1 or 2 and $R^3$ is $(C_1-C_8)$-haloalkyl or $NR^4 R^5$, where $R^4, R^5$ independently of one another are identical or different radicals H, $(C_1-C_8)$-alkyl, $(C_2-C_8)$-alkenyl, $(C_7-C_{10})$-arylalkyl, $(C_7-C_{10})$-alkylaryl or $(C_7-C_{10})$-aryl, where each of the five last-mentioned radicals is unsubstituted or substituted, or is $NR^4R^5$, where $R^4,R^5$ independently of one another are identical or different radicals H, $(C_1-C_8)$-alkyl, $(C_1-C_8)$-alkenyl, $(C_7-C_{10})$-arylalkyl, $(C_7-C_{10})$-alkylaryl or $(C_6-C_{10})$aryl, where each of the five last-mentioned radicals is unsubstituted or substituted, or $R^1$ is a group of the formula

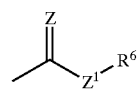

where $R^6$ is $(C_1-C_8)$-alkyl which is unsubstituted or substituted,

Z=O or S and $Z^1$=O or S, $R^2$ are identical or different radicals H, halogen, CN or $(C_1-C_8)$-alkyl, which are unsubstituted or substituted, Y is O—$(CR^8R^9)_q$, $S(O)_q$, NH, $CO(CR^8R^9$ or $CR^8R^9$ and, if B is a substituted or unsubstituted aryl radical, a substituted or unsubstituted heterocyclyl radical, halogen or CN, Y may also be a bond, where $R^8$ and $R^9$ are identical or different radicals H, hydroxyl, halogen, CN, $(C_1-C_8)$-alkoxy or $(C_1-C_8)$- alkyl, where each of the two last-mentioned radicals is unsubstituted or substituted, and q=0, 1 or 2, and B is an unsubstituted or substituted aryl radical, an unsubstituted or substituted heterocyclic radical, H, OH, halogen, CN, nitro, $SF_5(C_1-C_8)$-alkyl, $(C_2-C_8)$ alkenyl or $(C_1-C_8)$-alkynyl, where the 3 last-mentioned radicals are unsubstituted or substituted, or an acyl radical or $NR^{11}R^{12}$, where $R^{11}, R^{12}$ independently of one another are identical or different radicals H, $(C_1-C_8)$-alkyl, $(C_2-C_8)$-alkenyl, $(C_7-C_{10})$-arylalkyl, $(C_7-C_{10})$alkylaryl, $(C_6-C_{10})$-aryl or heteroaryl, where each of the six last-mentioned radicals is unsubstituted or substituted, or an acyl radical, or B is a group of the formula

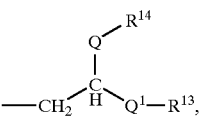

where $R^{13}$ is $(C_1-C_8)$-alkyl which is unsubstituted or substituted, $R^{14}$ is $(C_1-C_8)$-alkyl which is unsubstituted or substituted, or $R^{13}$ and $R^{14}$ together form a ring, O=O or S and $Q^1$=O or S, wherein said process comprises:

a) reacting a compound of the formula (II)

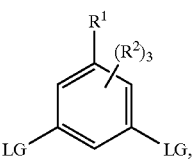

(II)

where $R^1$ and $R^2$ are defined above and LG are identical or different leaving groups with nucleophiles of the formula A-X—H and B—Y—H, where A, B, X and Y are as defined above; or b) reacting a compound of the formula (III) with a compound of the formula (IV)

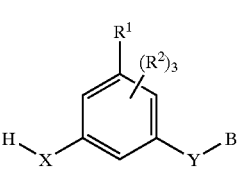

(III)

A—B or $(OH)_2$ (IV)

or a compound of the formula (III') with a compound of the formula (IV')

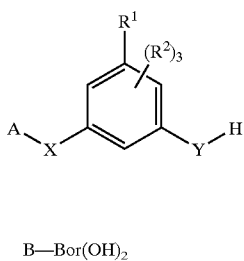
(III')

B—Bor(OH)₂    (IV')

where $R^1$, $R^2$, A, B, X and Y in the formulae (III), (III'), (IV) and (IV') are as defined above; or c) reacting a compound of the formula (V) with a compound of the formula A-X—H

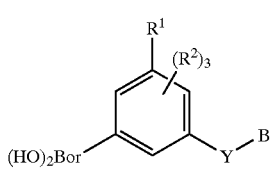
(V)

or a compound of the formula (V') with a compound of the formula B—Y—H

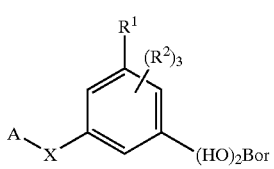
(V')

where $R^1$, $R^2$, A, B, X and Y in the formulae (V), (V'), A-X—H and B—Y—H are as defined above; or d) reducing and acylating a compound of the formula (VI)

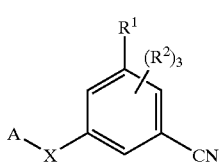
(VI)

where $R^1$, $R^2$, A and X in formula (VI) are as defined above; or e) hydrolyzing a compound of the formula (VI) and reacting it with an amine of the formula $NH_2$–$R^{12}$

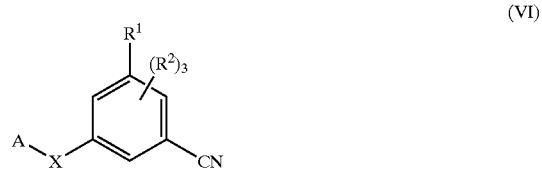
(VI)

where $R^1$, $R^2$, $R^{12}$, A and X in the formulae (VI) and $NH_2$–$R^{12}$ are as defined above; or f) reacting a compound of the formula (VI) with an organometallic compound

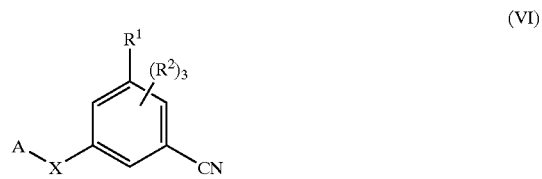
(VI)

where $R^1$, $R^2$, A and X in formula (VI) are as defined above.

10. A method for regulating the growth of crop plants, which comprises applying an effective amount of at least one herbicide or plant growth regulator, as claimed in claim 1, to the crop plants, to seeds of the crop plants or to the area in which the crop plants grow.

11. A method of using the herbicide or plant growth regulator, as claimed in claim 1, wherein the herbicide or plant growth regulator is applied to crop plants, to seeds of crop plants or to an area in which crop plants grow.

12. A method for simultaneously controlling harmful plants and regulating the growth of crop plants, wherein said harmful plants and said crop plants coexist in the same area, said method comprising the step of applying the herbicide or plant growth regulator of claim 1 to the harmful plants and the crop plants or applying the herbicide or plant growth regulator to the area where said harmful plants and said crop plants coexist in such a manner that said herbicide or plant growth regulator contacts said harmful plants and said crop plants.

* * * * *

UNITED STATES PATENT AND TRADEMARK OFFICE
CERTIFICATE OF CORRECTION

PATENT NO. : 6,750,222 B2
DATED : June 15, 2004
INVENTOR(S) : Hendrik Helmke et al.

It is certified that error appears in the above-identified patent and that said Letters Patent is hereby corrected as shown below:

Column 76,
Line 29, "H($C_1$-$C_8$)-alkyl," should read -- H, ($C_1$-$C_8$)-alkyl, --.

Column 77,
Line 20, "COO($C_1$-$C_3$-alkyl)" should read -- COO($C_1$-$C_8$-alkyl) --.
Line 40, "($C_1$-$C_8$)-alkyl($C_1$-$C_8$)-alkoxy," should read -- ($C_1$-$C_8$)-alkyl, ($C_1$-$C_8$)-alkoxy, --.
Line 47, "$N^{11}R^{12}$" should read -- $NR^{11}R^{12}$ --.

Column 78,
Line 5, "nitro($C_1$-$C_8$)-alkyl," should read -- nitro, ($C_1$-$C_8$)-alkyl, --.
Line 6, "CO($C_1$-$C_3$)-alkyl," should read -- CO($C_1$-$C_8$)-alkyl, --.
Line 25, "CN($C_1$-$C_8$)-alkyl," should read -- CN, ($C_1$-$C_8$)-alkyl, --.
Line 28, "$SF_5$($C_1$-$C_8$)-alkyl," should read -- $SF_5$, ($C_1$-$C_8$)-alkyl, --.

Column 79,
Line 32, "$C_2$-$C_8$)-alkynyl," should read -- ($C_2$-$C_8$)-alkynyl, --.
Line 38, after "$R^3$ is" insert -- ($C_1$-$C_8$)-alkyl, --.
Line 42, "($C_7$-$C_{10}$)-aryl," should read -- ($C_6$-$C_{10}$)-aryl, --.
Line 46, "($C_1$-$C_8$)-alkenyl," should read -- ($C_2$-$C_8$)-alkenyl, --.
Line 62, "CO($CR^8R^9$" should read -- CO($CR^8R^9$)$_q$ --.

Column 80,
Line 8, "$SF_5$($C_1$-$C_8$)-alkyl," should read -- $SF_5$, ($C_1$-$C_8$)-alkyl, --.
Lines 8-9, "($C_2$-$C_8$)alkenyl" should read -- ($C_2$-$C_8$)-alkenyl --.
Line 32, "O=O" should read -- Q = O --.

Signed and Sealed this

Twenty-first Day of December, 2004

JON W. DUDAS
*Director of the United States Patent and Trademark Office*